(12) United States Patent
Strongin et al.

(10) Patent No.: US 11,191,850 B2
(45) Date of Patent: Dec. 7, 2021

(54) MOLECULAR PROBES FOR DETECTION AND IMAGING OF PANCREATIC CANCER

(71) Applicant: Portland State University, Portland, OR (US)

(72) Inventors: Robert M Strongin, Portland, OR (US); Martha Sibrian-Vazquez, Portland, OR (US); Lei Wang, Camas, WA (US); Jorge O. Escobedo Cordova, Portland, OR (US); Mark A. Lowry, Portland, OR (US)

(73) Assignee: Portland State University, Portland, OR (US)

( * ) Notice: Subject to any disclaimer, the term of this patent is extended or adjusted under 35 U.S.C. 154(b) by 193 days.

(21) Appl. No.: 16/304,109

(22) PCT Filed: May 23, 2017

(86) PCT No.: PCT/US2017/033961
§ 371 (c)(1),
(2) Date: Nov. 21, 2018

(87) PCT Pub. No.: WO2017/205350
PCT Pub. Date: Nov. 30, 2017

(65) Prior Publication Data
US 2020/0330612 A1      Oct. 22, 2020

Related U.S. Application Data

(60) Provisional application No. 62/340,405, filed on May 23, 2016.

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *A61K 9/00* | (2006.01) | |
| *C07D 311/86* | (2006.01) | |
| *C07D 491/16* | (2006.01) | |
| *C09B 11/16* | (2006.01) | |
| *C09B 11/22* | (2006.01) | |
| *C09B 11/24* | (2006.01) | |
| *C09K 11/06* | (2006.01) | |

(52) U.S. Cl.
CPC ........ *A61K 49/0043* (2013.01); *A61K 9/0012* (2013.01); *A61K 49/006* (2013.01); *C07D 311/86* (2013.01); *C07D 491/16* (2013.01); *C09B 11/16* (2013.01); *C09B 11/22* (2013.01); *C09B 11/24* (2013.01); *C09K 11/06* (2013.01); *C09K 2211/1007* (2013.01); *C09K 2211/1018* (2013.01)

(58) Field of Classification Search
None
See application file for complete search history.

(56) References Cited

U.S. PATENT DOCUMENTS

| 6,534,316 B2 | 3/2003 | Strongin et al. |
|---|---|---|
| 8,927,727 B2 | 1/2015 | Strongin et al. |
| 9,250,246 B2 * | 2/2016 | Strongin .............. G01N 33/582 |
| 9,506,929 B2 | 11/2016 | Strongin et al. |
| 9,709,572 B2 | 7/2017 | Strongin et al. |
| 9,952,231 B2 | 4/2018 | Strongin et al. |
| 2008/0261315 A1 | 10/2008 | Strongin et al. |
| 2010/0051826 A1 | 3/2010 | Strongin et al. |
| 2012/0276649 A1 | 11/2012 | Strongin et al. |
| 2016/0223558 A1 | 8/2016 | Strongin et al. |

FOREIGN PATENT DOCUMENTS

| WO | WO 2005/110109 A2 | 11/2005 |
|---|---|---|
| WO | WO 2008/011508 A1 | 1/2008 |
| WO | WO 2013/003815 A2 | 1/2013 |
| WO | WO 2014/102803 A1 | 7/2014 |

OTHER PUBLICATIONS

Jayaraman (J. Immunological Methods 2005, 306, 68-79).*
Yang et al. (PNAS 2008, 105, 8829-8834).*
Iwatate et al. (Chem. Eur. J. 2016, 22, 1696-1703).*
Extended European Search Report, dated Nov. 29, 2019, issued in related European Patent Application No. 17803405.4, 8 pp.
Chevalier, A. et al., "Straightforward Access to Water-Soluble Unsymmetrical Sulfoxanthene Dyes: Application to the Preparation of Far-Red Fluorescent Dyes with Large Stokes' Shifts," *Chemistry—A European Journal*, 20:8330-8337 (Jul. 2014).
World Intellectual Property Organization, International Search Report, dated Sep. 3, 2017, for International Patent Application No. PCT/US2017/033961.
World Intellectual Property Organization, Written Opinion, dated Aug. 30, 2017, for International Patent Application No. PCT/US2017/033961.
Koresawa, M. et al., "Development of a time-resolved fluorometric detection system using diffusion-enhanced energy transfer," *Analytical Chemistry*, 72:4904-4907 (Oct. 2000).
Owens, E. A. et al., "Correlating molecular character of NIR imaging agents with tissue-specific uptake," *Journal of Medicinal Chemistry*, 58:4348-4356 (May 2015).
Sibrian-Vazquez, M. et al., "Field effects induce bathochromic shifts in xanthene dyes," *Journal of the American Chemical Society*, 134:10502-10508, (Jun. 2012).
Wada, H. et al., "Pancreas-targeted NIR fluorophores for dual-channel image-guided abdominal surgery," *Theranostics*, 5:1-11 (Jan. 2015).

(Continued)

*Primary Examiner* — Michael G. Hartley
*Assistant Examiner* — Melissa J Perreira
(74) *Attorney, Agent, or Firm* — Klarquist Sparkman, LLP

(57) ABSTRACT

Molecular probes for detecting and imaging pancreatic cancer are disclosed. The probes are modified benzoxanthene fluorophores, which are selectively taken up by pancreatic cancer cells, such as pancreatic ductal adenocarcinoma cells. Embodiments of the disclosed probes are useful for pancreatic cancer detection, therapeutic monitoring, and/or image-guided surgery.

14 Claims, 18 Drawing Sheets

(56) References Cited

OTHER PUBLICATIONS

Wang, L. et al., "Far-Red and Near-Infrared Seminaphthofluorophores for Targeted Pancreatic Cancer Imaging," *ACS Omega*, 2:154-163 (Jan. 2017).
Yang et al., "A Convenient Preparation of Xanthene Dyes," *Journal of Organic Chemistry* 70(17):6907-6912 (Jul. 2005).
Yang et al., "An Organic White Light-Emitting Fluorophore," *Journal of the American Chemical Society* 128(43):14081-14092 (Oct. 2006).
Yang et al., "An Organic White Light-Emitting Fluorophore," *Journal of the American Chemical Society* 129:1008 (Jan. 2007).
Yang et al., "Seminaphthofluorones are a family of water-soluble, low molecular weight, NIR-emitting fluorophores," *PNAS* 105(26):8829-8834 (Jul. 2008).
Bacci et al., "Efficient Two-Step Synthesis of 9-Aryl-6-hydroxy-3H-xanthen-3-one Fluorophores," *J. Org. Chem.* 2005, 70, 9051-9053.
Munhenzva et al., "Assessment of human pancreas cancer tissue and precursor lesions via a fluorophore with inherent PDAC selectivity," *Methods* 2019, 168, 35-39.
Wang et al., "Altering Fundamental Trends in the Emission of Xanthene Dyes," *J. Org. Chem.* 2019, 84, 2585-2595.

\* cited by examiner

| | | |
|---|---|---|
| 1 | $R^A$ = OH | $R^B$ = O |
| 2 | $R^A$ = $OCH_3$ | $R^B$ = O |
| 3 | $R^A$ = OH | $R^B$ = $^+NH_2$ |
| 4 | $R^A$ = $OCH_3$ | $R^B$ = $^+NH_2$ |
| 5 | $R^A$ = OH | $R^B$ = $^+N(CH_3)_2$ |
| 6 | $R^A$ = $OCH_3$ | $R^B$ = $^+N(CH_3)_2$ |
| 7 | $R^A$ = $NH_2$ | $R^B$ = O |
| 8 | $R^A$ = $N(CH_3)_2$ | $R^B$ = O |
| 9 | $R^A$ = $NH_2$ | $R^B$ = $^+NH_2$ |
| 10 | $R^A$ = $NH_2$ | $R^B$ = $^+N(CH_3)_2$ |

11 $R^1$ = OH
12 $R^1$ = $OCH_3$
13 $R^1$ = $NH_2$

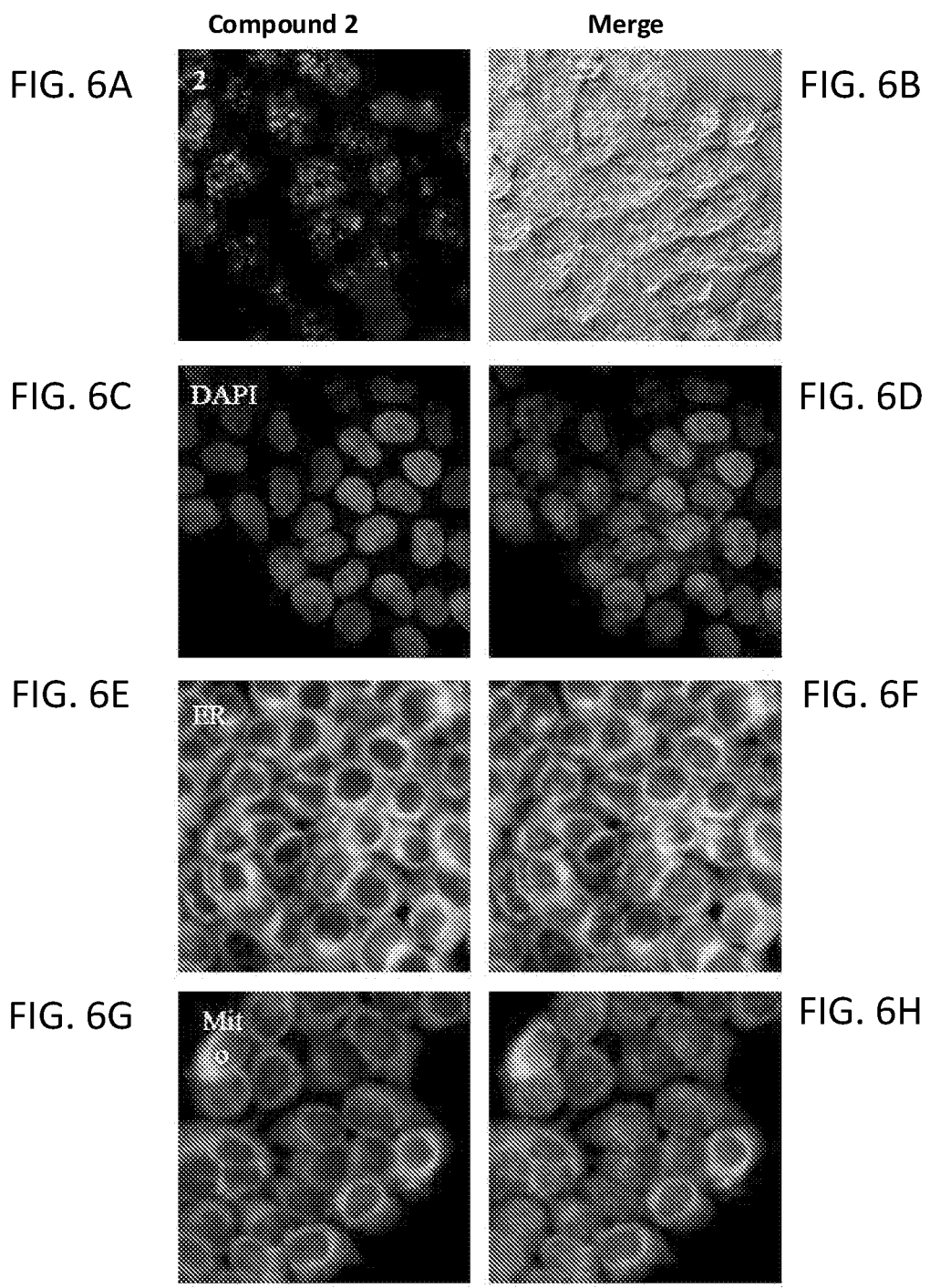

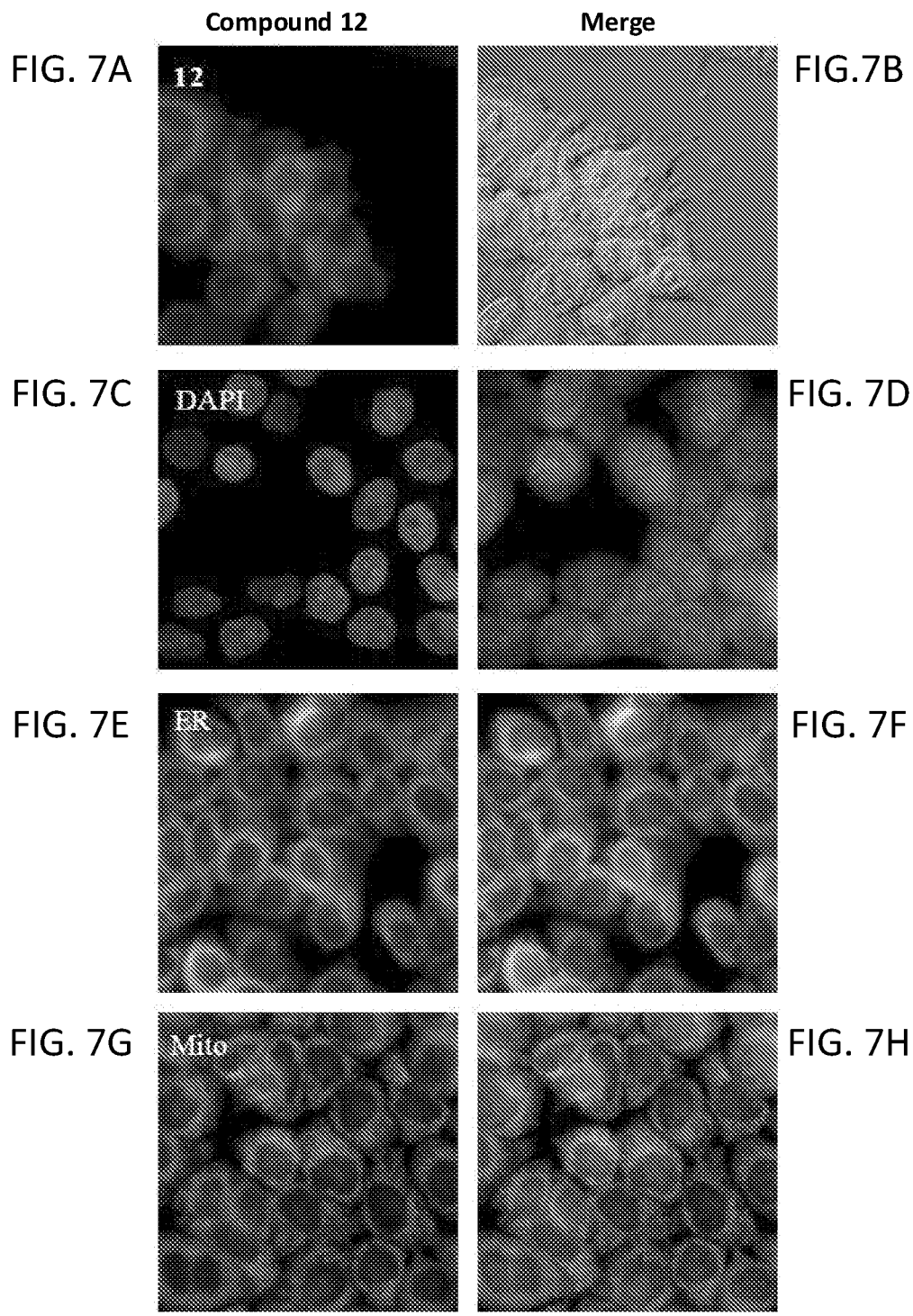

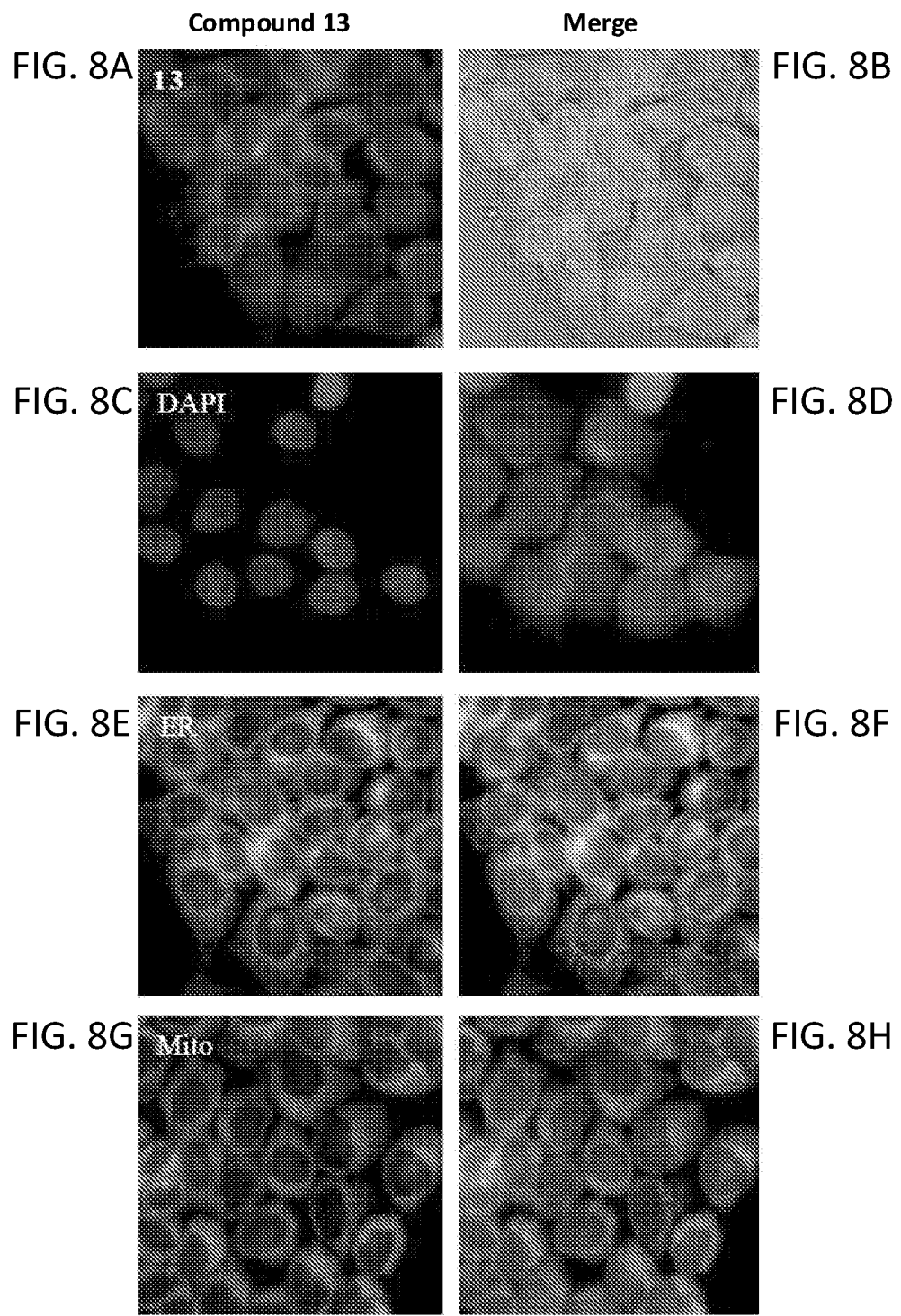

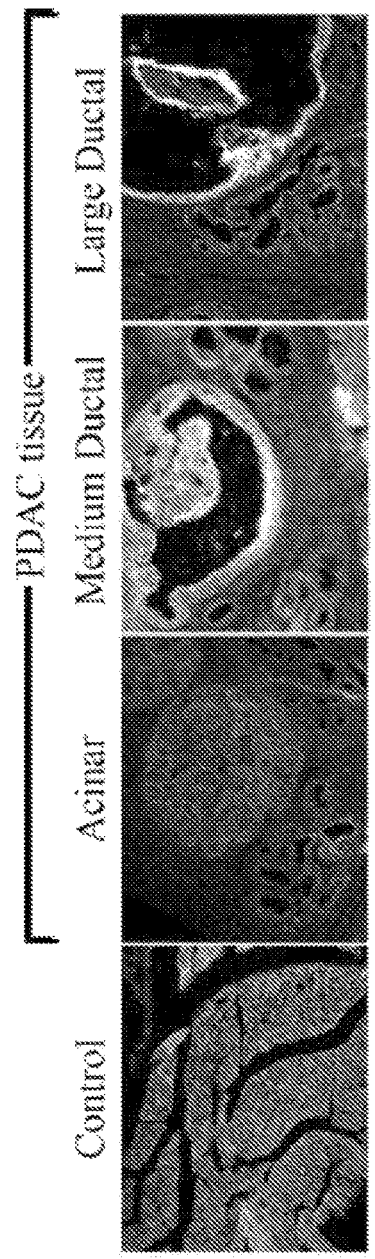
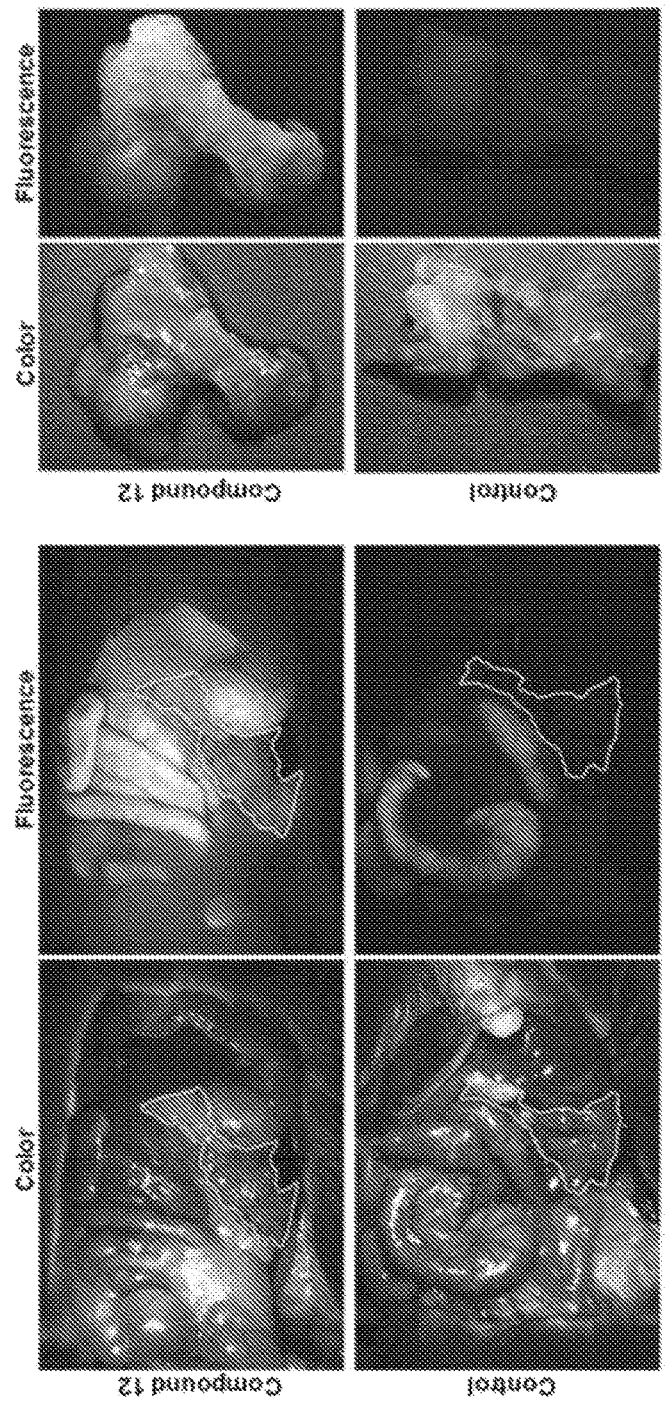
FIG. 12A
FIG. 12B
FIG. 12C

MOLECULAR PROBES FOR DETECTION AND IMAGING OF PANCREATIC CANCER

CROSS REFERENCE TO RELATED APPLICATIONS

This is the U.S. National Stage of International Application No. PCT/US2017/033961, filed May 23, 2017, which was published in English under PCT Article 21(2), which claims the benefit of U.S. Provisional Application No. 62/340,405, filed May 23, 2016, each of which is incorporated by reference herein in its entirety.

ACKNOWLEDGMENT OF GOVERNMENT SUPPORT

This invention was made with government support under EB016870 awarded by the National Institutes of Health. The government has certain rights in the invention.

FIELD

This disclosure concerns embodiments of fluorescent molecular probes useful for targeting and imaging pancreatic cancer.

BACKGROUND

Pancreatic ductal adenocarcinoma (PDAC) is one of the world's most lethal malignancies, with the poorest five-year survival rate of any cancer. There are no effective diagnostics or chemotherapeutics. Surgical resection is the only curative therapy; however, the majority of patients experience recurrence due largely to challenges in assessing tumor margin status in the operating room. Thus many patients are left with residual disease from margins not properly assessed, leading to early cancer recurrence following what was thought to be a potentially curative operation. The utilization of engineered antibodies can be a reasonable approach to improve surgical resection, as they can enable imaging probes to target cancer cells in vivo. However, antibody imaging probes share common disadvantages as compared to small organic fluorophores, such as their relatively long retention times in non-targeted tissues, slow clearance from circulation, and extensive condition optimization requirements. Furthermore, due to poor cell-membrane permeability, antibody-based imaging is limited in its applications to cell-surface biomarkers. Thus, molecular probes that selectively image pancreatic cancer tissue are urgently needed for therapeutic monitoring and/or image-guided surgery.

In addition to image-guided surgery, PDAC probes would be useful to facilitate early disease detection. The 5-year survival rate of patients with PDAC is <8%. Because most cases are diagnosed in the late stages, <15% of all patients have resectable tumors. However, early-stage PDAC surgery can result in 4 year survival rates of up to 78%. This has prompted the investigation of fluorescent probes for the ability to target PDAC as well as pancreatic intraepithelial neoplasia (PanIN), the lesions that occur in the pancreatic ducts that are preinvasive precursors of PDAC. In addition to pancreatic ductal epithelial cells, there is growing evidence that the transdifferentiation of alternative pancreatic cell types, such as acinar cells, embodies an alternative pathway to pancreatic adenocarcinoma.

SUMMARY

Fluorescent molecular probes for targeting and imaging pancreatic cancer are disclosed. Methods of making and using the probes are also disclosed.

The probe may have a chemical structure according to general formula I or a tautomer thereof:

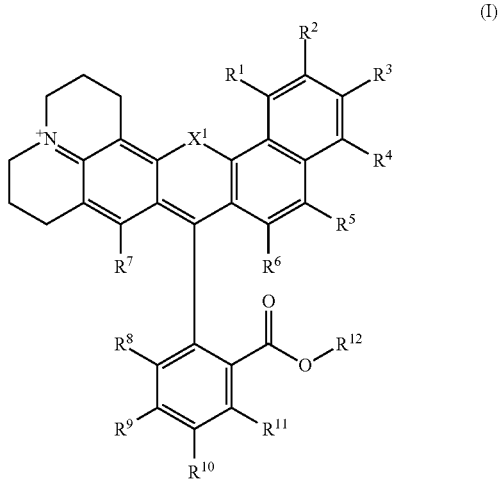

where $X^1$ is O, S, or N(H); $R^1$ is —OH, —NH$_2$, or —OR$^a$ wherein R$^a$ is lower alkyl; $R^2$-$R^7$ independently are H, hydroxyl, thiol, lower alkyl, carboxyalkyl, amino, alkoxy, or halogen; $R^8$-$R^{11}$ independently are H, alkyl, acyl, carboxyl, nitro, amino, substituted amino, or —SO$_3$H; and $R^{12}$ is H or lower alkyl. In some embodiments, $X^1$ is O.

In any or all of the above embodiments, $R^2$ may be lower alkyl, such as methyl. In any or all of the above embodiments, $R^2$-$R^{11}$ independently may be H or lower alkyl. In certain examples, $R^2$-$R^{11}$ are H.

In some embodiments, the probe has a chemical structure according to general formula II

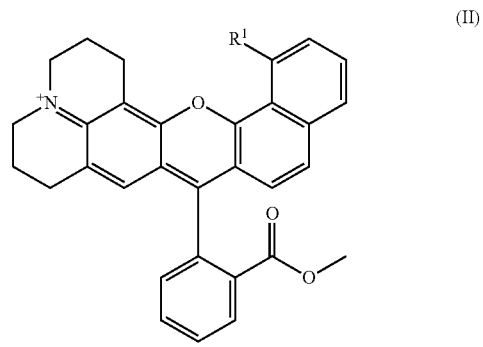

where $R^1$ is as previously defined. In certain embodiments, $R^1$ is —OCH$_3$ or —NH$_2$.

Embodiments of a method for detecting pancreatic cancer cells include contacting pancreatic tissue with a probe according to any of the foregoing embodiments or a probe according to structure 2

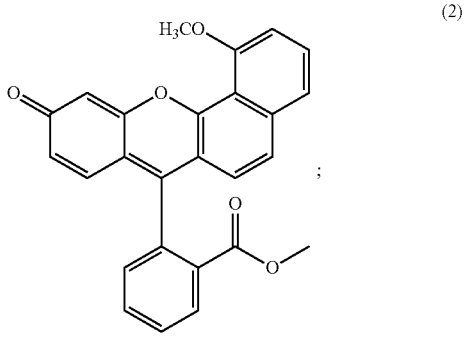 [SMILES: COC(=O)c1ccccc1-c1c2ccc(=O)cc-2oc2c1ccc1cccc(OC)c12]

(2)

and detecting pancreatic cancer cells by detecting fluorescence from the probe. Detecting fluorescence from the probe may comprise detecting fluorescence at a wavelength corresponding to an emission spectrum maximum of the probe. In any or all of the above embodiments, the pancreatic cancer cells may be pancreatic ductal adenocarcinoma cells or pancreatic intraepithelial neoplasia cells.

In any or all of the above embodiments, the pancreatic tissue may be contacted in vivo. In any or all of the above embodiments, contacting the pancreatic tissue may include administering the probe to a subject having or suspected of having pancreatic cancer, such by administering a composition comprising the probe and a pharmaceutically acceptable carrier. In any of the foregoing embodiments, the probe may be administered systemically, such as by intravascular administration. In any of the foregoing embodiments, the probe may be administered intraoperatively.

In some of the above embodiments, the pancreatic tissue is contacted with the probe ex vivo, e.g., in frozen tissue sections. In certain embodiments, detecting fluorescence from the probe is performed within 30 minutes of contacting the pancreatic tissue ex vivo with the probe.

In any or all of the above embodiments, the probe may be

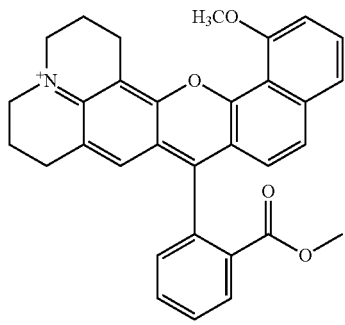

In such embodiments, detecting fluorescence from the probe may include exposing the pancreatic tissue to a light source providing light having a wavelength from 530-560 nm, and detecting fluorescence at a wavelength of from 570-640 nm.

The foregoing and other objects, features, and advantages of the invention will become more apparent from the following detailed description, which proceeds with reference to the accompanying figures.

BRIEF DESCRIPTION OF THE DRAWINGS

FIGS. 6A-6H are color photographs showing subcellular localization of compound 2: compound fluorescence (6A), phase contrast of compound 2 (6B), DAPI fluorescence (6C), composite of compound 2 and DAPI fluorescence (6D), ER-Tracker™ Green fluorescence (6E), composite of compound 2 and ER-Tracker™ Green fluorescence (6F), MitoTracker® Green fluorescence (6G), composite of compound 2 and MitoTracker® Green fluorescence (6H).

FIGS. 7A-7H are color photographs showing subcellular localization of compound 12: compound fluorescence (7A), phase contrast of compound 12 (7B), DAPI fluorescence (7C), composite of compound 12 and DAPI fluorescence (7D), ER-Tracker™ Green fluorescence (7E), composite of compound 12 and ER-Tracker™ Green fluorescence (7F), MitoTracker Green fluorescence (7G), composite of compound 12 and MitoTracker® Green fluorescence (7H).

FIGS. 8A-8H are color photographs showing subcellular localization of compound 13: compound fluorescence (8A), phase contrast of compound 13 (8B), DAPI fluorescence (8C), composite of compound 13 and DAPI fluorescence (8D), ER-Tracker™ Green fluorescence (8E), composite of compound 13 and ER-Tracker™ Green fluorescence (8F), MitoTracker® Green fluorescence (8G), composite of compound 13 and MitoTracker® Green fluorescence (8H).

FIGS. 12A-12C are photographs showing ex vivo microscopy images of control and PDAC tissue slides obtained from PDAC mice stained with compound 12 (12A), realtime intraoperative white light and fluorescence imaging of compound 12 in PDAC mice (12B), and macroscopic images of resected pancreas tissue from the PDAC mice ex vivo (12C).

DETAILED DESCRIPTION

Figure 1:
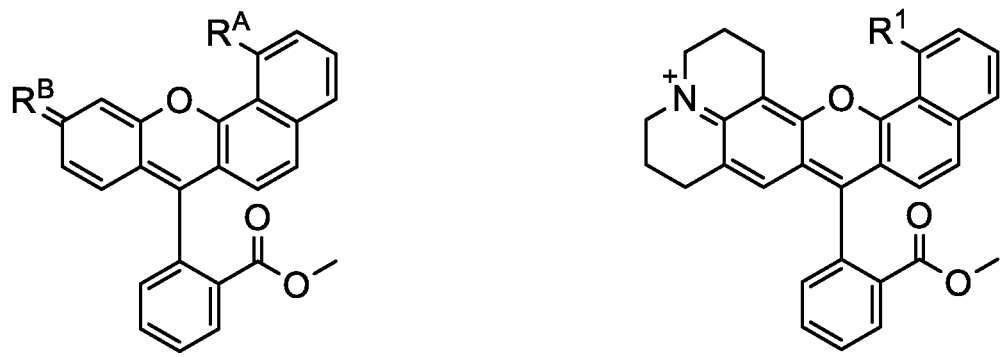
FIG. 1 shows chemical structures of exemplary fluorophores.

Fluorescent molecular probes for targeting and imaging pancreatic cancer are disclosed. Methods of making and using the probes are also disclosed. Embodiments of the disclosed probes inherently (i.e., without conjugation to a targeting agent) distribute in mouse model pancreas and accumulate in pancreatic ductal adenocarcinoma tumors selectively over surrounding healthy tissue, providing cancer-specific fluorescence. In contrast to other small molecule fluorophores, the disclosed probes do not require conjugation to biological targeting agents (such as antibodies, peptides, or peptidomimetics) while affording visualization of disease-related subcellular organelles, as well as the whole organ, resected tissues, and individual cells. Some embodiments of the disclosed probes also may be used to visualize a pancreas cell type associated with early onset of pancreatic cancer, such as pancreatic intraepithelial neoplasia cells. Embodiments of the disclosed probes are useful for pancreatic cancer early detection, therapeutic monitoring, and/or image-guided surgery.

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, wavelengths, and so forth, as used in the specification or claims are to be understood as being modified by the term "about." Accordingly, unless otherwise implicitly or explicitly indicated, or unless the context if properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Administering: Administration by any route, for example oral or parenteral administration to the subject. "Parenteral" administration is by any route other than through the alimentary tract and includes intravascular administration directly into a blood vessel (for example by intravenous or intra-arterial administration) or intraperitoneal administration. "Systemic" administration is by any route where the administered compound is distributed throughout a subject's body and includes intravascular administration.

Alkyl: A hydrocarbon group having a saturated carbon chain. The chain may be cyclic, branched or unbranched. The term lower alkyl means the chain includes 1-10 carbon atoms. Unless otherwise specified, an alkyl group may be substituted or unsubstituted.

Alkoxy: A functional group having the formula —OR where R is an alkyl group. The term lower alkoxy means that the alkyl group includes 1-10 carbon atoms.

Alkylamino: An alkyl group where at least one hydrogen is substituted with an amino, mono-substituted amino or di-substituted amino group.

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A substituted amino means at least one of R and R' is other than hydrogen.

Carboxyalkyl: A group having a general formula —C(O)OR, where R is an alkyl group.

Carboxyl: A —COOH radical.

Detect: To determine if an agent (such as a target molecule) is present or absent, for example, in a sample. "Detecting" refers to any method of determining if something exists, or does not exist, such as determining if a target cell (e.g., a cancer cell) is present in a biological sample. For example, "detecting" can include using a visual or a mechanical device to determine if a sample displays a specific characteristic.

Emission or emission signal: The light of a particular wavelength generated from a source. In particular examples, an emission signal is emitted from a fluorophore after the fluorophore absorbs light at its excitation wavelength(s).

Fluorescence: The emission of visible radiation by an atom or molecule passing from a higher to a lower electronic state, wherein the time interval between absorption and emission of energy is 10⁻⁸ to 10⁻³ second. Fluorescence occurs when the atom or molecule absorbs energy from an excitation source (e.g., an ultraviolet lamp) and then emits the energy as visible radiation.

Fluorophore: A compound capable of fluorescence, such as a fluorescent dye. The term "fluorophore" also refers to the portion of a molecule that causes the molecule to fluoresce when exposed to an excitation source.

PDAC: pancreatic ductal adenocarcinoma

Pharmaceutically acceptable carrier: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the compounds herein disclosed. In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected effective dosage of the active agent, for example in a vial, bottle, or syringe.

Probe: As used herein, the term "probe" refers to a molecule, such as a fluorophore, capable of selectively being taken up by a cell or tissue of interest and producing a detectable signal. A detectable signal may include an emission signal is emitted from a fluorophore after the fluorophore absorbs light at its excitation wavelength(s).

SBR: Signal-to-background ratio.

Subject: An animal or human subjected to a treatment, observation or experiment.

Tautomers: Constitutional isomers of organic compounds that differ only in the position of the protons and electrons, and are interconvertible by migration of a hydrogen atom. Tautomers ordinarily exist together in equilibrium.

Thiol: A functional group having the formula —SH.

II. Probes

One of the main challenges in PDAC therapy is drug delivery, and is largely attributed to the hypovascular and fibrotic tumor microenvironment. Disclosed herein are embodiments of fluorescent probes having suitable physicochemical properties for uptake by pancreatic cancer cells, such as PDAC cells, thereby overcoming the problem of drug delivery. Probe size, lipophilicity, solubility, and ionization state are key factors that modulate in vivo biodistribution. Exemplary probes are modified benzoxanthene fluorophores (FIG. 1). To minimize autofluorescence, the probes were designed to exhibit significant bathochromic shifts, via the repositioning of their polar groups, as compared to traditional long-wavelength benzoxanthenes. Advanta-geously, the disclosed probes do not require conjugation to biological targeting agents for cancer specificity. Some embodiments of the probes are also useful for visualizing subcellular organelles within cancer cells.

Some embodiments of the disclosed molecular probes have a general formula I:

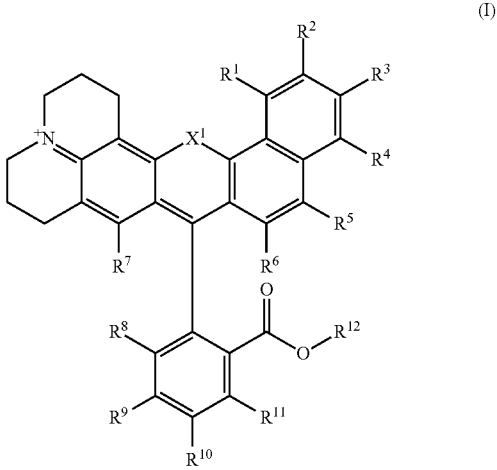

(I)

where $X^1$ is O, S, or N(H); $R^1$ is —OH, —NH$_2$, or —OR$^a$ wherein $R^a$ is lower alkyl; $R^2$-$R^7$ independently are H, hydroxyl, thiol, lower alkyl, carboxyalkyl, amino, alkoxy, or halogen; $R^8$-$R^{11}$ independently are H, alkyl, acyl, carboxyl, nitro, amino, substituted amino (e.g., alkyl-substituted amino, such as —N(CH$_3$)$_2$), or —SO$_3$H; and $R^{12}$ is H or lower alkyl. In some embodiments, $X^1$ is O. In certain embodiments, $R^2$ is lower alkyl, such as $C_1$-$C_3$ alkyl. In some instances, $R^{12}$ is methyl. In any of the foregoing embodiments, $R^2$-$R^{11}$ independently may be H or lower alkyl. In certain embodiments, $R^2$-$R^{11}$ are H. Tautomers of the molecular probes according to general formula I are also a part of this disclosure.

In an independent embodiment, $X^1$ is O, $R^1$ is —OH, —NH$_2$, or —OR$^a$ wherein $R^a$ is lower alkyl, $R^2$-$R^{11}$ are H, and $R^{12}$ is lower alkyl. In another independent embodiment, $X^1$ is O, $R^1$ is —OH, —NH$_2$, or —OCH$_3$, $R^2$-$R^{11}$ are H, and $R^{12}$ is methyl.

In some embodiments, the probes have a general formula II:

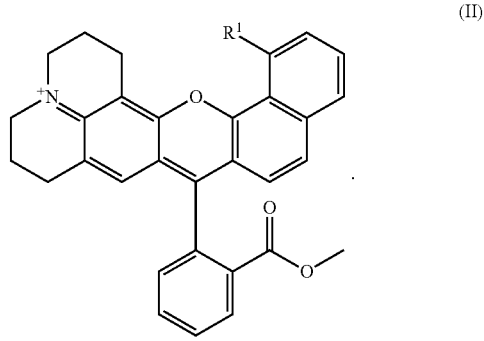

(II)

where $R^1$ is —OH, —NH$_2$, or —OR$^a$ wherein $R^a$ is lower alkyl, e.g., $C_1$-$C_3$ alkyl. In certain embodiments, the probe is compound 11, compound 12, or compound 13:

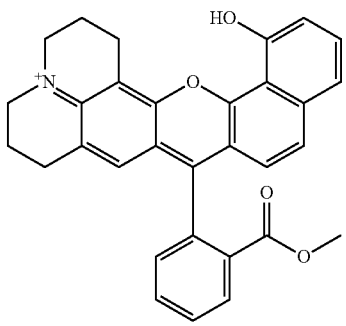

11

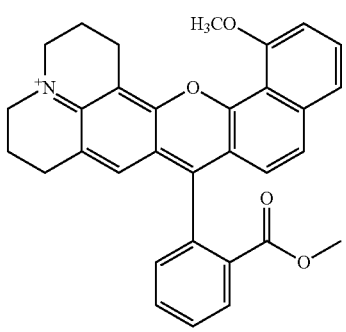

12

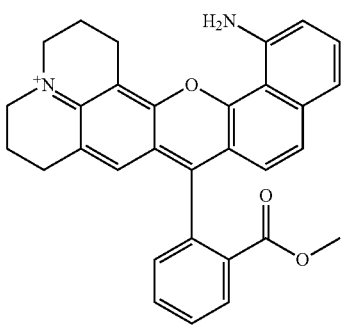

13

Some of the compounds are capable of tautomerization under at least some solvent and/or pH conditions. For example, compound 11 exhibits the following tautomerization equilibrium:

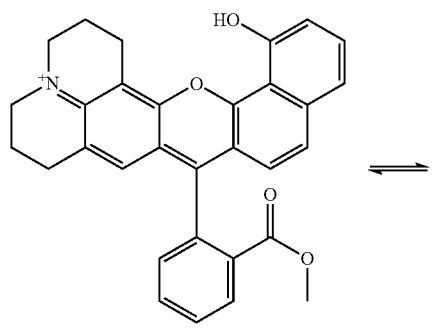

11

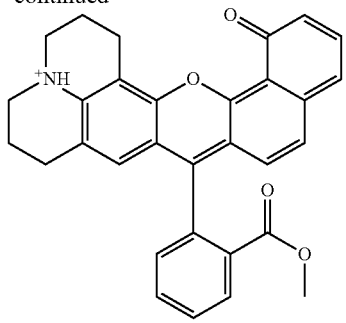

In aqueous solution at low pH, the tautomer with a hydroxyl group on the annulated ring dominates. In organic solvents, both tautomers are apparent. Compounds 1-6, 11, and 12 (FIG. 1) tautomerize. The methyl ether derivatives 2, 4, 6, and 12 approximate naphthol tautomers and exist as single species in organic solvents, similar to short wavelength tautomers of compounds 1, 3, 5, and 11.

III. Methods of Use

Embodiments of the disclosed probes inherently accumulate in pancreatic cancer cells, such as pancreatic ductal adenocarcinoma tissue. Accordingly, the probes may be administered intraoperatively for image-guided surgery and resection of pancreatic cancers, such as PDAC. Some embodiments of the disclosed probes also accumulate in pancreatic adenocarcinoma mouse model acinar cells. The probes may be used to facilitate early detection of pancreatic carcinoma, e.g., via fluorescent imaging. The probes are also useful for therapeutic monitoring and/or image-guided surgery. Certain embodiments of the disclosed probes enable imaging at the level of the whole organ, tissue, cell, and/or organelle. At an intracellular level, some embodiments of the disclosed probes (e.g., compounds 12 and 13) preferentially target mitochondria in PDAC cells. Mitochondrial dysfunction is central to the pathogenesis of PDAC.

Embodiments of a method for detecting pancreatic cancer cells include contacting pancreatic tissue with a probe as disclosed herein, and detecting pancreatic cancer cells by detecting fluorescence from the probe. Fluorescence may be detected by exposing the pancreatic tissue to a light source providing light at a wavelength corresponding to an excitation wavelength of the probe and detecting fluorescence emitted by the probe, e.g., by detecting fluorescence at a wavelength corresponding to an emission spectrum maximum of the probe.

Pancreatic tissue may be contacted with the probe ex vivo or in vivo. For example, a pancreatic tissue biopsy may be contacted with the probe ex vivo. In some embodiments, pancreatic tissue is contacted with the probe in vivo.

Pancreatic tissue may be contacted in vivo by administering the probe to a live subject having or suspected of having pancreatic cancer. The subject may be a non-human animal or a human. The probe may be administered by administering a composition comprising the probe and a pharmaceutically acceptable carrier to the subject. In some embodiments, the probe or the composition comprising the probe is administered parenterally to the subject. Parenteral administration may be systemic or by intraperitoneal administration. Suitable systemic routes of administration include intravascular administration, such as by intravenous injection. In some embodiments, the probe or the composition comprising the probe is administered to the subject intraoperatively. Imaging may be performed after waiting an effective amount of time for the compound to be taken up by pancreatic cancer cells. In some instances, the effective amount of time includes sufficient time for the compound to be taken up by the cancer cells and sufficient time for the compound to be cleared from noncancerous tissues. Uptake by pancreatic cancer cells begins within minutes of administration, such as within 5 minutes of administration. Initially, the compound may also be taken up by other abdominal organs, such as by the bladder, intestines, kidney, liver, spleen, and stomach, as well as by adipose tissue. However, the compound subsequently is cleared from noncancerous tissue, such as via renal or hepatic clearance. Thus, the effective amount of time prior to imaging may include sufficient time for clearance from tissues other than pancreatic cancer tissue. Imaging may be performed, for example, 3-5 hours after administration of the compound so that fluorescence from noncancerous pancreatic tissue and/or fluorescence in surrounding organs is diminished relative to fluorescence from the pancreatic cancer tissue. In some embodiments, the effective period of time is from several minutes to several hours, such as from 5 minutes to 12 hours, such as from 15 minutes to 6 hours, from 30 minutes to five hours, from 1-5 hours, from 1-4 hours, from 1-3 hours, from 1-2 hours.

When a pancreatic tissue biopsy is contacted with the probe ex vivo, e.g., in frozen tissue section, the effective amount of time for the probe to be taken up by the cells may be less than one hour. In some embodiments, imaging may be performed within 60 minutes, within 45 minutes, or within 30 minutes after contacting the tissue section with the probe. For example, imaging may be performed 1-60 minutes, 1-45 minutes, 1-30 minutes, 5-30 minutes, 10-30 minutes, or 15-30 minutes after contacting the tissue section with the probe.

In one embodiment, the probe is compound 2:

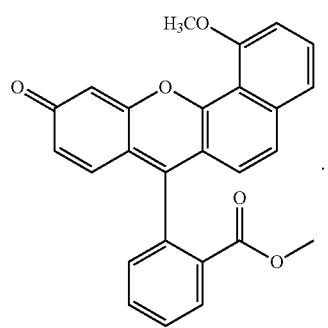

Presence of compound 2 in pancreatic tissue may be detected by exposing the pancreatic tissue to a light source providing light having a wavelength from 530-560 nm, and detecting fluorescence at a wavelength of from 570-640 nm.

In an independent embodiment, the probe is compound 12:

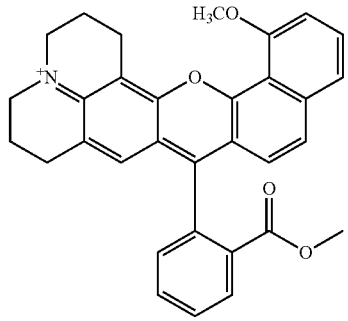

Presence of compound 12 in pancreatic tissue may be detected by exposing the pancreatic tissue to a light source providing light having a wavelength from 530-560 nm, and detecting fluorescence at a wavelength of from 570-640 nm.

In another independent embodiment, the probe is compound 13:

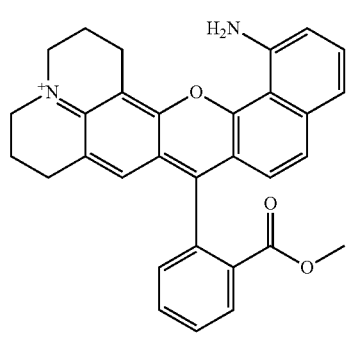

Presence of compound 13 in pancreatic tissue may be detected by exposing the pancreatic tissue to a light source providing light having a wavelength from 590-650 nm, and detecting fluorescence at a wavelength of from 660-740 nm.

Image-guided surgery using the disclosed probes may be performed to facilitate visualization and excision of malignant tissue from a subject. In some embodiments, images are obtained intraoperatively. In an independent embodiment, the probes may be used for therapeutic monitoring of a subject. For example, a subject may be administered a probe as disclosed herein at periodic intervals (e.g., intervals of a few weeks to a few months, or even intervals of a year or more) and then imaged by detecting fluorescence from the probe in vivo to assess whether cancerous pancreatic tissue is present, and/or whether a malignancy is growing in size and/or metastasizing.

IV. EXAMPLES

General Methods

Physiochemical property prediction and molecular modeling. Physicochemical partition coefficient, log D value at pH 7.4, was calculated using Marvin and JChem calculator plugins (ChemAxon, Budapest, Hungary). Molecular orbital, UV-Vis spectra and electrostatic maps calculations were performed using the Density Functional Theory (DFT) modeling on the gas-phase B3LYP/6-31G optimized geometries using Gaussian 09.

UV-Vis absorption and fluorescence spectroscopy. UV-Vis spectra were collected with a Cary 50 UV-Vis spectrophotometer at room temperature, using a 1-cm quartz cuvette. Fluorescence spectra were collected on a Cary Eclipse fluorescence spectrophotometer (Agilent Technologies). All absorbance spectra were reference corrected. Fluorescence spectra were corrected for the wavelength dependent response of the R928 photomultiplier tube using a manufacturer generated correction file. Quantum yields are reported as the average of multiple measurements using multiple references. Excitation emission matrices (EEMs) were collected over various spectral regions, using 5-nm step sizes for emission and 10-nm step sizes for excitation. The band pass for excitation and emission was 5 to 10 nm.

Cell culture. The human PDAC cell line Capan-1 was obtained from Dr. Rosalie Sears' laboratory and maintained in RPMI medium (Gibco) in a humid atmosphere at 37° C. with 5% $CO_2$. All media were supplemented with 10% (v/v) fetal bovine serum (FBS), and 1% (v/v) penicillin/streptomycin. The cell viability was determined by Cell Titer-Blue® assay (Promega Corporation). Monolayers of $10^4$ Capan-1 cells were seeded in triplicate in 96 well plates and incubated with decreasing concentration from 100 µM of each compound in growth media containing 10% FBS. After 24 h incubation time, 20 µL of CellTiter-Blue® reagent was added into each well, and culture cells were incubated for additional 2 h. Fluorescence intensity in each well was recorded at 560/590 nm in a SpectraMax® M5 Microplate Reader (Molecular Devices, LLC). The half maximal inhibitory concentration ($IC_{50}$) of these three compounds were determined from interpolating values in the graph (% cell viability vs. fluorophore concentration). For comparison of cellular uptake rate in Capan-1 cells, absorbance of media was measured as background, and absorbance of supernatant was obtained to determine the cellular uptake by using absorbance of 10 µM fluorophore in cell free media as standard reference.

In vitro live cell imaging. Monolayers of $10^4$ Capan-1 cells were seeded in triplicate in 8 well plates and incubated for 24 h in growth media containing 10% FBS and allowed to attach. For subcellular colocalization experiments, media was extracted and cells were washed with PBS, and phenol red-free growth medium was added to each well. Organelle trackers were added to each well, and incubated with the compound (final concentration 0.5 µM) of interest for 1 h. Cells were then washed with PBS and then fixed with 2% paraformaldehyde (PFA). Fluorescence microscopy was carried out using a Zeiss inverted microscope with an Axioscan fluorescence camera for imaging. Final concentration of organelle trackers used in this experiments, DAPI (4,6-diamidino-2-phenylindole) 0.5 µM, MitoTracker® Green (benzoxazolium 2-[3-[5,6-dichloro-1,3-bis[[4-(chloromethyl)-phenyl]methyl]-1,3-dihydro-2H-benzimidazol-2-ylidene]-1-propenyl]-3-methyl-chloride 201860-17-5v, ThermoFisher Scientific) 0.5 µM, and ER-Tracker™ Green (BODIPY® FL dye and glibenclamide; ThermoFisher Scientific) 1 µM.

Animals. Approval for the use of all animals in this study was obtained from the Institutional Animal Care and Use Committee (IACUC) at Oregon Health and Science University (OHSU). Male CD-1 mice weighing 22-24 g were purchased from Charles River Laboratories (Wilmington, MA). Genetically engineering mouse models of PDAC based on the targeted expression of an oncogenic KRAS mutation (KRASG12D) in the mouse pancreas were used to model the human disease. Mice expressing the KRAS mutation alone, termed "KC mice", develop the full range of intraductal neoplastic lesions (PanINs) that are histologically indistinguishable from human PanINs. The mice develop PanINs with 100% penetrance, but these lesions do not progress to metastatic disease (Hingorani et al., *Cancer Cell* 2003, 4: 437-450; Tuveson et al., *Cold Spring Harbor Symp. Quant boil.* 2005, 70: 65-72). A modification of the KC mouse that was developed in the laboratory of Dr. Rosalie Sears (Department of Molecular & Medical Genetics, Oregon Health and Science University) was used to more closely model human PDAC. This mouse model, termed "KMC mice", included overexpression of the wild-type Myc oncogene (Jackson et al., *Genes Dev.* 2001, 15: 3243-3248; Kawaguchi et al., *Nat. Genet.* 2002, 32: 128-134), similar to their previously published breast cancer mouse models (Wang et al., *Cancer Res.* 2011, 71: 925-936). This pancreatic cancer mouse model developed PanIN lesions by 10 weeks of age and rapidly progressed to PDAC including metastatic disease, more closely representing the human disease (Sears Lab OHSU, unpublished data). Both KC and KMC mice were used to assess compound 12 accumulation in PDAC. All animals were placed on 5V75 chlorophyll free diet from TestDiet (St. Louis, Mo.) 1 week prior to any imaging studies. Prior to surgery, mice were anaesthetized with 100 mg/kg ketamine and 10 mg/kg xylazine (Patterson Veterinary, Devens, Mass.). The peritoneal cavity was surgically exposed by removal of overlaying skin and muscle tissue to image fluorophore biodistribution following intravenous injection.

Intraoperative fluorescence imaging system. In vivo murine biodistribution images and macroscopic images of resected tissues were acquired using a custom-built small animal imaging system capable of real time color and fluorescence imaging. The imaging system consists of a QImaging EXi Blue monochrome camera (Surrey, British Columbia, Calif.) for fluorescence detection with a removable Bayer filter for collecting co-registered color and fluorescence images. A PhotoFluor II light source (89 North, Burlington, Vt.) was focused onto the surgical field through a liquid light guide and used unfiltered for white light illumination. For fluorescence detection, the light source was filtered with a 545±12.5 nm, 620±30 nm, or a 650±22.5 nm bandpass excitation filter for Compound 2 and 12, Compound 13, and Methylene Blue (MB) fluorescence excitation, respectively. Resulting fluorescence was collected with a 605±35 nm, 700±37.5 nm, or 720±30 nm bandpass emission filter for Compound 2 and 12, Compound 13, and MB image collection, respectively. All filters were obtained from Chroma technology (Bellows Falls, Vt.). Camera exposure times ranged from 50 to 200 ms for fluorescence image collection. All images collected for comparison between treatment groups were acquired with the same exposure time and are displayed under equal normalized brightness and contrast levels where indicated.

Systemic administration of fluorescent compounds. For initial in vivo testing and biodistribution studies 100 nmol of compounds 2, 12, and 13 were injected systemically. Fluorophores were diluted in PBS. For comparison with previous studies, 120 nmol Methylene Blue was injected systemically. Mice were administered blank PBS for control images (n=3 mice per group, 5 groups). For PDAC tumor mice model testing 100 nmol of Compound 12 was injected systemically (n=5 mice).

In vivo biodistribution imaging. The biodistribution of compounds 2, 12, and 13 was assessed using the intraoperative fluorescence imaging system to collect images of the peritoneal cavity. The peritoneal cavity was exposed and images were collected so that the bladder, adipose tissue, intestine, kidney, liver, muscle, pancreas, spleen, and stomach were visible within the field of view. For initial biodistribution studies images were collected immediately after injection and at 5, 15, 30, 60, 120, and 240 min following injection. For MB injected mice, images were collected on the same time course, but only out to 60 min due to the rapid clearance of MB. For PDAC tumor bearing mice, images were collected immediately after injection and at 5, 15, 30, 60, and 90 min following injection. Vehicle injected control animals were imaged on the same time course as fluorophore injected animals for initial testing or immediately following injection only for studies involving MB or PDAC tumor bearing mice to assess tissue autofluorescence for comparison to injected animals.

Fluorophore biodistribution kinetics were measured using region of interest analysis on images collected of the peritoneal cavity. Mean fluorescence intensities in each organ or tissue type were measured from images collected at each time point. All intensities were normalized to the muscle intensity at that time point by dividing by the measured muscle intensity. Using the normalized fluorescence intensities for each organ or tissue type, mean intensities were calculated for each group.

Upon completion of initial biodistribution studies, animals were euthanized and their organs were resected. Macroscopic images of the resected organs were collected using the intraoperative fluorescence imaging system and the mean fluorescence intensity of each resected organ was measured using region of interest analysis. Fluorescence intensities were normalized to the muscle intensity in the same manner as in vivo measurements. Mean intensities were calculated for each group using the normalized values. For biodistribution studies in PDAC tumor bearing mice, only the pancreas was resected and imaged following euthanasia.

Ex vivo fluorescence microscopy, pathology, and immunofluorescence staining. Resected pancreas tissue from compound 12 in vivo biodistribution studies with PDAC tumor bearing mice was fixed with 2% PFA for 12 h, flash frozen in optimal cutting temperature (OCT) compound with liquid nitrogen, and stored at −80° C. Cryosections were cut at 10 μm onto Superfrost Plus slides (Fisherbrand, Fisher Scientific). Slides were mounted with Fluoromount-G (Southern Biotech, Birmingham, Ala.) and coverslipped. Serial sections were obtained for cytokeratin immunofluorescence microscopy enabling imaging of compound 12 and immunofluorescence labeling with 0.01 mg/mL of directly labeled anti-pan cytokeratin conjugated to AlexaFluor 488 (eBioscience, San Diego, Calif.). Briefly, slides were rinsed with PBS for 2 min to remove residual OCT. Then, slides were fixed by immersion in 2% PFA for 15 min and washed with PBS for 5 min three times. Primary antibody was incubated on the slides for 1 h at room temperature. Following incubation, slides were washed with PBS three times for 5 min each and then post-fixed with PFA for 15 min and washed with PBS once for 5 min before mounting with Fluoromount-G. For cytokeratin immunofluorescence controls, serial sections were stained using the above immunofluorescence procedure but without antibody present in the staining solution that was incubated on the slides. For H&E pathological analysis, slides previously stained for cytokeratin expression were unmounted and rinsed with PBS to remove residual mounting media prior to H&E staining. Images were acquired on an Axio Observer inverted fluorescence microscope (Zeiss, Thornwood, N.Y.) at 10, 20, or 40× magnification. A PhotoFluor II was used unfiltered for H&E color images and filtered using a 545±12.5 nm or 470±20 nm bandpass excitation filter for compound 12 or Atto 488 excitation, respectively. Color images were collected using an Axiocam 105 camera (Zeiss) and fluorescence images were collected using an Axiocam 506 camera (Zeiss) where a 605±35 nm or 525±25 nm bandpass emission filter was used for compound 12 or Atto 488 fluorescence image collection, respectively.

Example 1

Compound Synthesis

As described in detail below, seminaphthofluorescein, rhodafluors and rhodamine analogues (FIG. 1) were synthesized in two or three steps. The initial step involved the condensation of hydroxybenzophenones with the corresponding naphthols in a mixture of $CH_3SO_3H$:TFA 1:1 at 80° C. for 16-24 h to produce the corresponding lactones or carboxylates. Subsequent Fisher esterification, to produce the methyl esters derivatives was carried out in MeOH catalyzed by either $H_2SO_4$ or HCl. Further alkylation was furnished by treatment of either the carboxylate or methyl ester intermediate with methyl iodide in the presence of $K_2CO_3$ in DMF to produce the corresponding methyl ethers. The starting materials; 2-(2,4-dihydroxybenzoyl)benzoic acid, 2-(4-amino-2-hydroxybenzoyl)benzoic acid, 2-(8-hydroxy-1,2,3,5,6,7-hexahydropyrido[3,2,1-ij]quinoline-9-carbonyl)benzoic acid and 1,8-naphthalene derivatives were synthesized according to described or modified literature protocols.

General. Unless otherwise indicated, all commercially available starting materials were used directly without further purification. Silica gel Sorbent Technologies 32-63 μm was used for flash column chromatography. $^1$H- and $^{13}$C NMR were obtained on either a ARX-400 or ARX 600 Advance Bruker spectrometer. Chemical shifts (δ) are given in ppm relative to $d_6$-DMSO (2.50 ppm, $^1$H, 39.52 $^{13}$C) unless otherwise indicated. MS (HRMS, ESI) spectra were obtained at the PSU Bioanalytical Mass Spectrometry Facility on a ThermoElectron LTQ-Orbitrap high resolution mass spectrometer with a dedicated Accela HPLC system. Compounds 1 and 2 were synthesized as described in the literature.

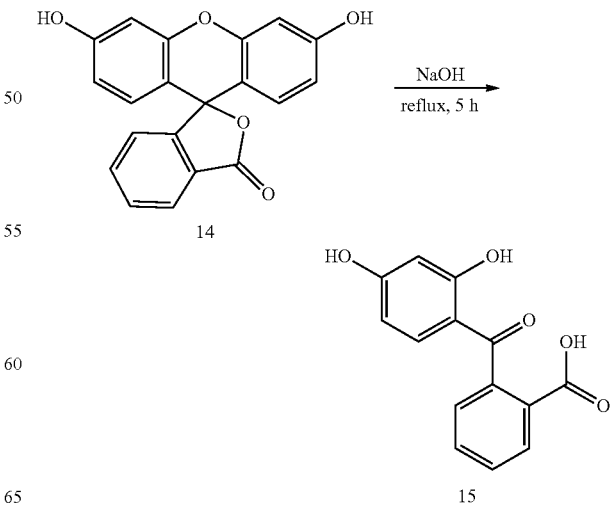

Synthesis of 2-(2,4-dihydroxybenzoyl)benzoic acid, 15. NaOH (50 g, 1.25 mol) was dissolved in 100 mL of DI water while cooling in an ice bath. Fluorescein (14) was added in one portion and the mixture was refluxed 5 h. The mixture was cooled down to room temperature and neutralized to pH 7 using concentrated HCl. The mixture was treated with 2% NaHCO$_3$ to dissolve the solid formed, and then extracted with ethyl ether (3×100 mL). The aqueous phase was acidified to pH 2 using concentrated HCl, then extracted with ethyl ether (300 mL). The ethyl ether was evaporated under vacuum to leave a brown residue. The target compound 15 was isolated by recrystallization from water. Yield: 4.35 g, 56%. $^1$H NMR (400 MHz, DMSO) δ13.19 (s, 1H), 12.24 (s, 1H), 10.71 (s, 1H), 8.00 (dd, J=7.7, 0.9 Hz, 1H), 7.74-7.67 (m, 1H), 7.65-7.61 (m, 1H), 7.42 (dd, J=7.5, 1.0 Hz, 1H), 6.95-6.90 (m, 1H), 6.33 (d, J=2.3 Hz, 1H), 6.29 (dd, J=8.7, 2.3 Hz, 1H). $^{13}$C NMR (101 MHz, DMSO) δ200.51, 166.76, 165.01, 164.42, 140.00, 134.75, 132.32, 129.99, 129.74, 129.48, 127.45, 113.29, 108.34, 102.55. HR ESI [M+H]$^+$ m/z 259.0602, calc. for C$_{14}$H$_{11}$O$_5$ 259.0600.

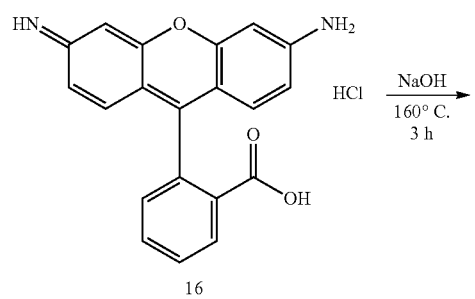

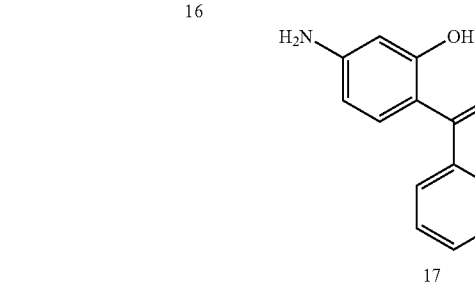

Synthesis of 2-(4-amino-2-hydroxybenzoyl)benzoic acid, 17. Rhodamine 110 hydrochloride (16) (0.2 g, 0.545 mmol) was mixed with NaOH (0.375 g, 9.27 mmol) and 180 µL of water. The mixture was stirred and heated at 160° C. for 2 h, 0.5 mL of 50% NaOH was added in one portion, and the mixture was heated and stirred at 160° C. for an additional 1 h. The mixture was allowed to cool down to room temperature and diluted with 10 mL of water. The mixture was acidified to pH 1 with concentrated HCl. The resulting mixture was extracted with ethyl ether (2×50 mL), the organic extracts were combined, dried over anhydrous Na$_2$SO$_4$, filtered and the solvent evaporated under vacuum to leave 17 as a pale yellow solid. Yield: 0.130 g, 93%. $^1$H NMR (400 MHz, DMSO) δ13.01 (s, 1H), 12.59 (s, 1H), 7.95 (dd, J=7.7, 1.0 Hz, 1H), 7.67 (td, J=7.5, 1.4 Hz, 1H), 7.60 (td, J=7.6, 1.4 Hz, 1H), 7.36 (dd, J=7.5, 1.0 Hz, 1H), 6.71 (d, J=8.6 Hz, 1H), 6.44 (s, 2H), 6.05-5.97 (m, 2H). $^{13}$C NMR (101 MHz, DMSO) δ198.31, 166.92, 164.98, 156.82, 140.07, 134.48, 131.95, 129.84, 129.69, 129.31, 127.68, 109.79, 106.48, 98.16. HR ESI [M+H]$^+$ m/z 258.0754, calc for C$_{14}$H$_{12}$NO$_4$ 258.0760; HR ESI [M+Na]$^+$ m/z 280.0575, calc. for C$_{14}$H$_{11}$NO$_4$Na$^+$ 280.0580.

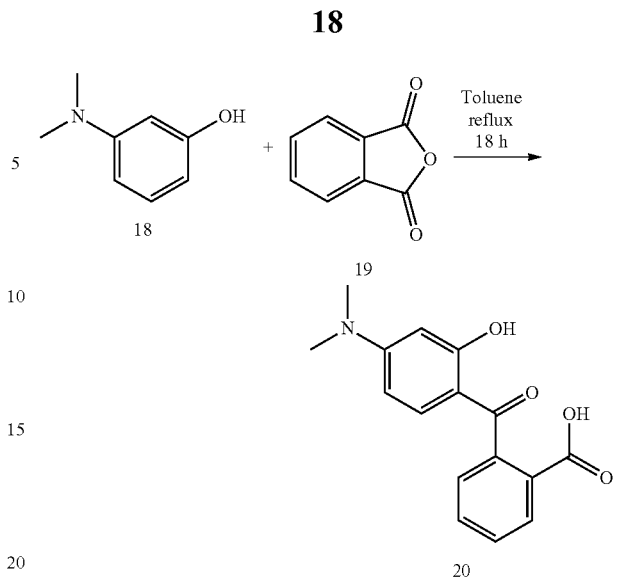

Synthesis of 2-(4-(dimethylamino)-2-hydroxybenzoyl)benzoic acid, 20. 3-dimethyl amino phenol (18) (5 g, 36.44 mmol) and phthalic anhydride (19) (5.39 g, 36.44 mmol) are dissolved in 150 mL of toluene and refluxed 18 h. The solvent is evaporated under vacuum to leave a purple residue. The residue is dissolved in ethyl acetate and the mixture passed through a plug of silica gel using EtOAc:Hexanes 1:1, EtOAc:Hexanes 3:1, and EtOAc for elution; 4.32 g, 42% of 20 are obtained. $^1$H NMR (400 MHz, CDCl$_3$) δ12.51 (s, 1H), 8.09 (dd, J=7.9, 0.9 Hz, 1H), 7.66-7.59 (m, 1H), 7.53 (td, J=7.7, 1.3 Hz, 1H), 7.35 (dd, J=7.5, 0.9 Hz, 1H), 6.88 (d, J=9.1 Hz, 1H), 6.15 (d, J=2.5 Hz, 1H), 6.06 (dd, J=9.1, 2.5 Hz, 1H), 3.02 (s, 6H). $^{13}$C NMR (101 MHz, CDCl$_3$) δ198.78, 170.69, 165.29, 156.10, 141.35, 134.44, 132.96, 131.23, 129.34, 128.15, 127.81, 110.45, 104.13, 97.89, 40.09. HR ESI [M+H]$^+$ m/z 286.1094, calc for C$_{16}$H$_{16}$NO$_4$ 286.1073; HR ESI [M+Na]$^+$ m/z 308.0915, calc. for C$_{16}$H$_{15}$NO$_4$Na$^+$ 308.0893.

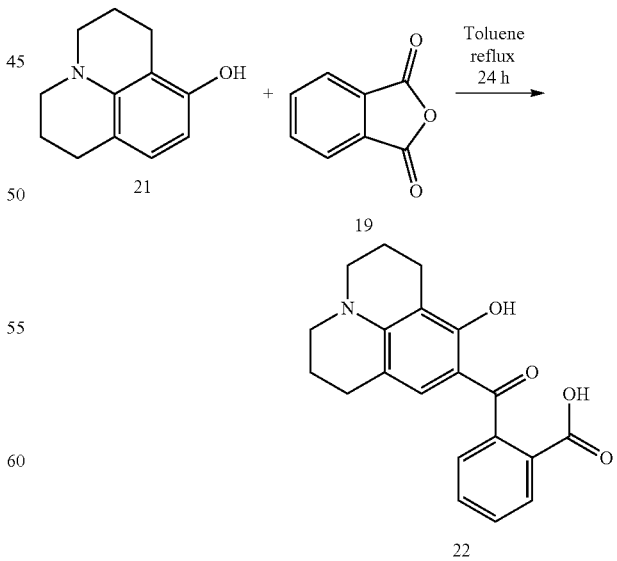

Synthesis of 2-(8-hydroxy-2,3,6,7-tetrahydro-1H,5H-pyrido[3,2,1-ij]quinoline-9-carbonyl)benzoic acid; 22.

Phthalic anhydride (19) (0.392 g, 2.64 mmol) and 8-hydroxyjulolidine (21) (0.5 g, 2.64 mmol) were dissolved in 12 mL of toluene. The mixture was refluxed 24 h, then the solvent evaporated under vacuum. The target compound 22 was isolated as a pale yellow solid by flash column chromatography on silica gel using $CH_2Cl_2$:MeOH 95:5 for elution. Yield: 622 mg, 70%. $^1$H NMR (400 MHz, DMSO) δ13.02 (s, 1H), 12.94 (s, 1H), 7.97-7.91 (m, 1H), 7.65 (dt, J=7.5, 3.8 Hz, 1H), 7.59 (dt, J=7.6, 3.8 Hz, 1H), 7.33 (d, J=6.5 Hz, 1H), 6.39 (s, 1H), 3.24 (dd, J=11.6, 7.0 Hz, 4H), 2.59 (t, J=6.4 Hz, 2H), 2.41 (t, J=6.1 Hz, 2H), 1.90-1.80 (m, 2H), 1.81-1.70 (m, 2H). $^{13}$C NMR (101 MHz, DMSO) δ197.98, 167.04, 159.77, 148.79, 140.16, 131.76, 129.85, 129.66, 129.19, 127.70, 112.43, 108.38, 104.61, 54.91, 49.39, 48.94, 26.66, 21.09, 20.09, 19.57. HR ESI [M+H]$^+$ m/z 338.1379, calc. for $C_{20}H_{20}NO_4$ 338.1386; HR ESI [M+Na]$^+$ m/z 360.1197, calc. for $C_{20}H_{19}NO_4Na^+$ 360.1206.

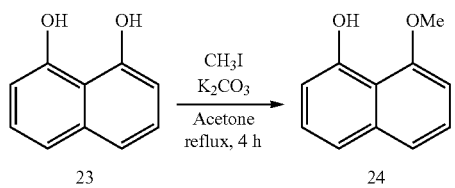 [SMILES: Oc1cccc2cccc(O)c12 ; COc1cccc2cccc(O)c12]

Synthesis of 8-methoxynaphthalen-1-ol; 24. Under Ar atmosphere 1,8-dihydroxynaphthalene (23) (1 g, 6.24 mmol) and ground $K_2CO_3$ were suspended in 5 mL of acetone, $CH_3I$ (0.88 g, 6.24 mmol) was added in one portion. The mixture was refluxed for 4 h. The mixture was allowed to cool down to room temperature, diluted with 15 mL of DI water and then acidified to pH 1 using 6 M HCl. The aqueous phase was extracted with ethyl acetate (2×50 mL). The organic extracts were combined, dried over anhydrous $Na_2SO_4$, filtered and the solvent evaporated under vacuum. The target compound 24 was isolated by flash column chromatography on silica gel using EtOAc:Hexanes 25:75 for elution. Yield: 0.86 g, 79%. $^1$H NMR (400 MHz, DMSO) δ9.38 (s, 1H), 7.45-7.28 (m, 4H), 6.93 (dd, J=7.6, 0.9 Hz, 1H), 6.78 (dd, J=6.6, 2.1 Hz, 1H), 4.02 (d, J=5.3 Hz, 3H). $^{13}$C NMR (101 MHz, DMSO) δ155.89, 154.00, 136.32, 127.46, 126.17, 120.95, 118.49, 114.56, 110.05, 104.44, 56.16, 40.12.

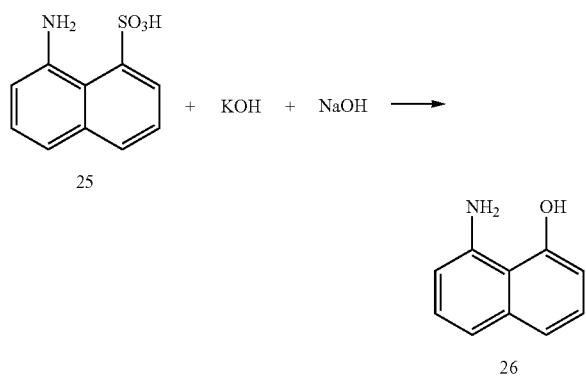

Synthesis of 8-aminonaphthalen-1-ol, 26. Aminonaphthalene sulfonic acid (25) (12.5 g, 56 mmol) was made into a paste with 15 mL of water. KOH (22.3 g, 397 mmol) and NaOH (22.39 g, 560 mmol) were melted at 200° C. in a stainless steel beaker while being stirred using a mechanical stirrer (320 rpm). The aminonaphthalene sulfonic acid paste was added portion wise. The temperature is increased slowly to 260° C. while stirred. When the temperature reached 260° C., the mixture turned dark brown, then it liquefied and the thick melt turned black giving off white fumes. The mixture was kept for additional 15 min at this temperature. The mixture was cooled rapidly to avoid further oxidation. The solidified cake was dissolved in 500 mL of DI water, and filtered. The filtrate was acidified with concentrated HCl to pH 1 and filtered again. The filtrate was neutralized by adding solid $NaHCO_3$ portion wise. The precipitate formed was filtered, washed with water (300 mL) and dried under vacuum. 5.3 g (59%) of 26 were obtained. $^1$H NMR (600 MHz, DMSO) δ7.11-7.03 (m, 3H), 6.86 (dd, J=8.0, 1.1 Hz, 1H), 6.61 (dd, J=5.0, 3.6 Hz, 1H), 6.45 (dd, J=7.5, 1.1 Hz, 1H). $^{13}$C NMR (101 MHz, DMSO) δ155.37, 146.33, 137.19, 126.93, 125.78, 118.89, 114.39, 113.84, 107.33, 107.22. HR ESI [M+H]$^+$ m/z 160.0753, calc. for $C_{10}H_{10}NO$ 160.0756.

Synthesis of N-(8-hydroxynaphthalen-1-yl)acetamide, 28. 8-amino-1-naphthol (26) (5 g, 31 mmol) was suspended in 100 mL of DI water. 6 N l was added until a homogeneous solution was obtained (the mixture is sonicated to help to dissolve the solid. A yellow-black solution was obtained at pH around 1. Acetic anhydride (4.81 g, 47.12 mmol) was added in one portion and the mixture stirred at room temperature; after a few seconds a precipitate started forming. Solid $NaHCO_3$ was added portion wise until pH 6-7 was reached. A cream precipitate was obtained. The precipitate was filtered and washed with water and dissolved in a minimum amount of ethanol. The solution was brought to boil and then activated carbon was added. The mixture was boiled for additional 3 min, then filtered and washed with cold ethanol. DI water was added to the filtrate until a turbid solution was obtained. After 30 min upon standing, the target compound precipitated as small yellow needles. The recrystallized product was filtered, washed with water and then dried under vacuum. 2.05 g, (33%) of 28 were obtained. $^1$H NMR (400 MHz, DMSO) δ11.23 (s, 1H), 11.08 (s, 1H), 8.41 (d, J=7.6 Hz, 1H), 7.49 (dd, J=8.2, 1.0 Hz, 1H), 7.35 (ddd, J=8.2, 6.4, 2.8 Hz, 2H), 6.89 (dd, J=7.4, 1.3 Hz, 1H), 2.15 (s, 3H). $^{13}$C NMR (101 MHz, DMSO) δ167.67, 153.34, 136.17, 135.60, 126.29, 126.05, 122.87, 119.94, 115.10, 114.67, 110.12, 25.29. HR ESI [M+H]$^+$ m/z 202.0856, calc. for $C_{12}H_{11}NO_2$ 202.8202; [M+Na]$^+$ m/z 224.0675, calc. for $C_{12}H_{10}NO_2Na$ 224.0675.

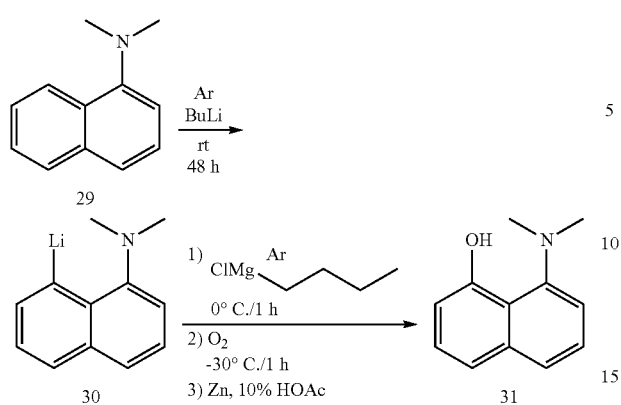

Synthesis of 8-(dimethylamino)naphthalen-1-ol, 31. Under Ar atm, 1.7 M n-butyl lithium in hexanes (4.71 g, 73.6 mmol) was added in a continuous stream to a stirred solution of N,N-dimethyl-1-naphthylamine (29) (2.74 g, 16 mmol) in 35 mL of anhydrous ether. The mixture was stirred 48 h at room temperature. The lithiated naphthylamine (30) solution was cooled down to 0° C. and 2 M n-butyl magnesium chloride in hexanes (7.93 g, 67.9 mmol) was added slowly in order to keep the temperature at 0° C. After 20 min, the reaction mixture was cooled down to −5° C. and maintained at this temperature for 4 h while dry O2 was passed through the solution with stirring. A light yellow-grey precipitate formed and the mixture could no longer be stirred. A solution of 10% acetic acid in water (100 mL) was added under Ar atm, followed by the addition of Zn powder (1 g). The two phases were stirred for 30 min until effervescence had ceased and the aqueous phase was neutral. The flocculated Zn was filtered and the phases separated. The organic phase was washed with saturated NaHCO3 solution (3×50 mL), water (1×50 mL), dried over anhydrous Na2SO4 and the solvent evaporated under vacuum. The target compound 31 was isolated by flash column chromatography on silica gel using 20% ether in hexanes, after pre-absorbing the crude mixture onto silica. Yield: 1.5 g, 50%. $^1$H NMR (400 MHz, CDCl3) δ14.36 (s, 1H), 7.66 (dd, J=8.0, 1.2 Hz, 1H), 7.41-7.26 (m, 4H), 6.85 (dd, J=7.5, 1.2 Hz, 1H), 2.84 (s, 6H). $^{13}$C NMR (101 MHz, CDCl3) δ156.91, 150.08, 136.40, 127.75, 126.80, 125.69, 119.06, 118.05, 116.87, 110.05, 46.47. HR ESI [M+H]$^+$ m/z 188.1072, calc. for $C_{12}H_{14}NO$ 188.1069.

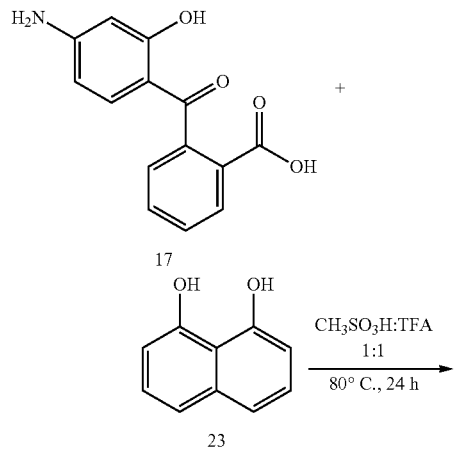

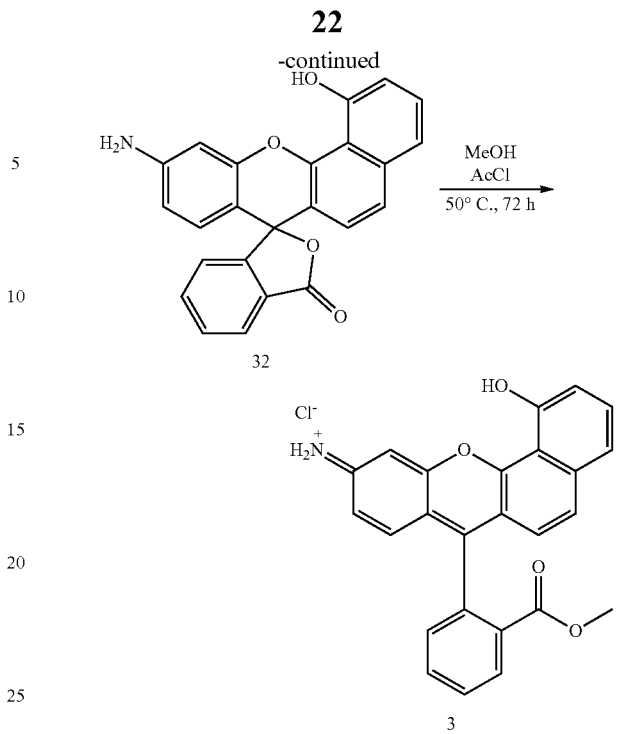

Synthesis of 1-hydroxy-7-(2-(methoxycarbonyl)phenyl)-10H-benzo[c]xanthen-10-iminium chloride, 3. Compound 17 (100 mg, 0.388 mmol) and 1,8-dihydroxynaphthalene (23) (93.4 mg, 0.583 mmol) were dissolved in 1.5 mL of methanesulfonic acid. 1.5 mL of TFA was added and the mixture heated at 80° C. for 24 h. The mixture was allowed to cool down to room temperature and then poured into 20 mL of DI water. The precipitate formed was filtered and washed with water until the filtrate is neutral. The title compound was isolated by flash column chromatography on silica gel using CH2Cl2:MeOH 95:5 for elution. 144 mg, (97%) of 32 were obtained. $^1$H NMR (600 MHz, DMSO) δ9.86 (s, 1H), 8.05-7.98 (m, 1H), 7.79 (td, J=7.5, 1.1 Hz, 1H), 7.76-7.69 (m, 1H), 7.47-7.39 (m, 2H), 7.32 (d, J=7.4 Hz, 1H), 7.27 (d, J=7.6 Hz, 1H), 7.05-7.00 (m, 1H), 6.63 (d, J=2.1 Hz, 1H), 6.59 (t, J=6.5 Hz, 1H), 6.43 (d, J=8.5 Hz, 1H), 6.39 (dd, J=8.6, 2.2 Hz, 1H), 5.69 (s, 2H). $^{13}$C NMR (151 MHz, DMSO) δ168.80, 154.80, 152.95, 151.39, 151.24, 148.21, 136.56, 135.55, 130.01, 128.65, 128.18, 126.25, 124.55, 124.10, 123.87, 123.31, 118.68, 113.96, 112.20, 111.82, 111.72, 104.67, 99.58, 84.17. HR ESI [M+H]$^+$ m/z 382.1081, calc for $C_{24}H_{16}NO_4$ 382.1073. Compound 32 (50 mg, 131 μmol) was dissolved in 25 mL of anhydrous MeOH. 0.750 mL of acetyl chloride was added dropwise. The mixture was stirred and heated at 50° C. for 48 h. 0.3 mL of acetyl chloride was added and the mixture was kept at 50° C. for additional 24 h. The solvent was evaporated under vacuum. The title compound 3 was purified in a $C_{18}$ reversed phase SPE cartridge using MeOH:H2O 2:8, MeOH:H2O 1:1 for elution. Yield 45.44 mg (88%). $^1$H NMR (400 MHz, DMSO) δ11.47 (s, 1H), 8.91 (d, J=15.4 Hz, 2H), 8.34 (dd, J=7.9, 1.0 Hz, 1H), 7.99 (td, J=7.5, 1.3 Hz, 1H), 7.90 (td, J=7.7, 1.3 Hz, 1H), 7.85-7.77 (m, 2H), 7.61-7.55 (m, 2H), 7.36 (d, J=7.2 Hz, 1H), 7.29 (d, J=9.3 Hz, 1H), 7.24-7.14 (m, 2H), 7.02 (d, J=9.0 Hz, 1H), 3.56 (s, 3H). $^{13}$C NMR (101 MHz, DMSO) δ165.09, 161.45, 160.00, 158.19, 157.57, 154.18, 138.39, 133.70, 133.59, 133.52, 131.77, 130.97, 130.75, 130.42, 129.08, 127.17, 122.51, 121.50, 119.26, 117.47, 117.10, 114.08, 112.28, 96.84, 52.48. HR ESI [M]+ m/z 396.1240, calc. for $C_{25}H_{18}NO_4$ 396.1230.

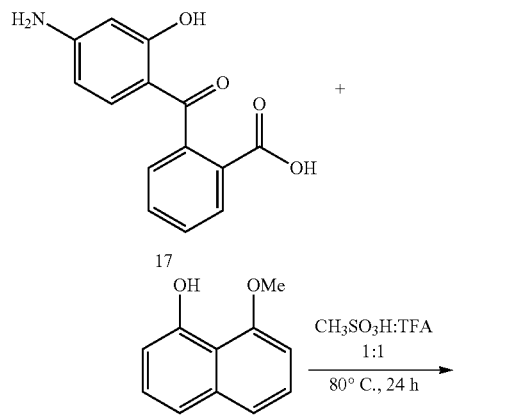

Synthesis of 1-methoxy-7-(2-(methoxycarbonyl)phenyl)-10H-benzo[c]xanthen-10-iminium bicarbonate, 4. Compound 17 (150 mg, 0.583 mmol), and compound 24 (152 mg, 0.875 mmol) were dissolved in 1 mL of methanesulfonic acid, then 1 mL of TFA was added. The mixture was stirred at 80° C. for 16 h. The mixture was cooled down to room temperature and poured into 50 mL of DI water. The mixture was neutralized to pH 6-7 by portion wise addition of solid NaHCO3. The precipitate formed was filtered and washed with water (25 mL), then air dried. The title compound 33 was isolated by flash column chromatography using $CH_2Cl_2$:MeOH 9:1 for elution. Yield 157 mg (68%). $^1$H NMR (400 MHz, DMSO) δ8.05-7.99 (m, 1H), 7.78 (dd, J=7.5, 1.2 Hz, 1H), 7.73 (dd, J=7.5, 1.0 Hz, 1H), 7.56 (t, J=7.9 Hz, 1H), 7.47 (dd, J=13.7, 8.2 Hz, 2H), 7.29-7.24 (m, 1H), 7.16 (d, J=7.2 Hz, 1H), 6.65 (d, J=8.7 Hz, 1H), 6.60 (d, J=2.0 Hz, 1H), 6.40 (dt, J=8.6, 5.3 Hz, 2H), 5.68 (s, 2H), 4.05 (s, 3H). $^{13}$C NMR (101 MHz, DMSO) δ168.83, 157.04, 153.02, 151.59, 151.31, 148.04, 136.49, 135.58, 130.04, 128.46, 128.17, 126.22, 124.58, 124.42, 124.14, 123.19, 120.30, 114.95, 112.83, 111.72, 108.26, 104.64, 99.48, 84.29, 56.42. HR ESI [M+H]+ m/z 396.1230, calc. for $C_{25}H_{18}NO_4$ 396.1230. Compound 33 (50 mg, 126 μmol) was dissolved in 2 mL of MeOH. To this solution was added concentrated $H_2SO_4$ (100 μL) dropwise, then the mixture was refluxed for 24 h. The mixture was allowed to cool down to room temperature, then poured into 50 mL of ice water and 200 mg of NaHCO3 was added in one portion. The precipitate formed was washed with 2% NaHCO3 (2×10 mL). The solid was transferred to a flask containing 50 mL of 2% HOAc. The pH of the solution was adjusted to 6-7 using 1 M NaOH. The aqueous phase was extracted with CHCl3 (3×100 mL). The organic phase was dried over anhydrous $Na_2SO_4$ and the solvent evaporated under vacuum to leave a dark purple solid. The title compound 4 was isolated by flash column chromatography on silica gel using $CH_2Cl_2$:MeOH 9:1 for elution. Yield 49 mg, 94%. $^1$H NMR (400 MHz, DMSO) δ8.97 (d, J=5.3 Hz, 2H), 8.34 (dd, J=7.9, 1.0 Hz, 1H), 8.04-7.85 (m, 4H), 7.72 (d, J=7.8 Hz, 1H), 7.57 (dd, J=7.6, 1.0 Hz, 1H), 7.49 (d, J=7.8 Hz, 1H), 7.30 (d, J=9.3 Hz, 1H), 7.24-7.14 (m, 2H), 7.10 (d, J=8.9 Hz, 1H), 4.22 (s, 3H), 3.54 (s, 3H). $^{13}$C NMR (101 MHz, DMSO) δ165.07, 161.76, 160.07, 158.44, 158.33, 153.23, 138.40, 133.62, 133.54, 133.33, 131.96, 131.00, 130.80, 130.43, 129.09, 127.03, 123.23, 121.82, 120.86, 117.96, 117.43, 113.08, 109.82, 96.87, 56.82, 52.77, 52.48. HR ESI [M]+ m/z 410.1400, calc. for $C_{26}H_{20}NO_4$ 410.1386.

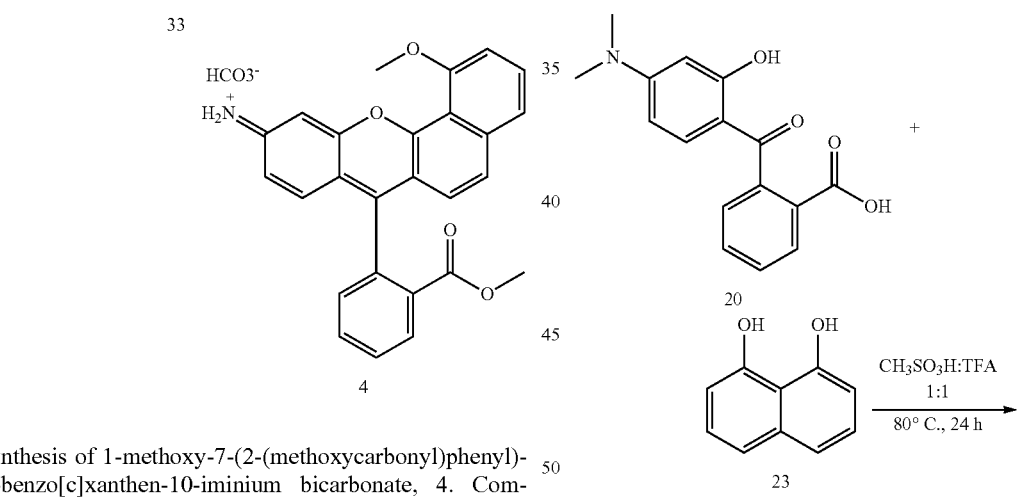

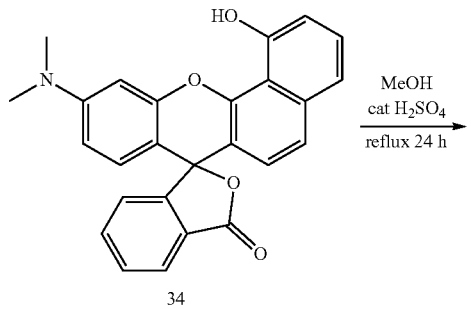

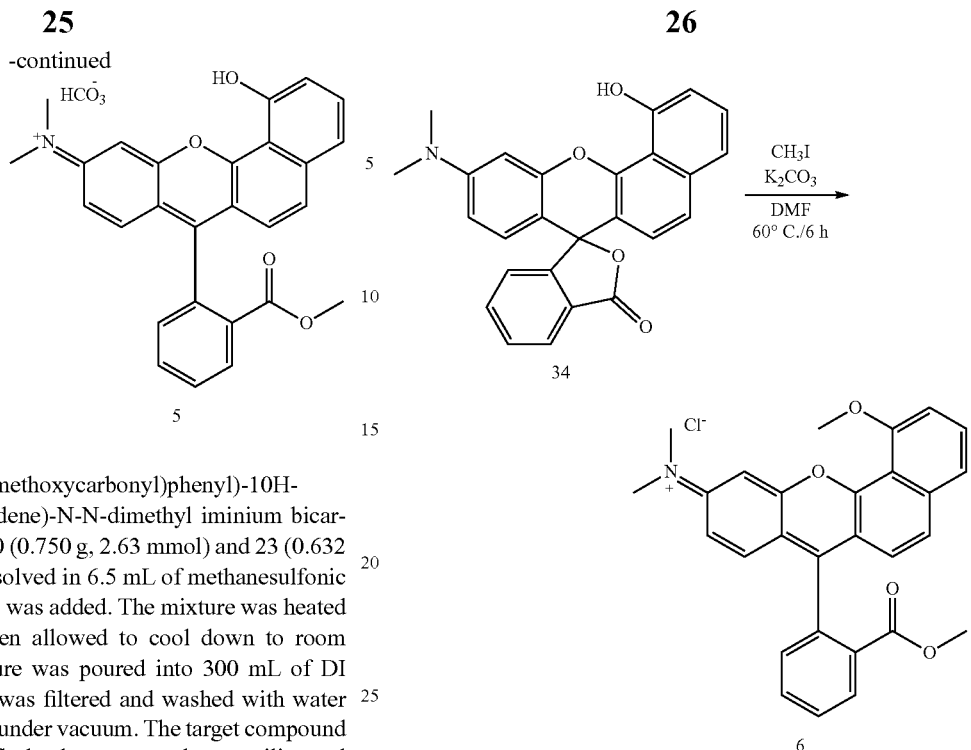

N-(1-hydroxy-7-(2-(methoxycarbonyl)phenyl)-10H-benzo[c]xanthen-10-ylidene)-N-N-dimethyl iminium bicarbonate, 5. Compound 20 (0.750 g, 2.63 mmol) and 23 (0.632 g, 3.94 mmol) were dissolved in 6.5 mL of methanesulfonic acid, then TFA (6.5 mL) was added. The mixture was heated at 80° C. for 24 h, then allowed to cool down to room temperature. The mixture was poured into 300 mL of DI water, the purple solid was filtered and washed with water (3×100 mL), then dried under vacuum. The target compound 34 was separated by flash chromatography on silica gel using $CHCl_3$:MeOH 9:1 for elution. Yield 0.778 g, 72%. $^1$H NMR (400 MHz, $CDCl_3$) δ9.12 (s, 1H), 8.08-8.04 (m, 1H), 7.65 (m, J=14.4, 7.3, 1.3 Hz, 2H), 7.47 (t, J=7.9 Hz, 1H), 7.41 (d, J=8.8 Hz, 1H), 7.32 (dd, J=8.1, 0.9 Hz, 1H), 7.18-7.15 (m, 1H), 7.08 (dd, J=7.7, 1.0 Hz, 1H), 6.69 (dd, J=8.8, 4.2 Hz, 2H), 6.55-6.48 (m, 2H), 3.03 (s, 6H). $^{13}$C NMR (101 MHz, $CDCl_3$) δ169.70, 154.32, 153.52, 152.23, 150.95, 148.59, 136.63, 135.18, 129.88, 129.16, 129.00, 126.97, 125.23, 124.43, 124.11, 124.06, 119.69, 113.38, 112.72, 112.56, 110.23, 105.84, 97.93, 83.39, 40.44. HR ESI $[M+H]^+$ found 410.1392, calc. for $C_{26}H_{20}NO_4$ 410.1368. Compound 34 (100 mg, 243 μmol) was dissolved in 2 mL of MeOH. To this solution was added concentrated $H_2SO_4$ (100 μL) dropwise, then the mixture was refluxed for 16 h. The mixture was allowed to cool down to room temperature, then poured into 50 mL of ice water and filtered. The precipitate was washed with 2% $NaHCO_3$ (2×10 mL). The solid was transferred to a flask containing 50 mL of 2% HOAc. The pH of the solution was adjusted to 6-7 using 1 M NaOH. The aqueous phase was extracted with $CHCl_3$ (3×100 mL). The organic phase was dried over anhydrous $Na_2SO_4$ and the solvent evaporated under vacuum to leave a dark purple solid. The target compound 5 was isolated by flash column chromatography. A dark purple band was eluted with $CHCl_3$:MeOH 9:1, 8:2; yield 36 mg. A second green band was eluted with $CHCl_3$:MeOH 1:1, then 1:3; yield 61 mg. Total yield of 34, 97 mg, (94%). $^1$H NMR (400 MHz, DMSO) δ8.32 (d, J=7.0 Hz, 1H), 7.97 (d, J=7.5 Hz, 1H), 7.89 (t, J=7.1 Hz, 1H), 7.72 (t, J=8.6 Hz, 2H), 7.58 (d, J=6.7 Hz, 1H), 7.43-7.34 (m, 2H), 7.26 (d, J=8.1 Hz, 1H), 7.20 (d, J=9.6 Hz, 1H), 7.09 (d, J=2.4 Hz, 1H), 6.93 (d, J=9.0 Hz, 1H), 3.54 (s, 3H), 3.39 (s, 6H). $^{13}$C NMR (101 MHz, DMSO) δ165.29, 158.40, 154.28, 153.85, 138.93, 135.22, 134.73, 133.24, 130.70, 129.87, 128.79, 127.72, 124.06, 120.52, 117.48, 113.21, 96.43, 94.54, 79.25, 52.13. HR ESI $[M^+]$m/z 424.1540, calc for $C_{27}H_{22}NO_4^+$ 424.1543.

N-(1-methoxy-7-(2-(methoxycarbonyl)phenyl)-10H-benzo[c]xanthen-10-ylidene)-N-methylmethanaminium chloride, 6. Compound 34 (50 mg, 0.122 mmol), $K_2CO_3$ (67.5 mg, 0.488 mmol) were suspended in 0.6 mL of anhydrous DMF, $CH_3I$ (104 mg, 0.732 mmol) was added in one portion. The mixture as stirred at 60° C. for 6 h, then allowed to cool down to room temperature. 2 mL of saturated $NH_4Cl$ were added to quench the reaction. The precipitate formed was filtered and washed with 0.5% NaOH (2 mL), then with water (25 mL). The title compound 6 was isolated by flash column chromatography on silica gel using $CH_2Cl_2$:MeOH 9:1 for elution. Yield: 4.5 mg, (8%). $^1$H NMR (400 MHz, $CDCl_3$) δ8.36 (d, J=7.9 Hz, 1H), 7.87 (d, J=7.5 Hz, 1H), 7.84-7.77 (m, 2H), 7.66 (d, J=9.0 Hz, 1H), 7.61 (dd, J=9.7, 2.0 Hz, 1H), 7.53 (d, J=7.7 Hz, 1H), 7.40 (d, J =7.5 Hz, 1H), 7.35 (d, J=9.7 Hz, 1H), 7.24 (s, 1H), 7.13 (s, 1H), 7.09 (d, J=8.9 Hz, 1H), 4.30 (s, 3H), 3.63 (s, 3H), 3.59 (s, 6H). $^{13}$C NMR (101 MHz, $CDCl_3$) δ165.45, 160.65, 159.55, 159.11, 158.31, 154.73, 139.21, 134.11, 133.58, 133.39, 131.66, 131.12, 130.89, 130.39, 129.82, 127.38, 123.24, 120.99, 119.99, 118.60, 117.63, 114.24, 109.24, 96.78, 57.11, 52.76, 42.53, 29.84. HR ESI $[M^+]$ m/z 438.1698, calc for $C_{28}H_{24}NO_4^+$; 438.1699.

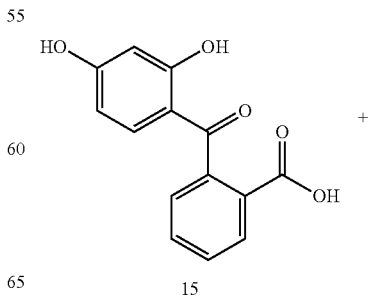

15

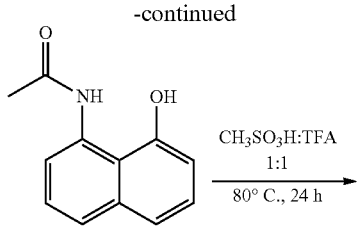

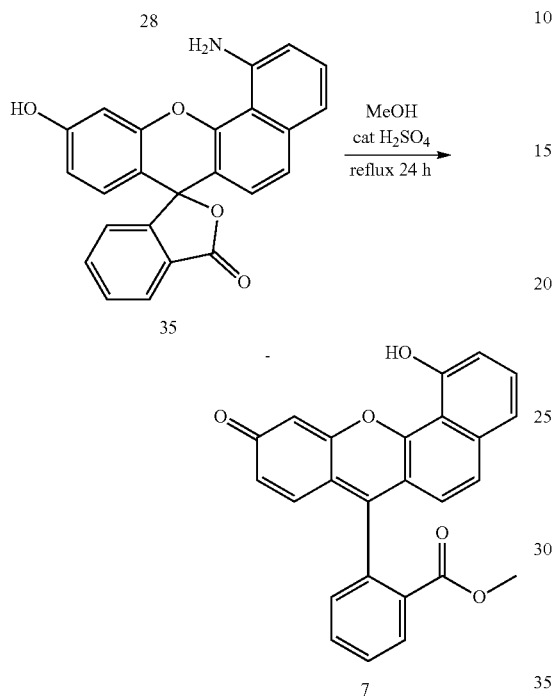

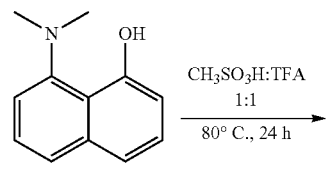

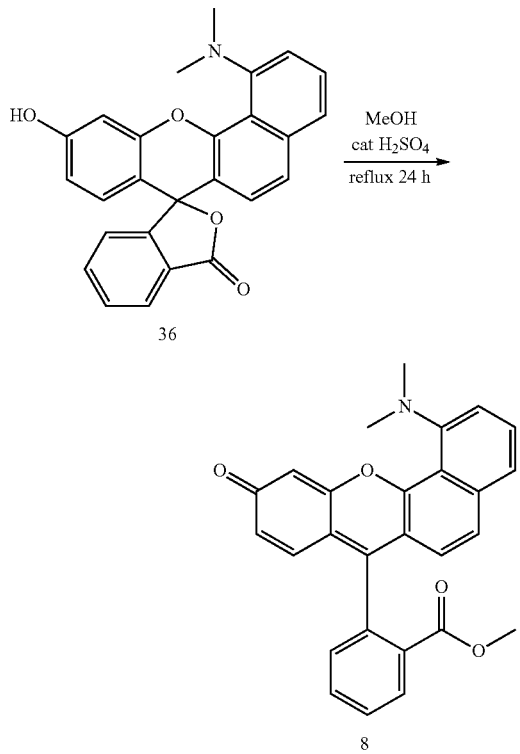

Synthesis of methyl 2-(1-amino-10-oxo-10H-benzo[c]xanthen-7-yl)benzoate 7. Compound 15 (200 mg, 0.774 mmol), and compound 28 (234 mg, 1.16 mmol) were dissolved in 2.5 mL of methanesulfonic acid, then 2.5 mL of TFA were added. The mixture was stirred at 80° C. for 24 h, then cooled down to room temperature. The mixture was poured into 50 mL of DI water, the precipitate obtained was filtered and washed with DI water, then air dried. The title compound was isolated by flash column chromatography on silica gel using $CH_2Cl_2$:MeOH 9:1. 33 mg of a mixed fraction containing the target product 35 was isolated. 17 mg of the 35 mixed fraction was dissolved in 1 mL of MeOH, 50 μL of concentrated sulfuric acid was added in one portion. The mixture was refluxed for 16 h, then the mixture was allowed to cool down to room temperature and poured into 10 mL of DI water. 200 mg of $NaHCO_3$ was added in one portion. The precipitate formed was filtered and washed with aqueous 2% $NaHCO_3$, the precipitate was then suspended in 25 mL of 2% HOAc. A dark brown black suspension was obtained. The mixture was neutralized to pH 6-7 by adding solid NaHCO3 portion wise. The aqueous phase was extracted with $CHCl_3$ (3×50 mL). The organic extracts were combined, dried over anhydrous $Na_2SO_4$, filtered and the solvent evaporated under vacuum to leave a black precipitate. The title compound 7 was isolated by flash column chromatography on silica gel using $CH_2Cl_2$:MeOH 9:1 for elution. Yield 2.7 mg, 15%. $^1$H NMR (400 MHz, $CDCl_3$) δ8.29 (dd, J=7.8, 1.1 Hz, 1H), 7.78 (td, J=7.5, 1.4 Hz, 1H), 7.71 (td, J=7.7, 1.4 Hz, 1H), 7.47 (t, J=7.9 Hz, 1H), 7.41 (d, J=8.9 Hz, 1H), 7.35 (dd, J=7.5, 1.0 Hz, 1H), 7.17 (d, J=7.7 Hz, 1H), 6.94 (d, J=9.6 Hz, 1H), 6.86 (d, J=7.8 Hz, 1H), 6.82 (d, J=8.9 Hz, 1H), 6.68 (dd, J=9.6, 1.9 Hz, 1H), 6.63 (d, J=1.9 Hz, 1H), 5.69 (s, 2H), 3.63 (s, 3H). $^{13}$C NMR (101 MHz, $CDCl_3$) δ185.06, 158.17, 146.15, 137.97, 135.26, 132.99, 131.36, 131.30, 130.72, 129.90, 129.82, 125.81, 122.57, 117.43, 112.65, 111.41, 105.15, 52.60. HR ESI [M+H$^+$] m/z 396.1240, calc for $C_{25}H_{18}NO_4^+$ 396.1230.

Synthesis of methyl 2-(1-(dimethylamino)-10-oxo-10H-benzo[c]xanthen-7-yl)benzoate, 8. Compound 15 (200 mg, 0.774 mmol), compound 31 (217.5 mg, 1.16 mmol) were dissolved in 2.5 mL of methanesulfonic acid, then 2.5 mL of TFA was added. The mixture was stirred at 80° C. for 24 h, then cooled down to room temperature. The mixture was poured into 50 mL of DI water, and the precipitate obtained was filtered and washed with DI water, then air dried. The crude mixture was separated by flash column chromatography on silica gel using $CH_2Cl_2$:MeOH 95:5 for elution; 15 mg of a mixed fraction containing 36 was isolated. 10 mg of the 36 mixed fraction were dissolved in 1 mL of MeOH, 50 μL of concentrated sulfuric acid was added in one portion. The mixture was refluxed for 16 h, then the mixture was allowed to cool down to room temperature and poured into 10 mL of DI water. 200 mg of $NaHCO_3$ was added in one portion. The precipitate formed was filtered and washed with aqueous 2% $NaHCO_3$. The precipitate was then suspended in 25 mL of 2% HOAc. The mixture was neutralized to pH 6-7 by adding solid $NaHCO_3$ portion wise. The aqueous phase was extracted with $CHCl_3$ (3×50 mL). The organic extracts were combined, dried over anhydrous $Na_2SO_4$, filtered and the solvent evaporated under vacuum. The crude mixture was separated by flash column chromatography on silica gel using $CH_2Cl_2$:MeOH 9:1 for elution. The isolated fraction (5.9 mg) containing the target product 8 was further separated by flash column chromatography on silica gel using EtOAc:MeOH 95:5 for elution. Yield, 1.5 mg, (14.5%). $^1$H NMR (400 MHz, $CDCl_3$) δ8.29 (dd, J=7.8, 1.1 Hz, 1H), 7.77 (td, J=7.5, 1.5 Hz, 1H), 7.70 (td, J=7.7, 1.4 Hz, 1H), 7.56 (t, J=7.9 Hz, 1H), 7.47 (d, J=8.9 Hz, 1H), 7.39 (d, J=7.3 Hz, 1H), 7.36 (dd, J=7.5, 1.0 Hz, 1H), 7.21 (dd, J=7.8, 0.9 Hz, 1H), 6.92 (dd, J=9.1, 7.4 Hz, 2H), 6.70 (s, 2H), 3.59 (s, 3H), 3.04 (s, 6H). $^{13}$C NMR (101 MHz, $CDCl_3$) δ165.77, 158.79, 152.34, 138.80, 135.39, 132.90, 131.35, 131.12, 130.80, 130.54, 130.21, 129.80, 129.52, 125.54, 123.04, 121.50, 117.37, 116.79, 116.12, 105.25, 52.52, 45.39. HR ESI [M$^+$] m/z 424.1556, calc for $C_{27}H_{22}NO_4^+$ 424.1543.

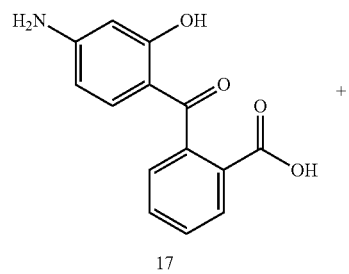

17

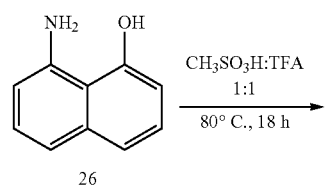

26

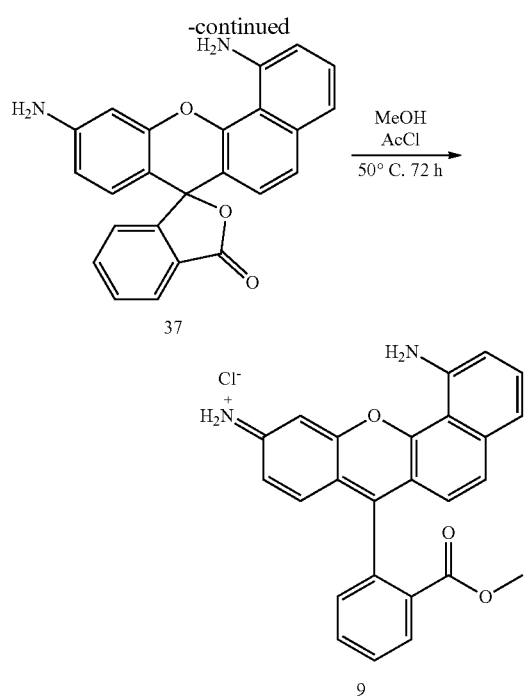

Synthesis of 1-amino-7-(2-(methoxycarbonyl)phenyl)-10H-benzo[c]xanthen-10-iminium chloride, 9. Compound 17 (310 mg, 1.21 mmol), 8-aminonaphthalen-1-ol (26) (287.75 mg, 1.81 mmol) were dissolved in 4.5 mL of methanesulfonic acid, then 4.5 mL of TFA was added. The mixture was stirred at 80° C. for 18 h, then cooled down to room temperature. The mixture was poured into 60 mL of DI water, and the mixture was brought to pH 5 by portion wise addition of solid $NaHCO_3$. The dark green precipitate obtained was filtered and washed with DI water. The title compound 37 was isolated by flash column chromatography on silica gel using $CH_2Cl_2$:MeOH 9:1 for elution. Yield 254.9 mg, 56%. $^1$H NMR (400 MHz, DMSO) δ8.01 (d, J=7.6 Hz, 1H), 7.80 (td, J=7.5, 1.1 Hz, 1H), 7.72 (td, J=7.5, 0.7 Hz, 1H), 7.36-7.25 (m, 3H), 7.00 (d, J=7.6 Hz, 1H), 6.82 (dd, J=7.7, 0.7 Hz, 1H), 6.71 (d, J=1.8 Hz, 1H), 6.48 (d, J=8.7 Hz, 1H), 6.43 (d, J=2.6 Hz, 1H), 6.35 (s, 2H), 5.69 (s, 2H). $^{13}$C NMR (101 MHz, DMSO) δ168.81, 152.83, 151.27, 150.99, 149.26, 146.12, 136.51, 135.56, 130.04, 128.83, 128.31, 126.32, 124.58, 124.11, 123.88, 123.27, 115.01, 111.96, 111.69, 110.79, 110.69, 104.78, 99.30, 84.15. HR ESI [M+H]$^+$ m/z 381.1232, calc. for $C_{24}H_{17}N_2O_3$ 381.1233. Compound 37 (25 mg, 66 μmol) was dissolved in 20 mL of anhydrous MeOH; 1.0 mL of acetyl chloride was added drop wise. The mixture was stirred and heated at 50° C. for 48 h; 0.5 mL of acetyl chloride was added and the mixture was kept at 50° C. for additional 24 h. The solvent was evaporated under vacuum. The title compound 9 was isolated by flash column chromatography on silica gel using $CH_2Cl_2$:MeOH 90:10, 85:15, 80:20 for elution. Yield 24 mg, 93%. $^1$H NMR (400 MHz, DMSO) δ8.70 (s, 2H), 8.32 (d, J=6.9 Hz, 1H), 7.99-7.94 (m, 1H), 7.88 (dd, J=10.9, 4.5 Hz, 1H), 7.70-7.63 (m, 1H), 7.55 (dd, J=7.6, 1.0 Hz, 1H), 7.47 (d, J=2.0 Hz, 1H), 7.33 (s, 2H), 7.23-7.13 (m, 4H), 6.86 (d, J=9.0 Hz, 2H), 3.56 (s, 3H). $^{13}$C NMR (101 MHz, DMSO) δ165.08, 160.42, 158.80, 157.07, 156.39, 149.40, 137.94, 134.03, 133.90, 133.49, 131.31, 130.92, 130.64, 130.42, 129.10, 127.83, 121.75, 120.61, 116.80, 115.91, 115.79, 113.85, 108.57, 97.90, 52.46. HR ESI [M]+ m/z 395.1386, calc. for $C_{25}H_{19}N_2O_3^+$ 395.1390.

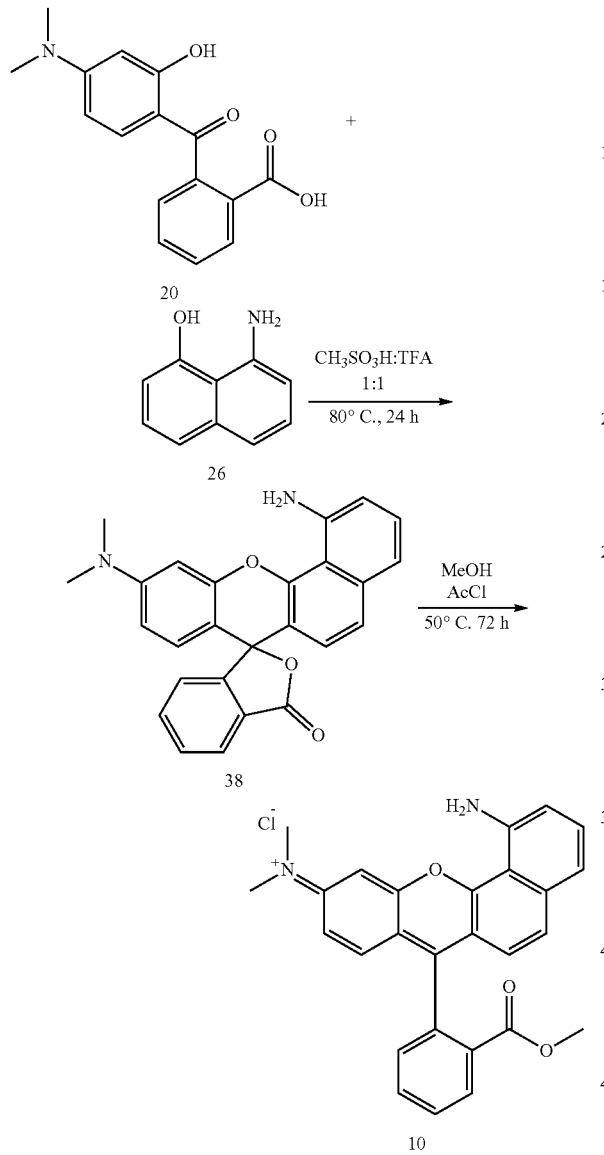

Synthesis of N-(1-amino-7-(2-(methoxycarbonyl)phenyl)-10H-benzo[c]xanthen-10-ylidene)-N-methylmethanaminium, 10. Compound 20 (450 mg, 1.58 mmol), 8-aminonaphthalen-1-ol (26) (326.41 mg, 2.05 mmol) were dissolved in 2 mL of methanesulfonic acid, then 2 mL of TFA was added. The mixture was stirred at 80° C. for 24 h, then cooled down to room temperature. The mixture was poured into 150 mL of DI water, and the mixture was neutralized by portion wise addition of NaHCO$_3$. The dark green precipitate obtained was filtered and washed with DI water then air dried. The target compound 38 was isolated by flash column chromatography on silica gel using CH$_2$Cl$_2$:MeOH 95:5, 9:1, Yield 265 mg, 41%. $^1$H NMR (400 MHz, DMSO) δ8.03 (d, J=7.4 Hz, 1H), 7.79 (dt, J=7.5, 3.8 Hz, 1H), 7.73 (dt, J=7.4, 3.7 Hz, 1H), 7.37-7.24 (m, 3H), 6.98 (dd, J=10.7, 4.6 Hz, 2H), 6.87 (d, J=7.8 Hz, 1H), 6.59-6.56 (m, 2H), 6.50 (d, J=8.7 Hz, 1H), 6.37 (s, 2H), 2.99 (s, 6H). $^{13}$C NMR (101 MHz, DMSO) δ168.81, 152.93, 152.03, 151.06, 149.38, 146.16, 136.58, 135.60, 130.09, 128.85, 128.09, 126.22, 124.63, 124.09, 123.99, 123.22, 114.82, 111.58, 110.81, 110.49, 109.99, 105.02, 98.69, 83.96. HR ESI [M+H+] m/z 409.15743, calc. for $C_{26}H_{21}N_2O_3^+$ 409.15466. Under Ar, compound 38 (25 mg, 0.043 mmol) was dissolved in 12.5 mL of anhydrous MeOH. The solution was cooled down to 0° C. in an ice bath, and 0.375 mL of acetyl chloride was added drop wise. The mixture was stirred and heated at 50° C. for 48 h; 0.2 mL of acetyl chloride was added and the mixture was kept at 50° C. for additional 24 h. The solvent was evaporated under vacuum. 27 mg (96%) of 10 were obtained. $^1$H NMR (400 MHz, DMSO) δ8.33 (dd, J=7.9, 1.0 Hz, 1H), 7.97 (td, J=7.5, 1.3 Hz, 1H), 7.92-7.85 (m, 2H), 7.68 (dd, J=16.6, 8.6 Hz, 2H), 7.56 (dd, J=7.6, 1.0 Hz, 1H), 7.43-7.34 (m, 3H), 7.26-7.16 (m, 3H), 6.87 (d, J=9.0 Hz, 1H), 3.55 (s, 3H), 3.38 (d, J=8.3 Hz, 6H). $^{13}$C NMR (101 MHz, DMSO) δ165.10, 158.47, 157.60, 156.82, 156.39, 149.34, 137.95, 133.89, 133.52, 130.96, 130.69, 130.41, 129.13, 127.95, 121.73, 117.08, 115.74, 115.55, 113.83, 108.24, 97.33, 52.77, 52.48. HR ESI [M+] m/z 423.17298, calc. for $C_{27}H_{23}N_2O_3^+$ 423.17031.

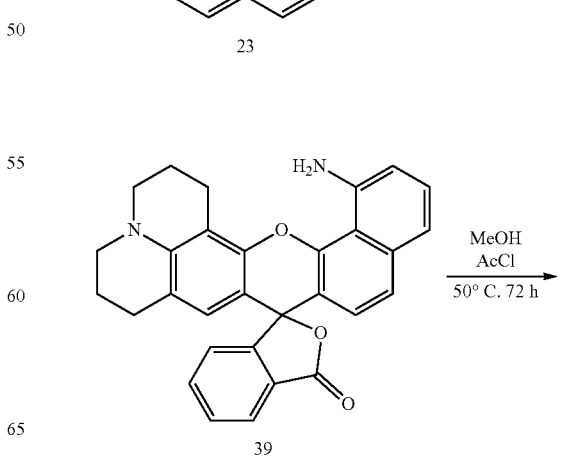

-continued

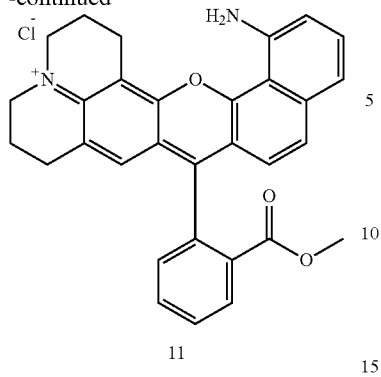

11

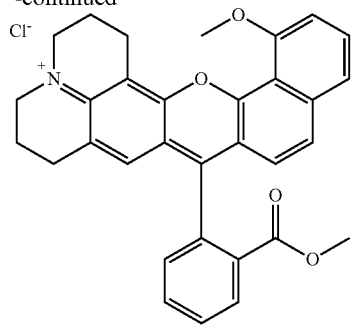

12

Synthesis of 15-hydroxy-9-(2-(methoxycarbonyl)phenyl)-1,2,3,5,6,7-hexahydrobenzo[7,8]chromeno[2,3-f]pyrido[3,2,1-ij]quinolin-4-ium chloride, 11. Compound 22 (200 mg, 0.593 mmol) and 1,8-dihydroxynaphthalene (23) (142 mg, 0.889 mmol) were dissolved in 1.5 mL of methanesulfonic acid, then 1.5 mL of TFA was added. The mixture was stirred at 80° C. for 24 h, then cooled down to room temperature. The mixture was poured into 50 mL of DI water. The precipitate obtained was filtered and washed with DI water then dried under vacuum. 256 mg (93%) of 39 were obtained. $^1$H NMR (400 MHz, DMSO) δ11.39 (s, 1H), 8.27 (d, J=7.7 Hz, 1H), 7.90 (t, J=7.3 Hz, 1H), 7.83 (t, J=7.5 Hz, 1H), 7.70 (dd, J=17.0, 8.5 Hz, 2H), 7.48 (t, J=7.3 Hz, 2H), 7.24 (d, J=7.8 Hz, 1H), 6.92 (d, J=8.9 Hz, 1H), 6.85 (s, 1H), 3.63 (d, J=22.7 Hz, 6H), 2.76 (s, 2H), 2.06 (s, 2H), 1.91 (s, 2H). $^{13}$C NMR (101 MHz, DMSO) δ166.46, 158.01, 157.68, 156.84, 137.90, 133.16, 130.38, 126.35, 125.32, 122.66, 119.13, 118.37, 115.38, 113.42, 112.67, 105.31, 50.94, 50.64, 26.89, 19.77, 18.86. Compound 39 (50 mg, 0.108 mmol) was dissolved in 25 mL of anhydrous MeOH. 0.75 mL of acetyl chloride was added drop wise. The mixture was stirred and heated at 50° C. for 48 h. 0.3 mL of acetyl chloride was added and the mixture was kept at 50° C. for additional 24 h. The solvent was evaporated under vacuum, and the target compound 11 was isolated by flash column chromatography on silica gel using $CH_2Cl_2$:MeOH 90:10 for elution. Yield 46 mg, 90%. $^1$H NMR (400 MHz, DMSO) δ11.50 (s, 1H), 8.33 (d, J=7.8 Hz, 1H), 7.97 (t, J=7.3 Hz, 1H), 7.92-7.85 (m, 1H), 7.73 (dd, J=12.5, 8.5 Hz, 2H), 7.53 (t, J=7.9 Hz, 2H), 7.31 (d, J=7.9 Hz, 1H), 6.95-6.87 (m, 2H), 3.71 (s, 2H), 3.65 (s, 2H), 3.56 (s, 3H), 3.33 (s, 2H), 2.78 (s, 2H), 2.08 (s, 2H), 1.92 (s, 2H). $^{13}$C NMR (101 MHz, DMSO) δ201.26, 164.65, 157.10, 156.33, 152.34, 130.52, 129.06, 116.89, 113.67, 113.39, 112.24, 105.24, 103.61, 52.59, 50.51, 19.55, 18.60. HR ESI [M]$^+$ m/z 476.1858, calc. for $C_{31}H_{26}NO_4^+$ 476.1856.

Synthesis of 15-methoxy-9-(2-(methoxycarbonyl)phenyl)-1,2,3,5,6,7-hexahydrobenzo[7,8]chromeno[2,3-f]pyrido[3,2,1-ij]quinolin-4-ium chloride, 12. Under Ar atm, compound 39 (25 mg, 0.054 mmol) was dissolved in 0.5 mL of anhydrous DMF. To this solution was added $K_2CO_3$ (22.5 mg, 0.162 mmol) and $CH_3I$ (31 mg, 0.217 mmol). The mixture was heated at 60° C. for 24 h, then allowed to cool down to room temperature. 2 mL of saturated $NH_4Cl$ was added to quench the reaction. The precipitate formed was filtered and washed with 0.5% NaOH (2 mL), then with water (25 mL). The title compound 12 was isolated by flash column chromatography on silica gel using $CH_2Cl_2$:MeOH 90:10 for elution. Yield: 16 mg, 59%. $^1$H NMR (400 MHz, CDCl$_3$) δ8.36 (dd, J=7.9, 1.1 Hz, 1H), 7.91-7.84 (m, 1H), 7.82-7.72 (m, 2H), 7.60 (d, J=8.9 Hz, 1H), 7.50 (d, J=7.9 Hz, 1H), 7.39 (d, J=6.7 Hz, 1H), 7.20 (d, J=8.0 Hz, 1H), 7.01 (d, J=8.9 Hz, 1H), 6.78 (s, 1H), 4.22 (s, 3H), 4.05-3.89 (m, 2H), 3.84-3.69 (m, 2H), 3.64 (s, 3H), 3.38 (dd, J=12.8, 7.2 Hz, 2H), 2.95-2.74 (m, 2H), 2.39-2.01 (m, 4H). $^{13}$C NMR (101 MHz, CDCl$_3$) δ165.59, 158.81, 156.53, 154.52, 153.32, 138.73, 134.59, 133.58, 132.36, 131.54, 130.76, 130.56, 129.86, 129.77, 126.66, 125.79, 123.21, 120.99, 118.11, 117.86, 114.58, 108.74, 106.16, 56.79, 52.74, 52.32, 52.05, 28.08, 20.40, 20.18, 19.65. HR ESI [M]$^+$ m/z 490.2026, calc. for $C_{32}H_{28}NO_4^+$ 490.2012.

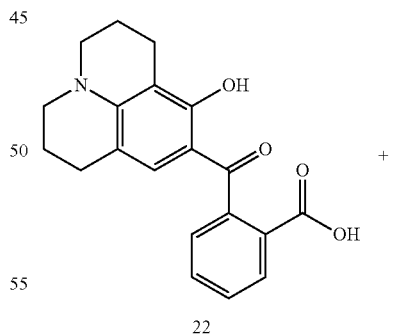

22

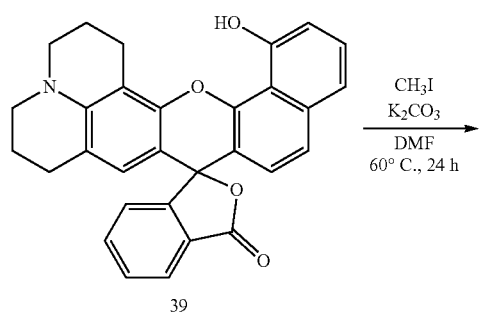

39

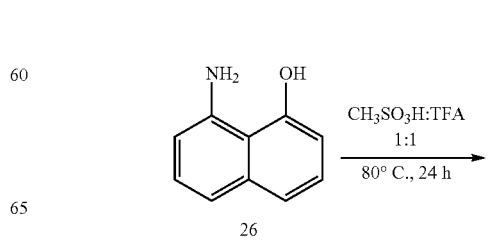

26

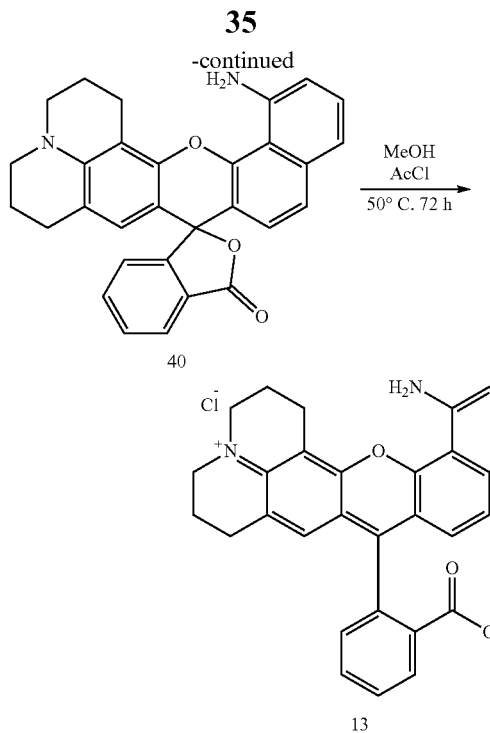

Synthesis of 15-amino-9-(2-(methoxycarbonyl)phenyl)-1,2,3,5,6,7-hexahydrobenzo[7,8]chromeno[2,3-f]pyrido[3,2,1-ij]quinolin-4-ium chloride, 13. Compound 22 (100 mg, 0.296 mmol) and compound 26 (71 mg, 0.444 mmol) were dissolved in 1.5 mL of methanesulfonic acid, then 1.5 mL of TFA was added. The mixture was stirred at 80° C. for 24 h, then cooled down to room temperature. The mixture was poured into 50 mL of DI water, then neutralized by portion wise addition of NaHCO$_3$. The green precipitate obtained was filtered and washed with DI water, then air dried. The target compound was isolated by flash column chromatography on silica gel using CH$_2$Cl$_2$:MeOH 90:10, 80:20, and then 100% MeOH to elute the last dark green band that corresponded to the target compound 40. The MeOH fraction was evaporated under vacuum, and the resulting solid was dissolved in a mixture of CH$_2$Cl$_2$:MeOH 90:10 and filtered through a 0.22 μm filter to remove any dissolved silica. Yield 52 mg, 39%. $^1$H NMR (400 MHz, DMSO) δ8.01 (d, J=7.4 Hz, 1H), 7.79 (td, J=7.5, 1.2 Hz, 1H), 7.72 (td, J=7.5, 0.9 Hz, 1H), 7.37-7.25 (m, 3H), 7.01 (d, J=7.3 Hz, 1H), 6.81 (d, J=6.7 Hz, 1H), 6.47 (d, J=8.7 Hz, 1H), 6.38 (s, 2H), 6.13 (s, 1H), 3.23-3.10 (m, 2H), 2.98 (d, J=5.0 Hz, 1H), 2.02 (d, J=2.9 Hz, 2H), 1.85-1.75 (m, 2H). $^{13}$C NMR (101 MHz, DMSO) δ168.83, 153.34, 152.90, 149.78, 149.33, 147.24, 146.83, 145.90, 145.24, 144.55, 136.55, 135.57, 130.04, 128.76, 126.35, 124.61, 124.19, 123.96, 123.31, 118.66, 115.22, 115.01, 112.06, 110.74, 110.65, 108.55, 106.10, 104.40, 84.50, 63.19, 49.20, 48.32, 26.76, 21.64, 21.13, 20.73, 18.57. HR ESI [M+H]$^+$ m/z 461.1869, calc. for C$_{30}$H$_{25}$N$_2$O$_3$$^+$461.1859. Compound 40 (20 mg, 0.043 mmol) was dissolved in 15 mL of anhydrous MeOH; 0.75 mL of acetyl chloride was added drop wise. The mixture was stirred and heated at 50° C. for 48 h; then 0.2 mL of acetyl chloride was added and the mixture was kept at 50° C. for additional 24 h. The solvent was evaporated under vacuum. 21 mg (100%) of the target compound 13 was obtained. $^1$H NMR (400 MHz, DMSO) δ8.32 (dd, J=7.9, 1.0 Hz, 1H), 7.96 (td, J=7.5, 1.3 Hz, 1H), 7.92-7.84 (m, 1H), 7.69-7.63 (m, 2H), 7.50 (d, J=6.6 Hz, 1H), 7.30 (d, J=7.6 Hz, 1H), 7.22 (d, J=7.9 Hz, 1H), 6.90-6.79 (m, 2H), 3.73-3.61 (m, 4H), 3.57 (s, 1H), 3.27 (d, J=5.9 Hz, 2H), 2.82-2.74 (m, 2H), 2.10 (dd, J=12.5, 6.5 Hz, 2H), 1.91 (s, 2H). $^{13}$C NMR (101 MHz, DMSO) δ155.99, 152.18, 137.74, 134.11, 133.59, 133.05, 130.65, 129.14, 128.51, 127.30, 125.38, 121.94, 105.05, 64.32, 52.41, 51.21, 50.44, 26.87, 20.30, 19.74, 18.92. HR ESI [M$^+$] m/z 475.2029, calc. for C$_{31}$H$_{27}$N$_2$O$_3$$^+$475.2016.

Example 2

Compound Characterization

Figure 2A:
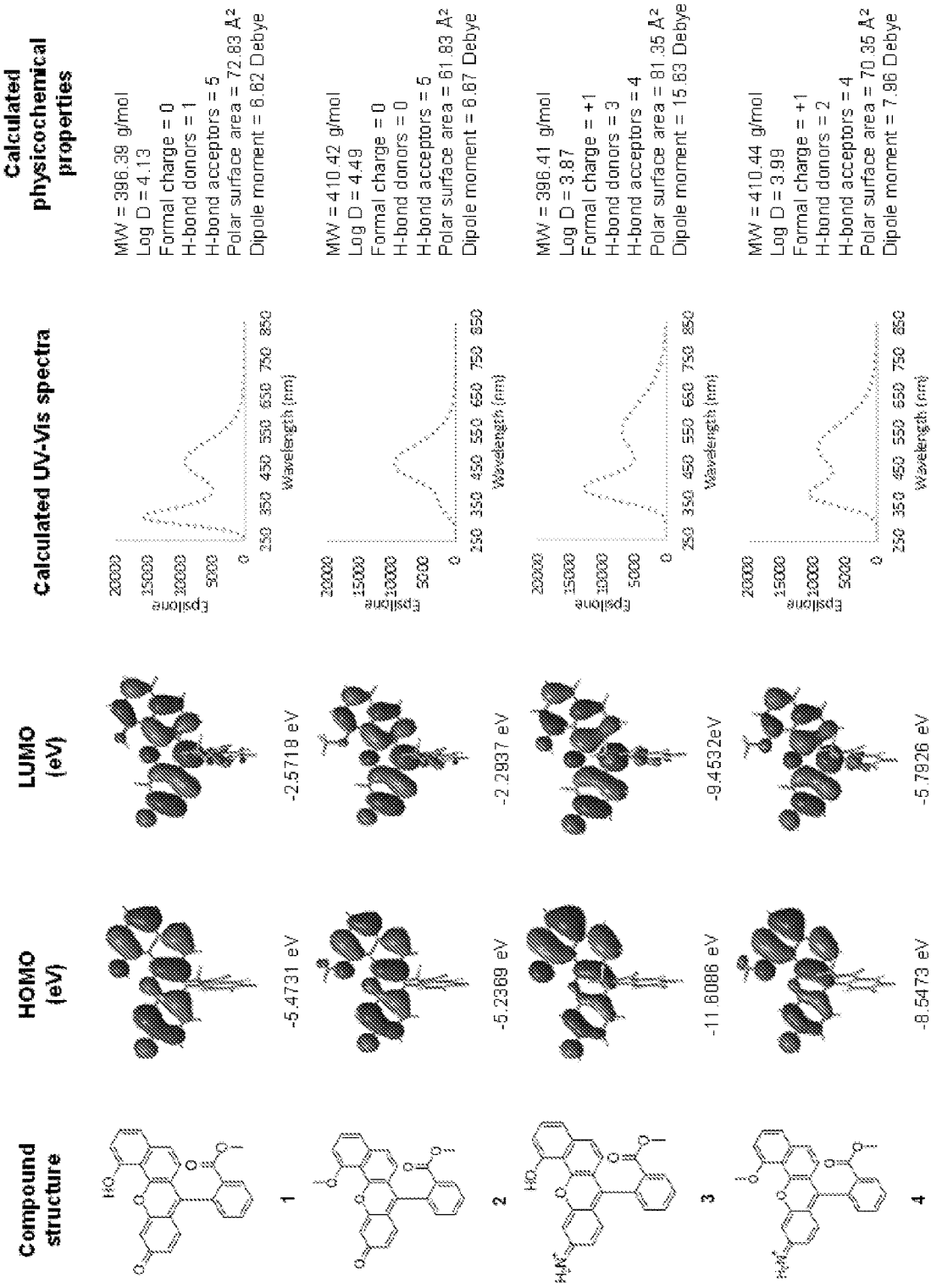
FIGS. 2A-2C show the structure, HOMO, LUMO, calculated absorption spectra and physicochemical properties of compounds 1-13.
Figure 2B:
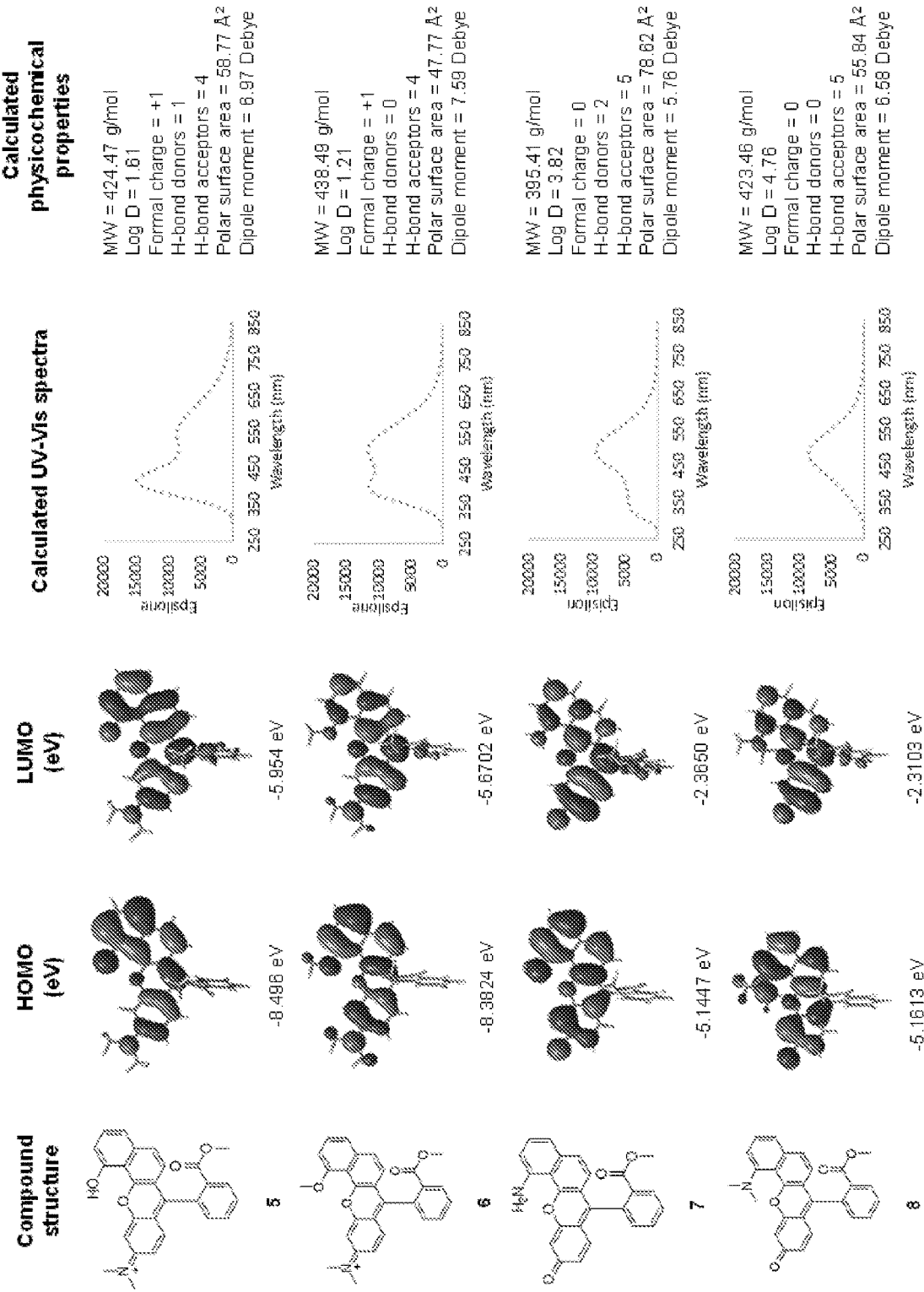
Figure 2C:
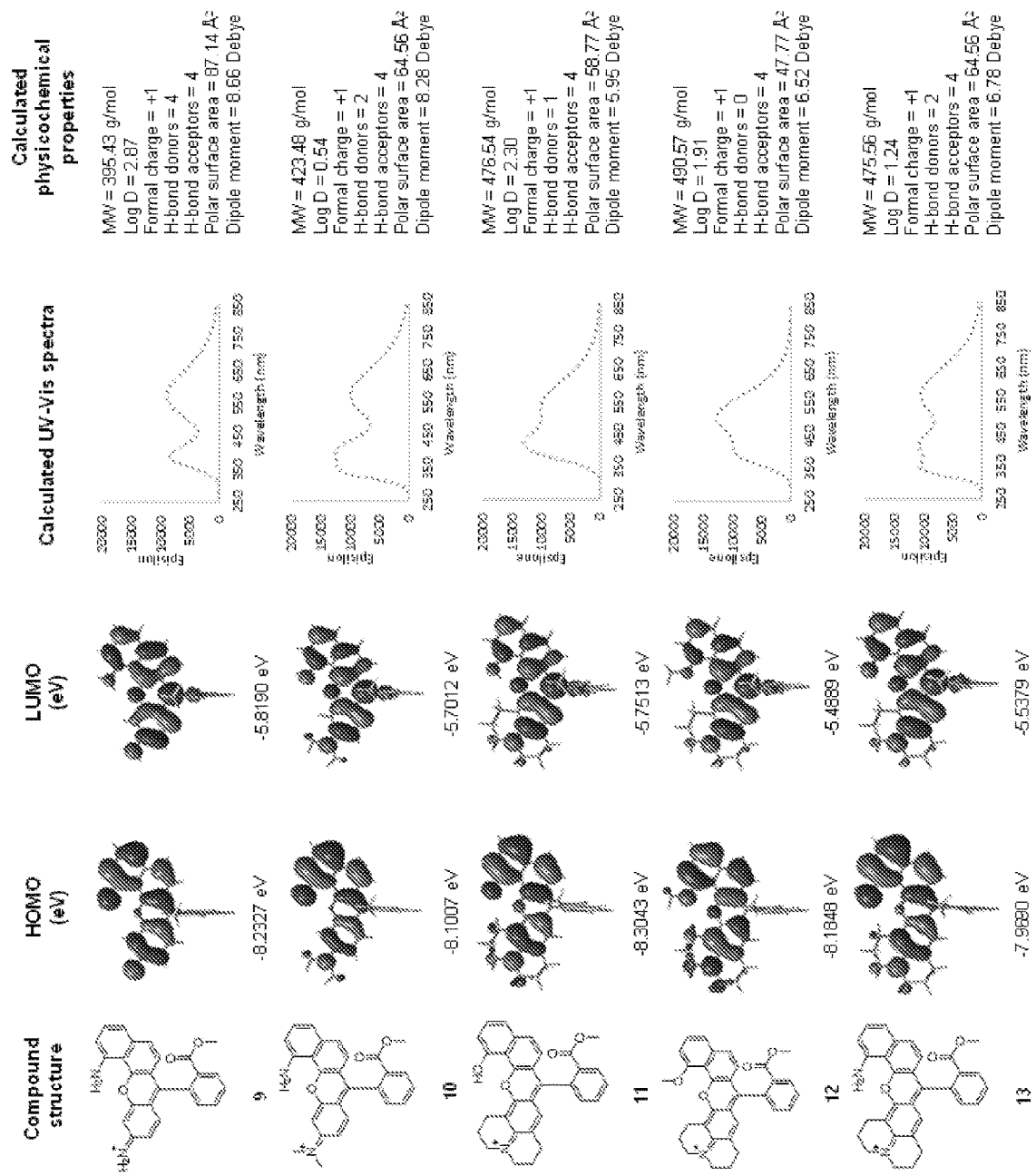

Probes 1-13 (FIG. 1) were designed taking into account absorption and "drug-like" properties that can be used as quantitative descriptors for predicting and optimizing biodistribution and tissue targeting. As shown in FIGS. 2A-2C, each compound has a maximum absorption peak between 400 and 650 nm, a calculated log D value between 0.5 and 5, a molecular weight between 400 and 500 g/mol, 0-4 hydrogen bond donors, <10 hydrogen bond acceptors, and polar surface areas less than 140 Å$^2$, matching the requirements to be considered for tissue targeting according to the Lipinski rules (Lipinski et al., *Advanced Drug Delivery Reviews* 1997, 23: 3-25) and the Veber rules (Veber et al., *J. of Medicinal Chemistry* 2002, 45: 615-2623). Molecular orbital, polar surface area, dipole moment and UV-Vis spectra calculations were carried out using DFT on the gas-phase B3LYP/6-31G level optimized geometries. Physicochemical partition coefficient, log D value at pH 7.4 was calculated using Marvin and JChem calculator plugins (ChemAxon, Budapest, Hungary).

Probes 1-13 were screened for pH and solvent sensitivity. Solvent sensitivity or dependence is at least partially attributable to differences in the equilibria between tautomeric forms of the compounds in the various solvents evaluated. The fluorophore concentrations ranged from 10-15 μM. Aqueous solutions contained 10% DMSO and 12.5 mM HCl, 12.5 mM NaOH, or pH 7.4 phosphate buffer. The UV and fluorescence spectra of the methoxy-functionalized analogs 4, 6 and 12 were insensitive to variations in pH or solvent; these compounds exhibited relatively bright red fluorescence. The three carbonyl-containing compounds, 2, 7 and 8, exhibited spectral properties that were not affected by either solvent changes or by solution pH values above 2, i.e., the spectral properties of these compounds was not pH dependent in the physiological range. The spectral properties of rhodamines 9, 10 and 13, in which the hydroxyl group was preplaced with an amine, were also not pH dependent, but were modestly solvent sensitive. Compounds 1, 3, 5 and 11 contained ionizing hydroxyl groups and thus exhibit pH as well as solvent sensitivity.

The tabulated spectral properties of compounds 1-13 are shown in Tables 1-6 below.

TABLE 1

Dual-emitting seminaphthofluorescein 1 and seminaphthorhodafluors 3, 5, and 11 in acidic solution (pH 1.9, HCl)

| Compound | $\lambda_{max}$ abs (Extinction coefficient) (M$^{-1}$ · cm$^{-1}$) | $\lambda_{max}$ em (Quantum yield) (nm) (%) | Stokes shift (nm) | Brightness | pKa |
|---|---|---|---|---|---|
| 1 | 530 (12,167) | 600 (1.17) | 70 | 142 | 7.72 +/− 0.04 |
| 3 | 542 (19787) | 604 (1.14) | 62 | 226 | 6.67 +/− 0.11 |

TABLE 1-continued

Dual-emitting seminaphthofluorescein 1 and seminaphthorhodafluors 3, 5, and 11 in acidic solution (pH 1.9, HCl)

| Compound | $\lambda_{max}$ abs (Extinction coefficient) (nm) ($M^{-1} \cdot cm^{-1}$) | $\lambda_{max}$ em (Quantum yield) (nm) (%) | Stokes shift (nm) | Brightness | pKa |
|---|---|---|---|---|---|
| 5 | 567 (20399) | 614 (4.09) | 47 | 834 | 6.82 +/− 0.06 |
| 11 | 585 (15134) | 624 (15.29) | 39 | 2314 | 7.84 +/− 0.11 |

Fluorophore concentrations range from 10 to 15 µM. Aqueous solutions contain 10% DMSO and 12.5 mM HCl or NaOH. Species were excited at 480 nm or 510 nm.

TABLE 2

Conjugate bases of seminaphthofluorescein 1 and seminaphthorhodafluors 3, 5, and 11 in basic solution (pH 12.1, NaOH)

| Conjugate base of | $\lambda_{max}$ abs (Extinction coefficient) (nm) ($M^{-1} \cdot cm^{-1}$) | $\lambda_{max}$ em (Quantum yield) (nm) (%) | Stokes shift (nm) | Brightness |
|---|---|---|---|---|
| 1 | 599 (8,613) | 760 (0.19) | 161 | 16 |
| 3 | 621 (15589) | 770 (0.11) | 149 | 17 |
| 5 | 632 (17252) | 780 (0.17) | 148 | 29 |
| 11 | 643 (14454) | 770 (0.30) | 127 | 43 |

Fluorophore concentrations range from 10 to 15 µM. Aqueous solutions contain 10% DMSO and 12.5 mM HCl or NaOH. Species were excited at 630 nm.

TABLE 3

Red-emitting methyl ether derivatives 2, 4, 6, and 12 in pH 7.4 buffer

| Compound | $\lambda_{max}$ abs (Extinction coefficient) (nm) ($M^{-1} \cdot cm^{-1}$) | $\lambda_{max}$ em (Quantum yield) (nm) (%) | Stokes shift (nm) | Brightness |
|---|---|---|---|---|
| 2 | 530 (15,610) | 580 (46.49) | 50 | 7257 |
| 4 | 538 (21742) | 596 (34.42) | 58 | 7484 |
| 6 | 568 (22470) | 606 (9.32) | 38 | 2094 |
| 12 | 582 (17764) | 622 (11.38) | 40 | 2022 |

Aqueous solutions contain 10% DMSO and 12.5 mM pH 7.4 phosphate buffer. Red emitting methyl ether derivatives were excited at 480 nm.

TABLE 4

NIR-emitting seminaphthorhodamines 9, 10, and 13 in pH 7.4 buffer

| Compound | $\lambda_{max}$ abs (Extinction coefficient) (nm) ($M^{-1} \cdot cm^{-1}$) | $\lambda_{max}$ em (Quantum yield) (nm) (%) | Stokes shift (nm) | Brightness |
|---|---|---|---|---|
| 9 | 576 (13872) | 760 (0.18) | 184 | 25 |
| 10 | 598 (17066) | 770 (0.20) | 172 | 34 |
| 13 | 601 (12808) | 740 (0.66) | 139 | 85 |

Aqueous solutions contain 10% DMSO and 12.5 mM pH 7.4 phosphate buffer. NIR emitting seminaphthorhodamines were excited at 630 nm

TABLE 5

Conjugate acids of transposed seminapthorhodafluors 7 and 8 in acidic solution (pH 1.9, HCl)

| Conjugate acid of | $\lambda_{max}$ abs (Extinction coefficient) (nm) ($M^{-1} \cdot cm^{-1}$) | $\lambda_{max}$ em (Quantum yield) (nm) (%) | Stokes shift (nm) | pKa |
|---|---|---|---|---|
| 7 | 598 (3996) | 770 | 172 | 4.99 +/− 0.13 |
| 8 | 480 (10132) | 580 | 100 | 4.36 +/− 0.04 |

Fluorophore concentrations were 15 µM. Aqueous solutions contained 10% DMSO and 12.5 mM HCl, phosphate buffer, or NaOH. Red-emitting species were excited at 480 nm.

TABLE 6

Transposed seminapthorhodafluors 7 and 8 in basic solution (pH 12.1, NaOH)

| Compound | $\lambda_{max}$ abs (Extinction coefficient) (nm) ($M^{-1} \cdot cm^{-1}$) | $\lambda_{max}$ em (Quantum yield) (nm) (%) | Stokes shift (nm) |
|---|---|---|---|
| 7 | 509 (8300) | 530 | 21 |
| 7 | 549 (5664) | 750 | 201 |
| 8 | 530 (8834) | 530 | 21 |

Fluorophore concentrations were 15 µM. Aqueous solutions contained 10% DMSO and 12.5 mM HCl, phosphate buffer, or NaOH. NIR emitting species were excited at 630 nm.

Figure 3:
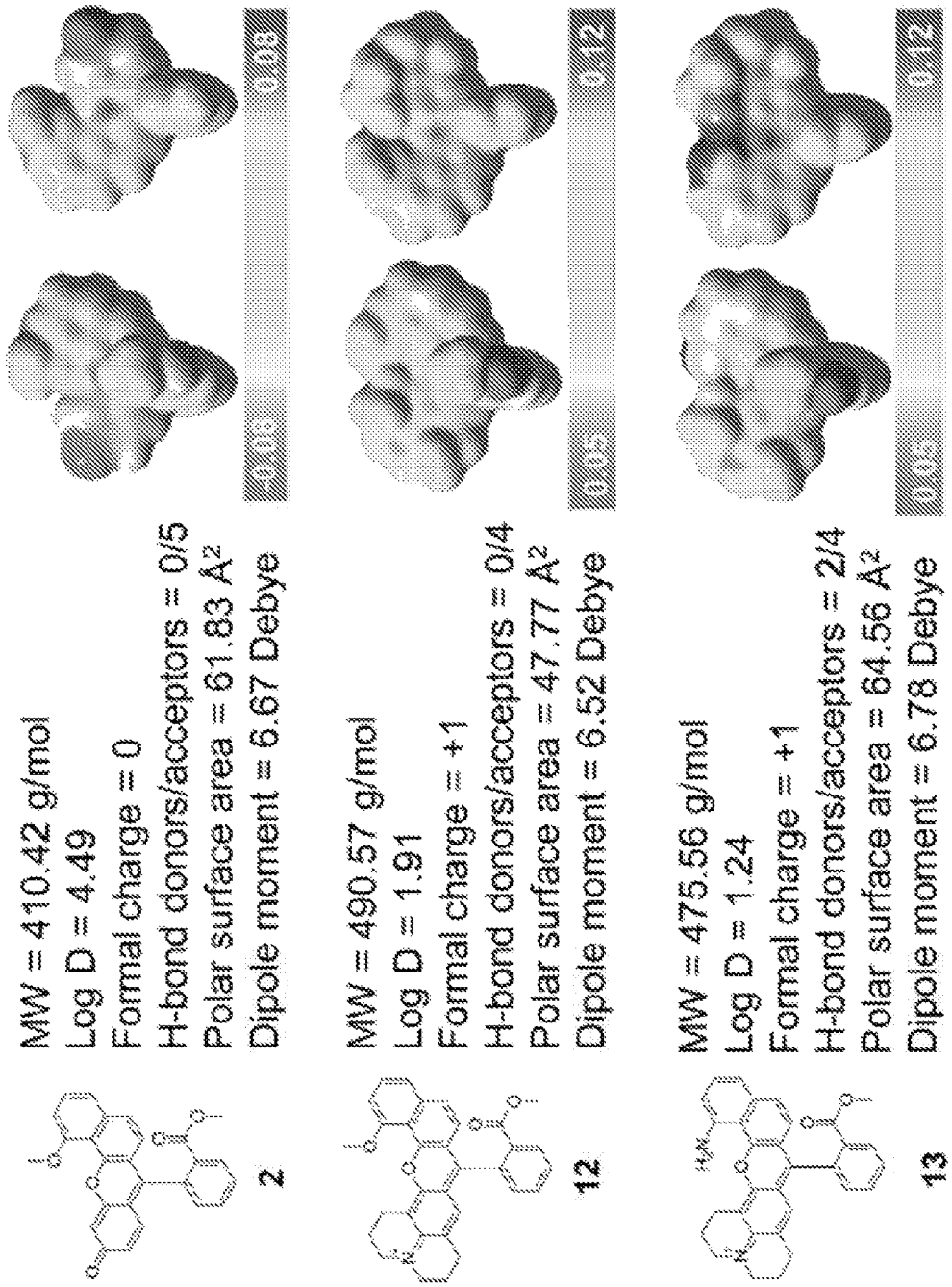
FIG. 3 shows the structures and calculated physicochemical properties of compounds 2, 12, and 13, as well as color-mapped surfaces showing the molecular electrostatic potential (blue is positive, green is neutral, red is negative).

Compounds 2, 12 and 13 were chosen as candidates for initial in vivo screening for pancreas and PDAC targeting based on their brightness, pH insensitivity and the fact that they represented each of three classical dye structures, namely fluorescein (2), rhodafluors (12) and rhodamine (13). FIG. 3 shows the calculated physicochemical properties of compounds 2, 12, and 13. Color-mapped surfaces show the molecular electrostatic potential (blue is positive, green is neutral, and red is negative). Analysis of their calculated "drug-like" properties reveals potential biological activity differences in response to structural variations in the molecular design.

Example 3

Cell Viability

Figure 4:
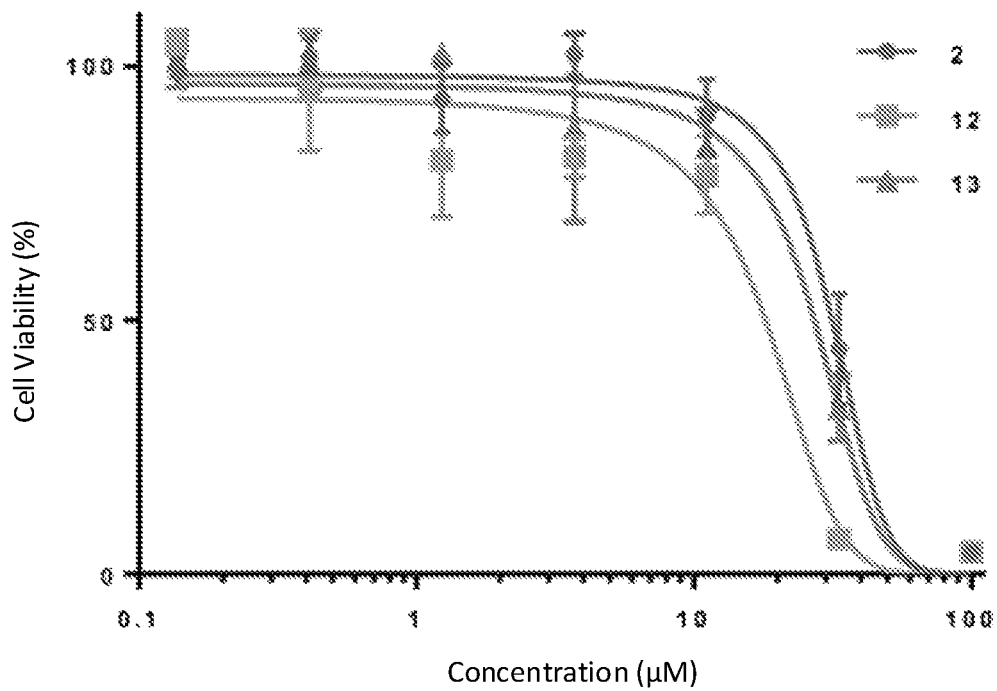
FIG. 4 is a graph showing cytotoxicity of compounds 2, 12, and 13 in Capan-1 (human pancreas) cells.

In vitro cell viability was assessed for compounds 2, 12 and 13 in a representative PDAC cell line, Capan-1. Effective cell viability was determined by CellTiter-Blue assay to measure fluorescence intensity as a function of compound concentration. For reference controls, cells that were treated with 0.4% saponin (in PBS) were the positive control, cells without exposure of toxin were the negative control. The cytotoxicity studies demonstrated that compound 2 was the least toxic ($IC_{50}$ 30.08 µM) followed by compounds 13 ($IC_{50}$ 26.08 µM) and 12 ($IC_{50}$ 17.79 µM) (FIG. 4).

Figure 5:
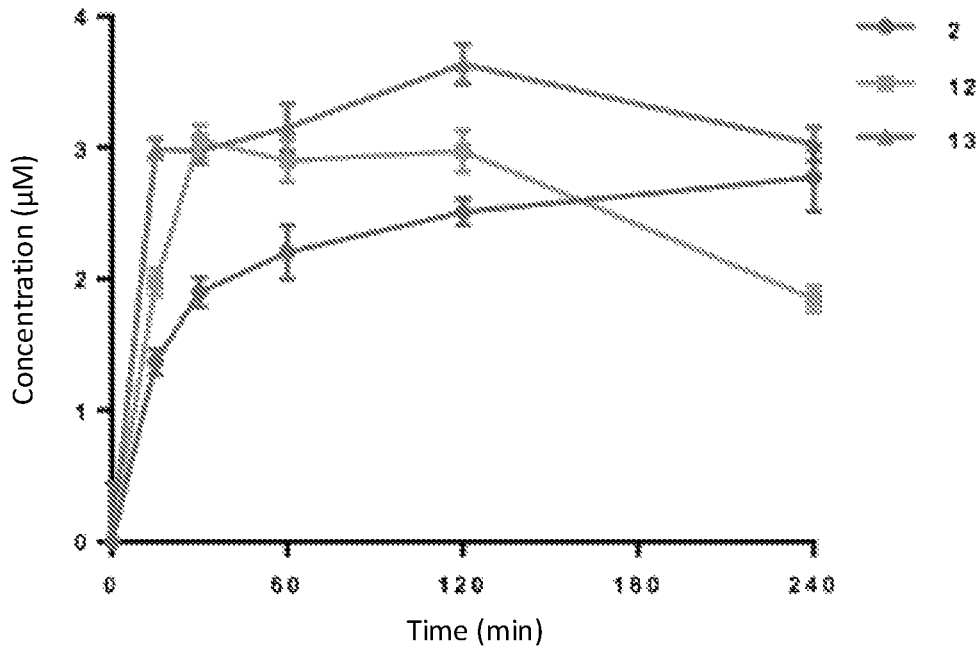
FIG. 5 is a graph showing in vitro time-dependent uptake of compounds 2, 12, and 13 in Capan-1 cells.

In vitro time-dependent fluorophore uptake was also investigated in Capan-1 cells. Cellular uptake was determined by exposure of the cells to 10 µM of synthesized compounds. Absorbance of the media was measured to quantify fluorophore uptake by the cells. Data is presented as the mean±S.D (n=3). Each fluorophore exhibited similar kinetics demonstrating uptake within 30 min of fluorophore application, where compound 13 had the greatest fluorophore uptake and 2 the lowest during this period. The uptake differences were attributed to the favorable membrane interactions of the cationic fluorophores 12 and 13 as compared to the neutral compound 2. After 30 min, all compounds showed a slowly increased uptake, which lasted for up to 2 h. Compounds 12 and 13 began clearing from the cells after 2 h (FIG. 5).

Example 4

Subcellular Localization of Compounds

The subcellular localization of 2, 12 and 13 was investigated in Capan-1 cells after 1 h incubation time. Organelle-specific fluorescent probes were used to assess site specific uptake of each novel fluorophore. FIGS. 6A, 7A, and 8A show the red fluorescence of the three compounds, respectively, as well as blue fluorescence with DAPI (4,6-diamidino-2-phenylindole) FIGS. 6C, 7C, 8C) and green fluorescence with organelle-specific fluorescent probes—ER-Tracker™ Green (BODIPY® FL dye and glibenclamide; ThermoFisher Scientific) (FIGS. 6E, 7E, 8E) and MitoTracker® Green (benzoxazolium 2-[3-[5,6-dichloro-1,3-bis[[4-(chloromethyl)-phenyl]methyl]-1,3-dihydro-2H-benzimidazol-2-ylidene]-1-propenyl]-3-methyl-chloride201860-17-5v; ThermoFisher Scientific) (FIGS. 6G, 7G, 8G). Also shown are composite overlays of (i) phase contrast+compound fluorescence (FIGS. 6B, 7B, 8B), (ii) DAPI+compound fluorescence (FIGS. 6D, 7D, 8D), (iii) DAPI+ER-Tracker™ Green+compound fluorescence (FIGS. 6F, 7F, 8F), and (iv) DAPI+MitoTracker® Green+compound fluorescence (FIGS. 6H, 7H, 8H).

The preferential site of intracellular localization of compound 2 appeared to be within vesicular structures, which could be lipid droplets, endosomes, or other membrane based vesicles within the cells. In contrast to compound 2, compounds 12 and 13 demonstrated more homogeneous distribution across cells with extensive accumulation in the mitochondria as well as limited accumulation in the nucleus and endoplasmic reticulum (ER). Because compounds 12 and 13 are cationic, they tend to distribute electrophoretically into the mitochondrial matrix in response to the electric potential across the mitochondrial membrane.

Example 5

Biodistribution

Figure 9A:
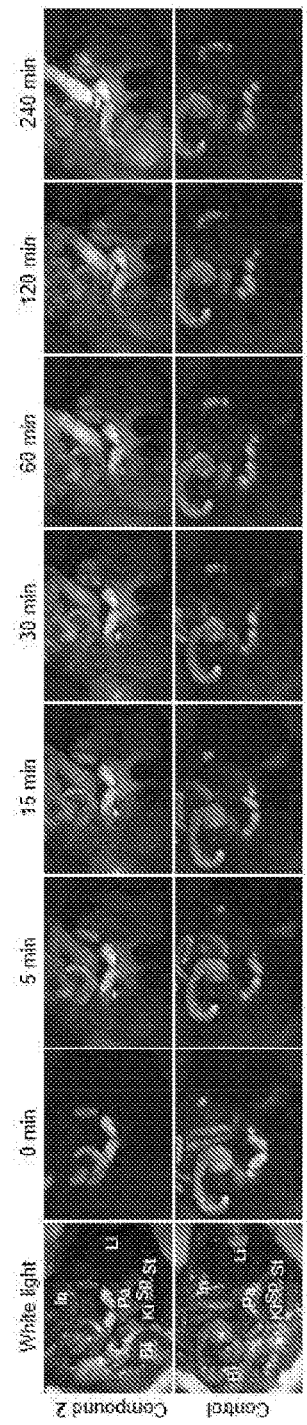
FIGS. 9A-9D are representative intraoperative white light and fluorescence images in the peritoneal cavity over time following systemic administration of compound 2 (9A), 12 (9B), 13 (9C), and methylene blue (MB) (9D).
Figure 9B:
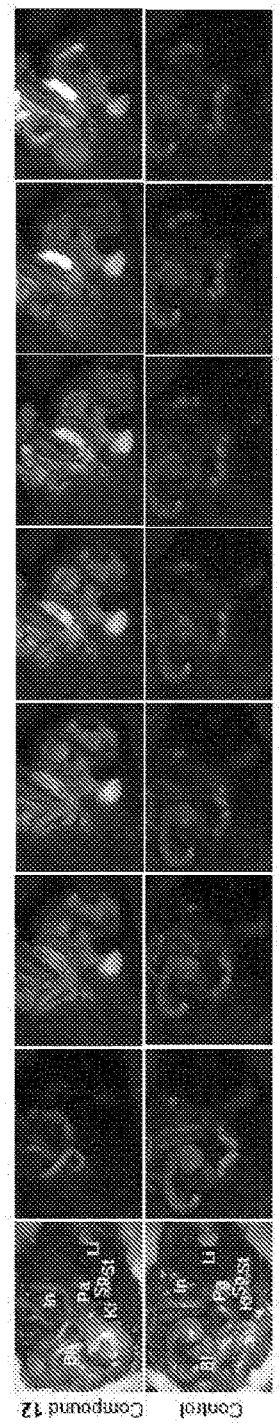
Figure 9C:
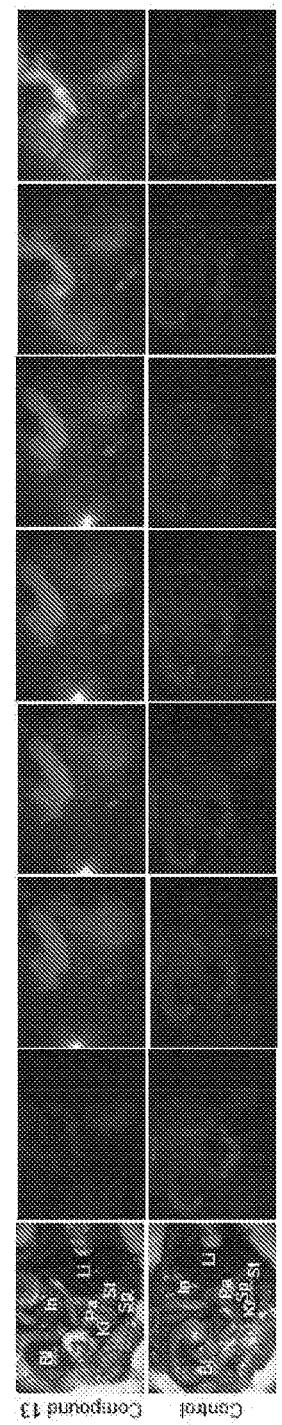
Figure 9D:
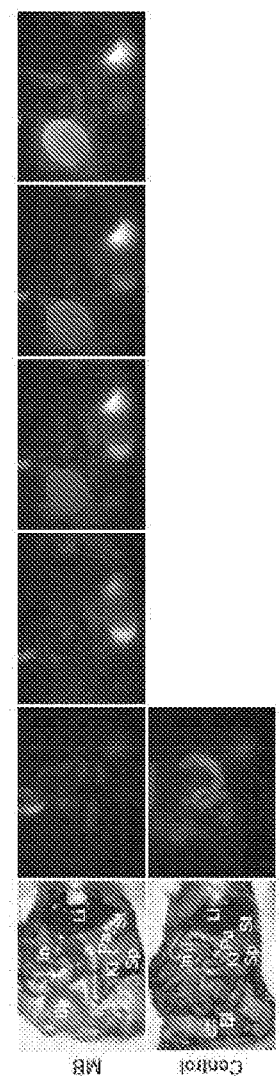
Figure 10:
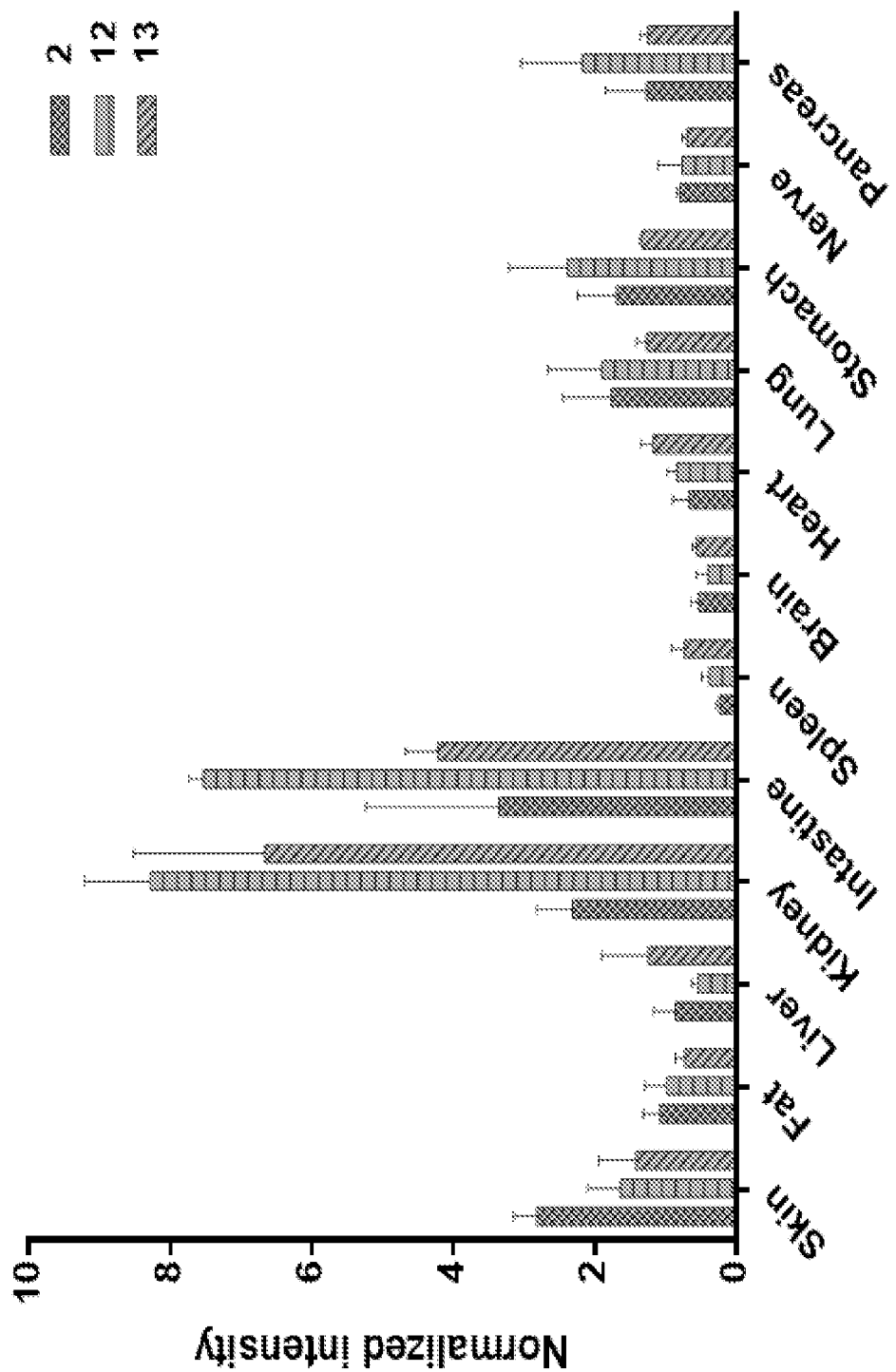
FIG. 10 is a graph comparing ex vivo resected organ normalized fluorescence intensity of compounds 2, 12, and 13. All mean fluorescence intensity was calculated for n=3 injected mice per compound. Fluorescence intensities for each organ were normalized to the muscle fluorescence intensity per animal. Data is presented as the mean±S.D.
Figure 11A:
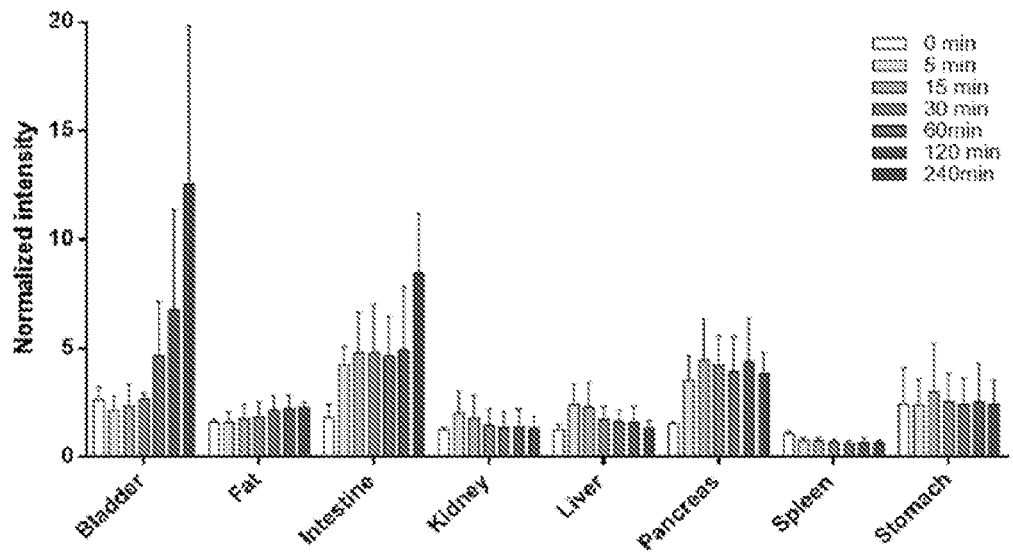
FIGS. 11A-11D are graphs of normalized mean fluorescence intensity showing in vivo organ biodistribution following systemic administration of compound 2 (11A), compound 12 (11B), compound 13 (11C), and MB (11D). Mean fluorescence intensity was calculated for n=3 injected mice per compound. Fluorescence intensities for each organ were normalized to the muscle fluorescence intensity per animal per time point. Data is presented as the mean±S.D.
Figure 11B:
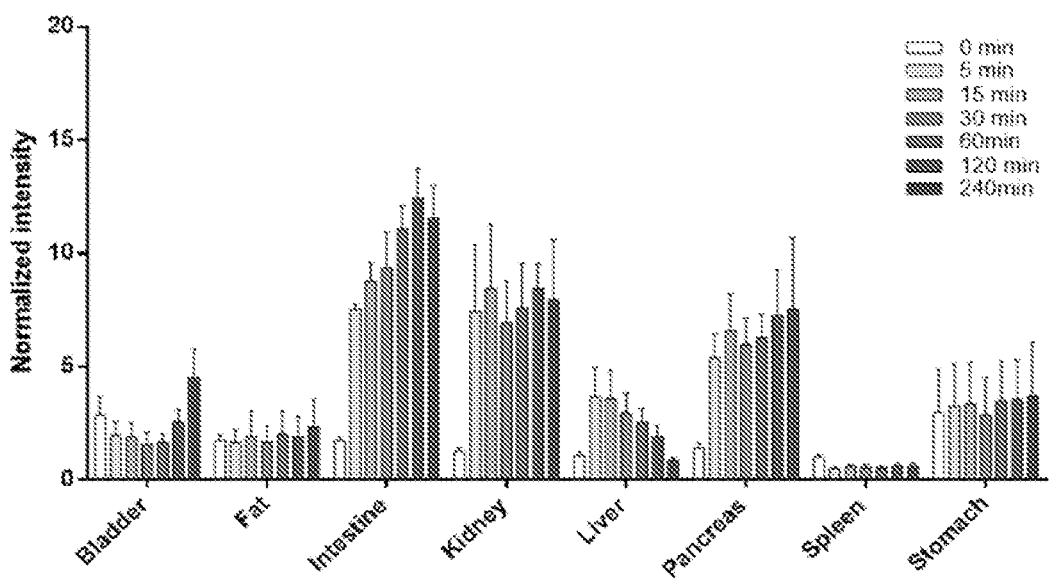
Figure 11C:
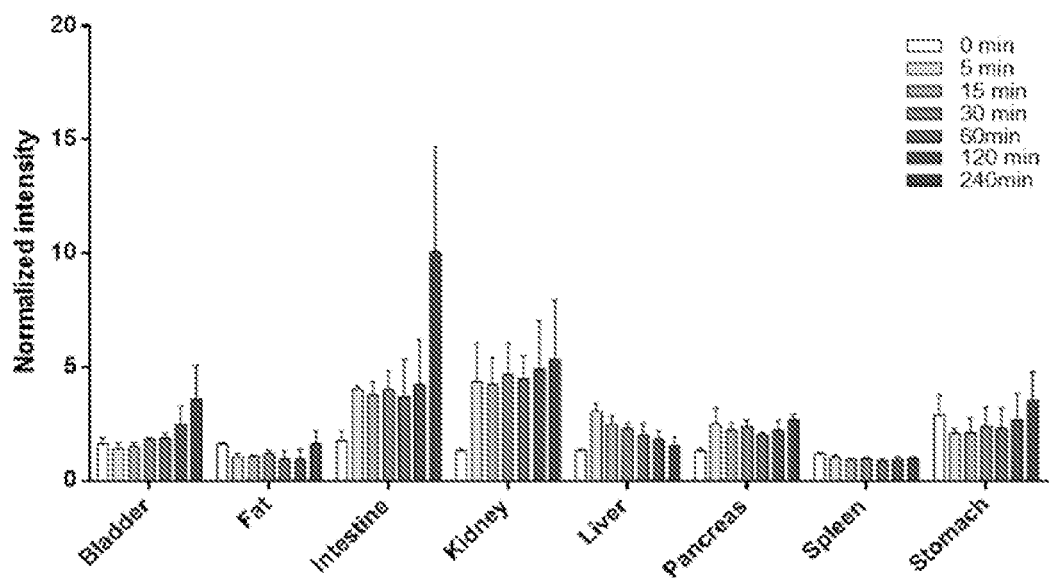
Figure 11D:
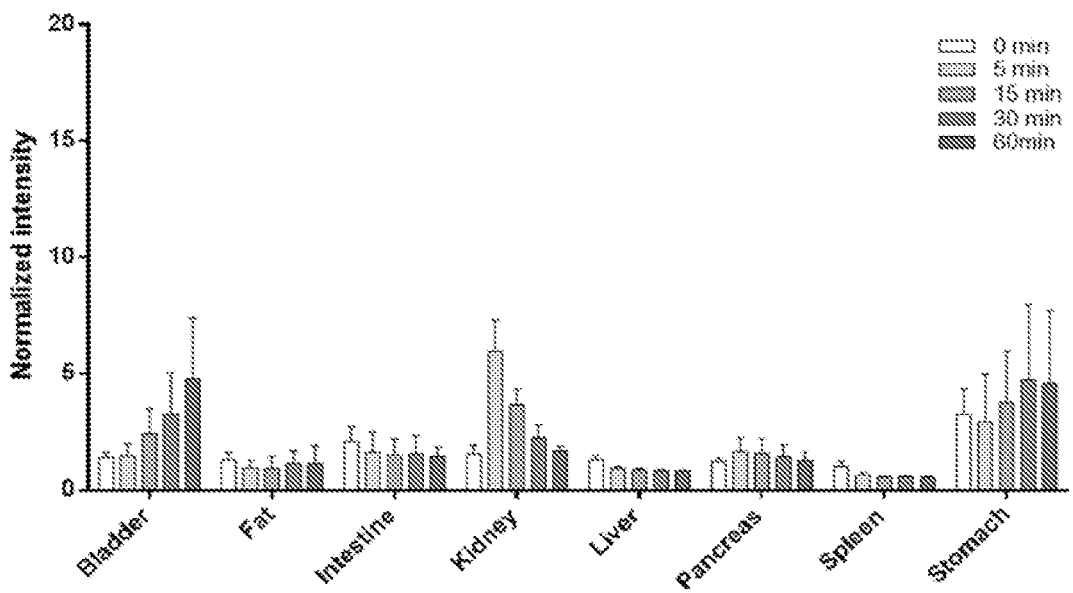

Initial biodistribution profile screening of 2, 12, and 13 was carried out in healthy CD-1 mice and compared to methylene blue (MB) to assess the pancreas specificity of the novel fluorophores. Compounds 2, 12, 13 (100 nmol) or methylene blue (120 nmol) were injected intravenously (n=3 mice per compound). Fluorescence images were collected prior to fluorophore administration enabling each animal to act as its own control and at 0, 5, 15, 30, 60 min for 2, 12 and 13 and MB, as well as for an additional 3 h for compounds 2, 12 and 13. Representative intraoperative fluorescence image series over time as well as resected organ SBR comparison are shown in FIGS. 9A-9D and 10. All images in FIGS. 9A-9D are representative of data collected for n=3 systemically injected mice per compound. All fluorescence images were collected at 50 ms exposure time. All images are displayed with equivalent normalization between time points and to images of a control, uninjected mouse. In=Intestine; Li=liver; Pa=pancreas; Sp=spleen; St=stomach; Bl=Bladder; Ki=Kidney. FIG. 10 compares ex vivo resected organ normalized fluorescence intensity of compounds 2, 12, and 13. The graph shows mean resected organ fluorescence intensity 4 hours after systemic administration of compounds 2, 12, or 13.

Despite their structural similarities, the in vivo biodistribution of each of the three tested fluorophores were distinct as assessed by intraoperative imaging throughout the 4 h distribution phase (FIGS. 11A-11D). Compound 2 preferentially accumulated in the pancreas, intestine and bladder, demonstrating significant renal clearance. Compound 12 accumulated in the kidney, pancreas, and intestine, demonstrating both renal and hepatic clearance. Compound 13 accumulated largely in the kidneys, with significant clearance from the other assessed organs 4 h after systemic administration.

Although all three probes accumulated in the kidney and liver soon after administration, their preferable clearance routes and rates from these organs differed with respect to renal clearance vs. hepatic clearance. Compound 2 showed faster renal clearance than compounds 12 and 13, as bladder fluorescence was the highest for this fluorophore. Renal clearance of compound 2 was expected since it had the smallest molecular size and weight of the tested compounds. Compounds 12 and 13 cleared more slowly than compound 2 and were retained in the kidney for relatively longer periods. Compound 12 exhibited a greater hepatic excretion rate as compared to compounds 2 and 13. The accumulation profiles of compounds 2 and 13 in the intestine were similar, even though compound 2 was more lipophilic and less water soluble compared to compound 13. The overall profiles in other quantified tissues including adipose, spleen, and stomach were similar. Compound 12 exhibited the highest and most persistent fluorescence SBR in the pancreas as compared to surrounding organs at the 4-h time point. Compound 12 exhibited 4-fold higher uptake in normal pancreas tissue than the previously tested MB (log D=−0.62). MB extravasated to some degree but demonstrated poor penetration into normal pancreas tissue (FIG. 9D). The low in vivo efficacy of MB could be attributed to its low lipophilicity and high water solubility, as it is preferentially and rapidly cleared through the renal system after systemic administration. In addition, MB's low quantum yield/tissue fluorescence, rapid clearance rate and reduced bioavailability limited its pancreas tissue selectivity and thus its potential for image-guided surgery applications. From the study herein, higher log D value compounds 2 and 12 exhibited improved pancreas specificity whereas 13 and MB had relatively lower log D values and diminished pancreas accumulation.

Example 6

Intraoperative Fluorescence Imaging in Mice

Genetically engineered mice models of PDAC tumors that recapitulate the clinical, pathological and genomic features of human PDAC (Guerrera et al., *Molecular Oncology* 2013, 7: 232-247; Di Magliano et al., *Gastroenterology* 2013, 144-: 1120-1229; Hingorani et al., *Cancer Cell* 2003, 4: 437-450) were used to assess the specificity of the novel fluorophores for PDAC accumulation. Since compound 12 afforded the highest pancreas tissue uptake, it was chosen for study in the genetically modified PDAC tumor-bearing mouse model.

Ex vivo staining of pancreas tissue from healthy and PDAC mice showed that each exhibited characteristic tissue structures was clearly highlighted with 12 (FIG. 12A). The healthy mouse pancreas tissue showed uptake of 12 in its abundant acinar cell population. In contrast, in the cancerous tissue, 12 localized in the PDAC-associated ductal epithelial cells, enabling them to be observed via increased fluorescence signal that was visually brighter compared to that of the acinar cells in healthy tissue. Thus 12 enabled ex vivo staining to distinguish the features of healthy and PDAC tissue.

Compound 12 was systemically administered to n=5 genetically modified PDAC mice. Pancreas specific fluorescence was monitored over 1.5 h. Significantly more fluorescence was seen in compound 12 injected PDAC bearing animals compared to uninjected control PDAC bearing animals. FIGS. 12B and 12C show real-time intraoperative fluorescence imaging of compound 12 in the PDAC mice. FIG. 12B shows color images of the pancreas in the peritoneal cavity outlined in yellow, with (upper panel) and without (lower panel) compound 12, as well as fluorescence images obtained after injection of compound 12. FIG. 12C shows macroscopic images of resected pancreas tissue from PDAC tumor bearing mice ex vivo either following systemic administration of compound 12 (upper panel) or from an uninjected mouse (lower panel) confirming the lack of pancreas fluorescence without 12. The images of mice injected with 12 are representative of data collected for n=5 injected PDAC mice. All fluorescence images were collected at 50 ms exposure time. Images are displayed with equal normalization between compound 12 and the uninjected control. Accumulation of compound 12 in PDAC tumor tissue was significantly higher than in the surrounding healthy tissue.

Figure 13A:
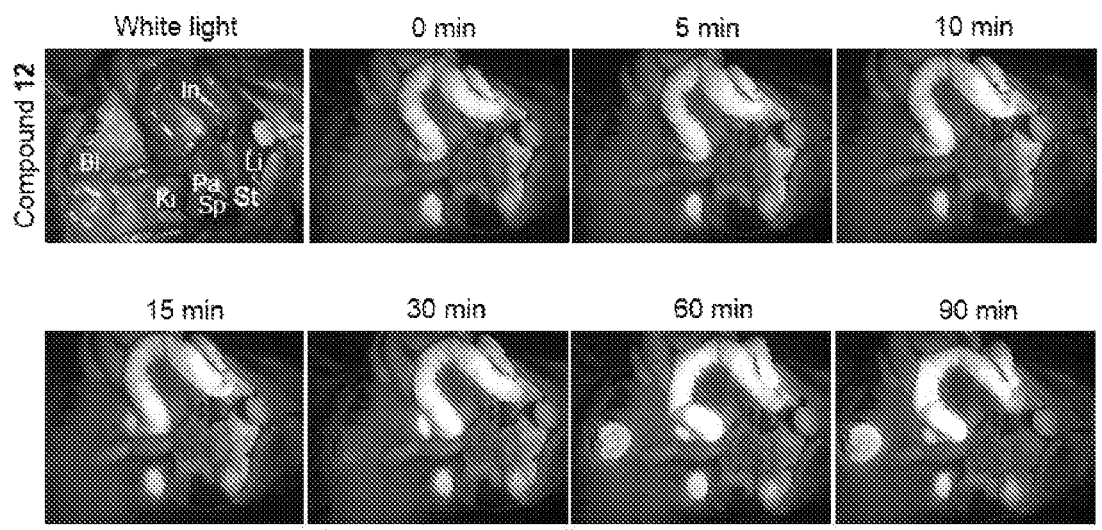
FIG. 13A shows representative intraoperative white light and fluorescence images in the peritoneal cavity over time following systemic administration of compound 12 in a PDAC tumor bearing mouse.
Figure 13B:
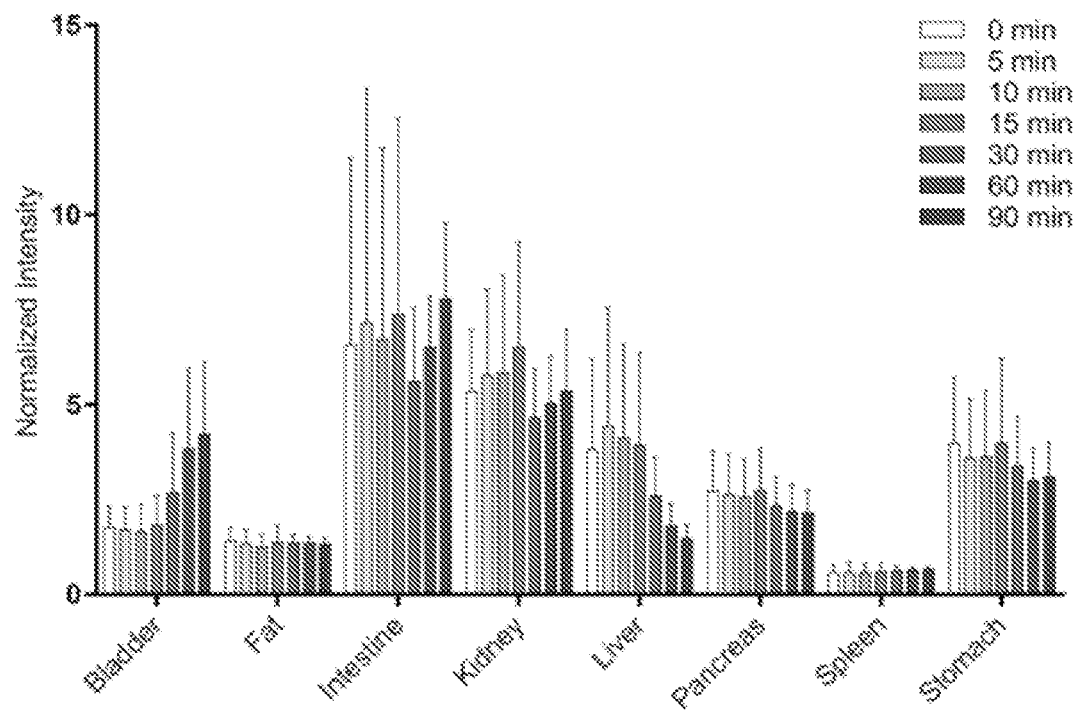
FIG. 13B shows normalized mean fluorescence intensity showing in vivo organ biodistribution following systemic administration of compound 12. Quantified fluorescence intensity for each organ was normalized to the muscle intensity per animal per time point. Data is presented as the mean+/−S.D.
Figure 14A:
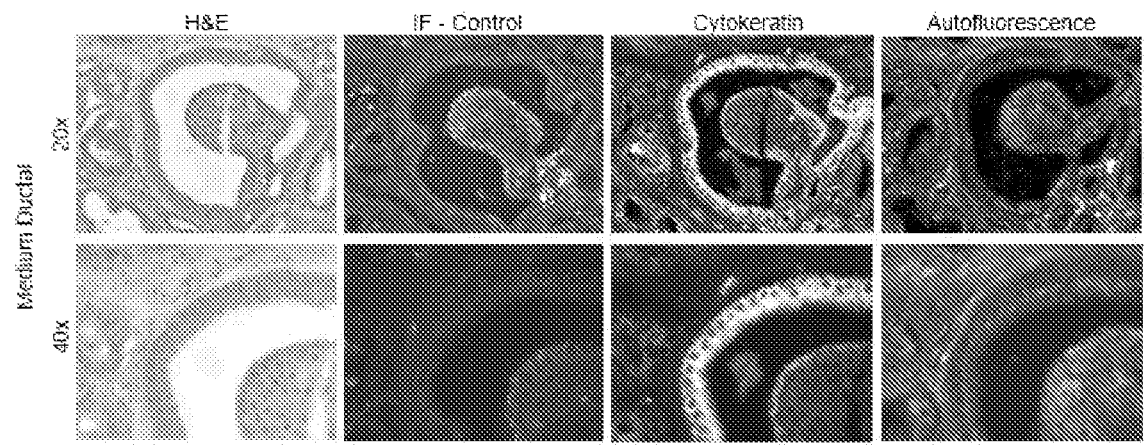
FIGS. 14A-14C are representative microscopy images of hematoxylin & eosin (H&E), pan-cytokeratin unstained and stained medium (14A) and large (14B) duct type adenocarcinoma tissue, and of pancreatic acinar cells next to small duct type adenocarcinoma tissue resected from uninjected PDAC tumor bearing mice (14C).
Figure 14B:
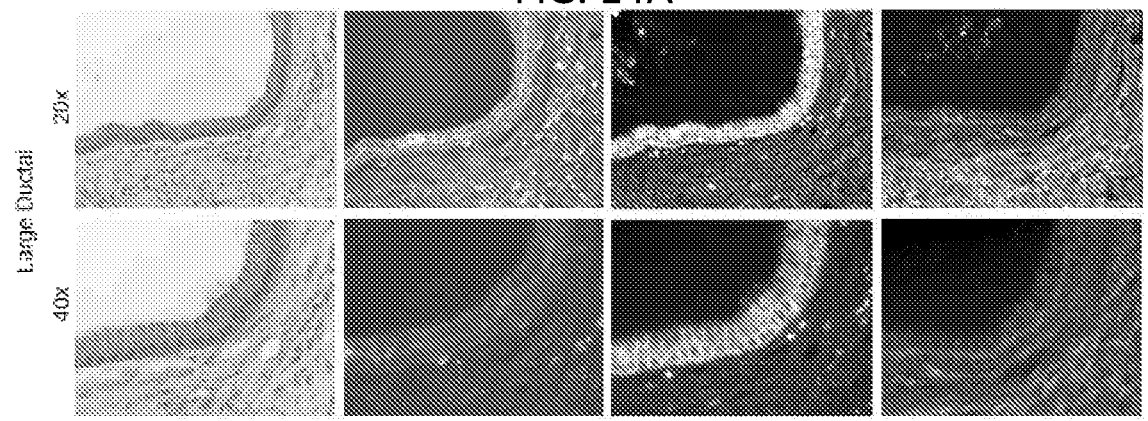
Figure 14C:
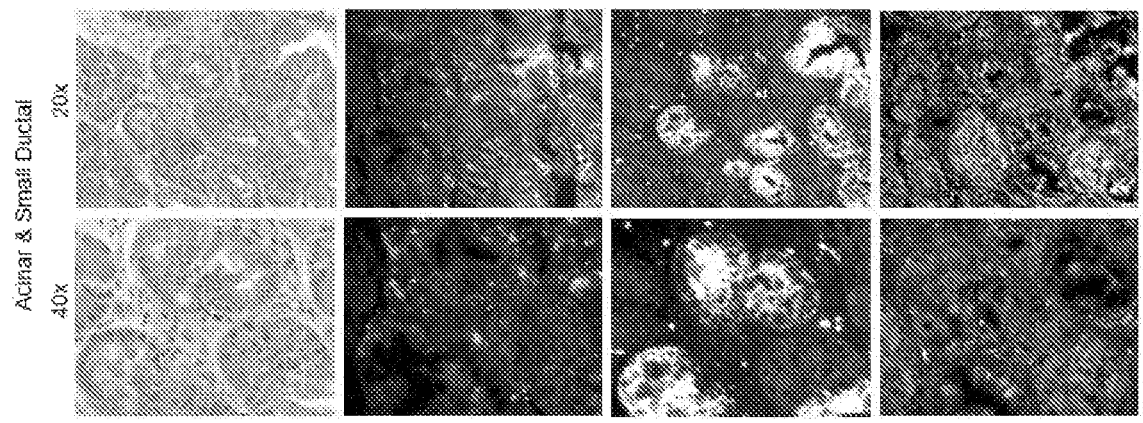
Figure 15A:
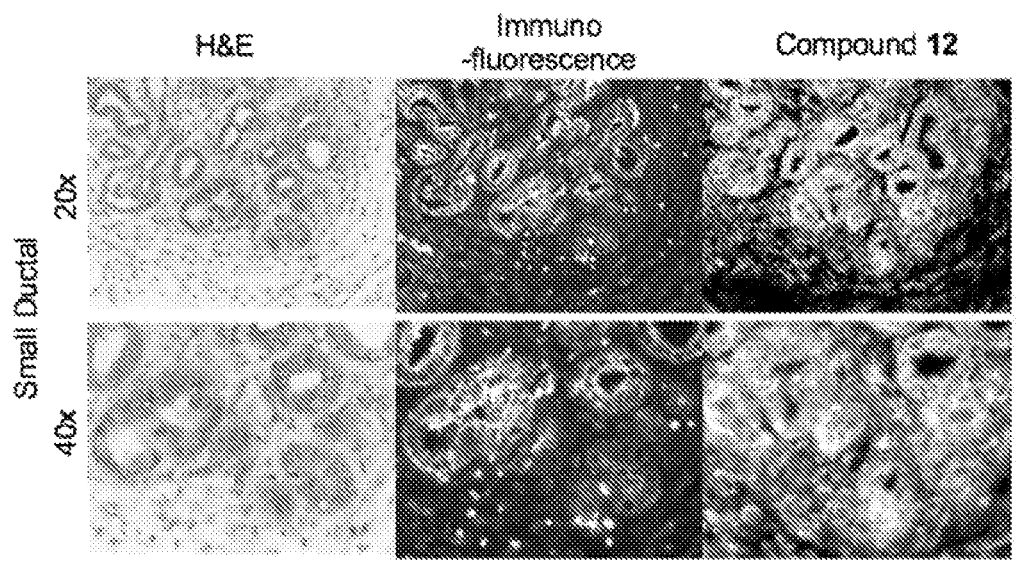
FIGS. 15A-15D are microscopy images of H&E, pan-cytokeratin, and compound 12 stained slides showing ex vivo pathology of resected tissue from representative small (15A), medium (15B), and large (15C) duct type adenocarcinoma tissue as well as acinar cells (15D) resected from PDAC tumor-bearing mice injected with 12. Pan-cytokeratin antibody staining specifically highlighted PDAC cells, demonstrating compound 12 specificity for PDAC.
Figure 15B:
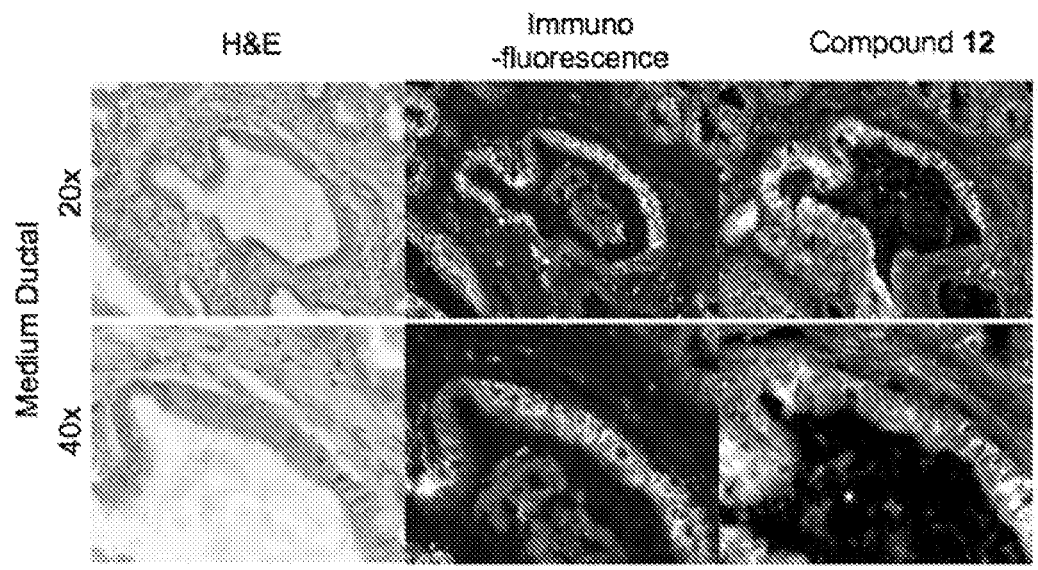
Figure 15C:
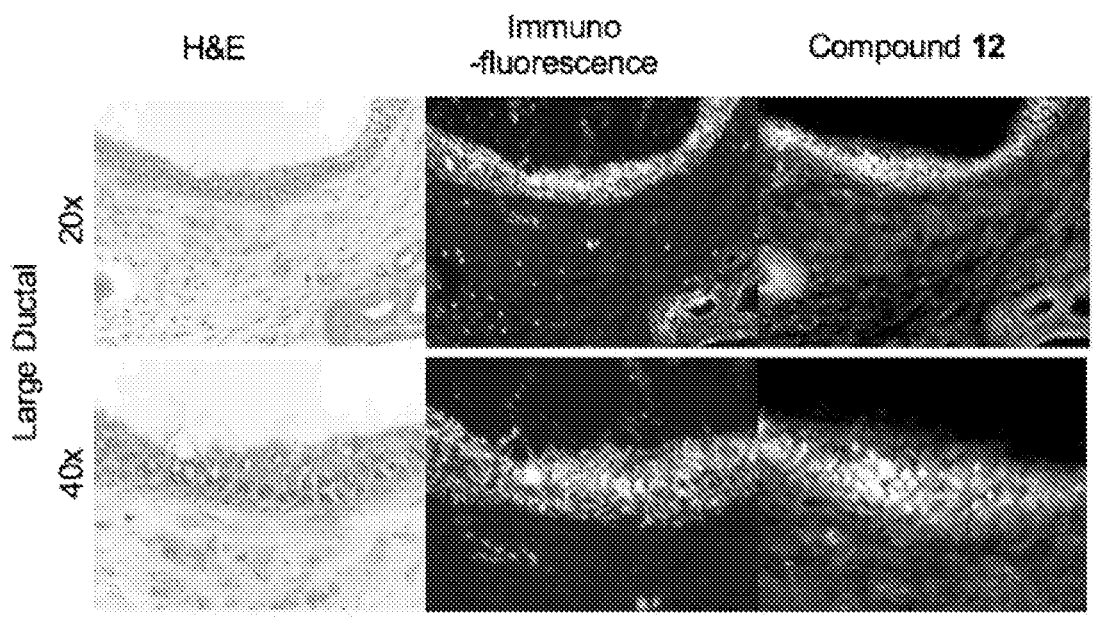
Figure 15D:
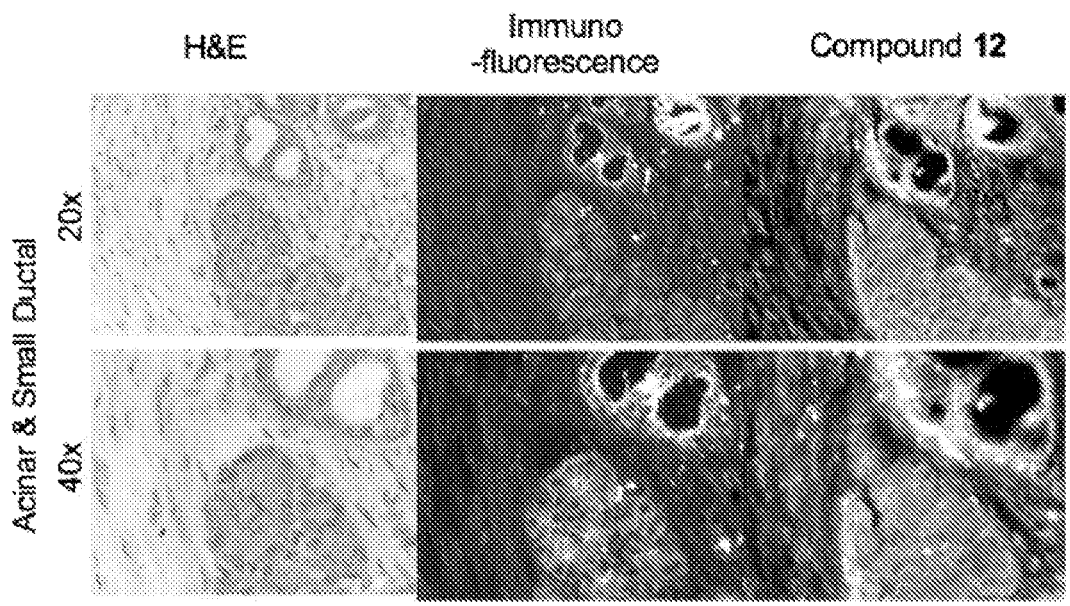

After euthanasia, the pancreas was assessed microscopically for PDAC specific fluorophore accumulation. Representative intraoperative fluorescence images over time as well as in vivo organ biodistribution kinetics of compound 12 are shown FIGS. 13A-13B, and 14A-14C. FIG. 13A shows representative images of the fluorescence intensity in the peritoneal cavity over time following systemic administration of compound 12 in PDAC tumor bearing mice. FIG. 13B shows corresponding mean fluorescence intensities measured for each organ. All images are representative of data collected for n=5 systemically administered mice. All fluorescence images were collected at 50 ms exposure time. All images are displayed with equivalent normalization between time points. Quantified fluorescence intensity for each organ was normalized to the muscle intensity per animal per time point. Data is presented as the mean+/−S.D. In=Intestine; Li=liver; Pa=pancreas; Sp=spleen; St=stomach; Bl=Bladder; Ki=Kidney. FIGS. 14A-14C are representative microscopy images of medium (FIG. 14A) and large (FIG. 14B) duct type adenocarcinoma tissue, and of normal pancreatic acinar cells next to small duct type adenocarcinoma tissue resected from uninjected PDAC tumor bearing mice (FIG. 14C). Control immunofluorescence (IF) images were collected from serial sections that had been stained using the same procedure as those for cytokeratin visualization, but with blank staining solution to demonstrate antibody staining specificity. Images were collected in the compound 12 fluorescence channel and are normalized to compound 12 fluorescence images in FIGS. 15A-15D for each respective tissue type to demonstrate autofluorescence in the compound 12 fluorescence channel in unstained PDAC tissue Representative serially sectioned tissues stained with pan-cytokeratin to assess PDAC specificity of compound 12 confirmed that accumulation of compound 12 in PDAC tumor tissue was significantly higher than in the surrounding tissues and specific for the malignant cells (FIGS. 15A-15D). Hematoxylin and Eosin (H&E) staining of the PDAC specimens revealed that uptake of compound 12 occurred in small (15A), medium (15B), and large (15C) ductal tissue epithelial cells. This is consistent with the fact that pancreatic ductal epithelial cells give rise to PDAC. Furthermore, the accumulation of compound 12 in acinar cells (FIG. 15D) demonstrated co-localization with the pan-cytokeratin immunofluorescence staining, aligning with studies that have shown that genetic mutations of acinar cells are associated with precancerous pancreatic intraepithelial neoplasia that progresses to PDAC over time.

Example 7

In Vivo Cancer Imaging

A compound as disclosed herein is systemically administered to a subject having or suspected of having pancreatic cancer. After waiting an effective amount of time for the compound to be taken up by pancreatic cancer cells, fluorescence imaging is used to verify the presence and location of pancreatic cancer in the subject. Fluorescence-guided surgery is performed to precisely visualize malignant tissue and determine cancer margins. Malignant tissue is removed from the subject.

For example, a composition comprising compound 12 and a pharmaceutically acceptable carrier is intravenously injected into a live subject. After an effective amount of time, such as 60-120 minutes (e.g., 90 minutes), the subject's pancreatic tissue, and optionally areas surrounding the pancreas, is exposed in vivo to a light source providing light having a wavelength from 530-560 nm, e.g., a light source filtered with a 545±12.5 nm bandpass excitation filter. Exposing the pancreatic tissue to the light source may include an open abdominal procedure, laparoscopic exposure, or endoscopic exposure. Suitable intraoperative fluorescence imaging systems include, but are not limited to, the FLARE® Device (Frangioni Laboratory, Curadel, LLC), the Fluobeam® imaging system (Fluoptics), the Artemis Handheld System (Quest Innovations), PDE near infrared fluorescence imagers (Hamamatsu), and SPY Elite (Novadaq). Fluorescence is detected at a wavelength from 570-640 nm (e.g., using a 605±35 nm bandpass emission filter) with areas of fluorescence indicating presence of pancreatic cancer cells. Camera exposure times may be from 50 to 200 ms. Guided by the fluorescence, malignant tissue is removed from the subject. Preferably, sufficient malignant tissue is removed to provide clear margins after the malignancy is removed.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. The probe having a chemical structure according to general formula II

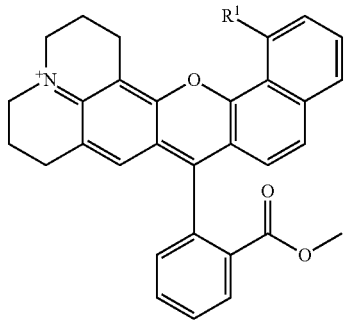

where $R^1$ is —$OCH_3$ or —$NH_2$.

2. The probe of claim 1 where $R^1$ is —$OCH_3$.

3. A method for detecting pancreatic cancer cells, comprising:
   contacting pancreatic tissue with a probe according to claim 1, and
   detecting pancreatic cancer cells by detecting fluorescence from the probe.

4. The method of claim 3 where detecting fluorescence from the probe comprises detecting fluorescence at a wavelength corresponding to an emission spectrum maximum of the probe.

5. The method of claim 3 where contacting the pancreatic tissue is performed in vivo.

6. The method of claim 3 where contacting the pancreatic tissue comprises administering the probe to a subject having or suspected of having pancreatic cancer.

7. The method of claim 3 where administering the probe comprises administering a composition comprising the probe and a pharmaceutically acceptable carrier.

8. The method of claim 3 where the probe is administered systemically.

9. The method of claim 7 where the probe is administered intraoperatively.

10. The method of claim 3 where contacting the pancreatic tissue with the probe is performed ex vivo.

11. The method of claim 10, where detecting fluorescence from the probe is performed 1-30 minutes after contacting the pancreatic tissue with the probe.

12. The method of claim 3 where the pancreatic cancer cells are pancreatic ductal adenocarcinoma cells or pancreatic intraepithelial neoplasia cells.

13. The method of claim 3 where the probe is

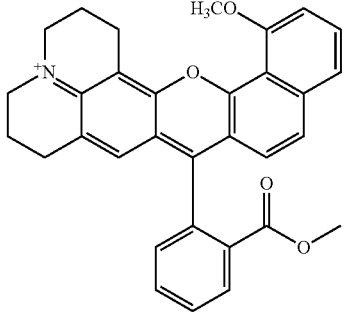

14. The method of claim 13 where detecting fluorescence from the probe comprises:
   exposing the pancreatic tissue to a light source providing light having a wavelength from 530-560 nm; and
   detecting fluorescence at a wavelength of from 570-640 nm.

* * * * *